(12) United States Patent
Gryaznov et al.

(10) Patent No.: US 10,905,767 B2
(45) Date of Patent: Feb. 2, 2021

(54) OLIGONUCLEOTIDE CONSTRUCTS AND USES THEREOF

(71) Applicant: Janssen BioPharma, Inc., South San Francisco, CA (US)

(72) Inventors: Sergei Gryaznov, San Mateo, CA (US); Leonid Beigelman, San Mateo, CA (US); Theodore Yun, Burlingame, CA (US)

(73) Assignee: Janssen BioPharma, Inc., South San Francisco, CA (US)

( * ) Notice: Subject to any disclaimer, the term of this patent is extended or adjusted under 35 U.S.C. 154(b) by 0 days.

(21) Appl. No.: 16/179,786

(22) Filed: Nov. 2, 2018

(65) Prior Publication Data

US 2019/0160173 A1 May 30, 2019

Related U.S. Application Data

(60) Provisional application No. 62/580,924, filed on Nov. 2, 2017.

(51) Int. Cl.

| *A61K 47/54* | (2017.01) |
| *A61P 31/20* | (2006.01) |
| *A61P 35/00* | (2006.01) |
| *A61K 39/39* | (2006.01) |
| *A61K 47/22* | (2006.01) |
| *A61K 47/26* | (2006.01) |
| *C12Q 1/6876* | (2018.01) |
| *A61K 47/14* | (2017.01) |
| *A61K 9/00* | (2006.01) |
| *A61K 31/7088* | (2006.01) |
| *A61K 39/00* | (2006.01) |

(52) U.S. Cl.
CPC .......... *A61K 47/543* (2017.08); *A61K 9/0019* (2013.01); *A61K 31/7088* (2013.01); *A61K 39/39* (2013.01); *A61K 47/14* (2013.01); *A61K 47/22* (2013.01); *A61K 47/26* (2013.01); *A61K 47/545* (2017.08); *A61P 31/20* (2018.01); *A61P 35/00* (2018.01); *C12Q 1/6876* (2013.01); *A61K 2039/55561* (2013.01); *A61K 2039/58* (2013.01); *A61K 2039/585* (2013.01); *A61K 2039/6018* (2013.01); *A61K 2039/6025* (2013.01); *A61K 2039/82* (2018.08); *C12N 2730/10134* (2013.01)

(58) Field of Classification Search
CPC ...... A61K 2039/55561; A61K 2039/58; A61K 2039/6018; A61K 2039/6025; A61K 47/26; A61K 47/543; A61P 35/00
USPC ............ 435/6.1, 91.31, 455, 458; 514/44 A; 536/23.1, 24.5
See application file for complete search history.

(56) References Cited

U.S. PATENT DOCUMENTS

| 5,378,825 | A | 1/1995 | Cook et al. |
| 5,386,023 | A | 1/1995 | Sanghvi et al. |
| 5,489,677 | A | 2/1996 | Sanghvi et al. |
| 10,016,451 | B2 * | 7/2018 | Edelson ............... A61K 9/0014 |
| 10,076,535 | B2 * | 9/2018 | Klinman ............ A61K 31/7036 |
| 10,100,316 | B2 * | 10/2018 | Epstein ................ C12N 15/115 |
| 2007/0280929 | A1 * | 12/2007 | Hoerr .................... A61K 31/355 424/130.1 |

FOREIGN PATENT DOCUMENTS

| WO | WO 1992/20822 A1 | 11/1992 |
| WO | WO 1992/20823 A1 | 11/1992 |
| WO | WO 2005/030259 A2 | 4/2005 |
| WO | WO 2013/151771 A1 | 10/2013 |
| WO | WO 2015/126502 A2 | 8/2015 |
| WO | WO 2015/187966 A1 | 12/2015 |
| WO | WO 2018/179172 A1 | 10/2018 |

OTHER PUBLICATIONS

Barratt et al., "Preparation and characterisation of liposomes containing mannosylated phospholipids capable of targeting drugs to macrophages.", Biochim. Biophys. Acta, 1986, pp. 153-164, vol. 862.
Beaucage, S. L. and Iyer, R. P., "The Synthesis of Modified Oligonucleotides by the Phosphoramidite Approach and Their Applications.", Tetrahedron, 1993, pp. 6123-6194, vol. 49.
Bijsterbosch et al., "Modulation of plasma protein binding and in vivo liver cell uptake of phosphorothioate oligodeoxynucleotides by cholesterol conjugation.", Nucleic Acids Res., 2000, pp. 2717-2725, vol. 28(14).
Diebold et al., "Mannose Receptor-Mediated Gene Delivery into Antigen Presenting Dendritic Cells.", Somat. Cell Mol. Genetics, Nov. 2002, pp. 65-74, vol. 27(1/6).
Isogawa et al., "Toll-Like Receptor Signaling Inhibits Hepatitis B Virus Replicaton in Vivo.", J. Virology, 2005, pp. 7269-7272, vol. 79(11).
Kaczanowska et al., "TLR agonists: our best frenemy in cancer immunotherapy.", J Leukoc Biol. Jun. 2013, pp. 847-863, vol. 93(6).
Kinzel et al., "Synthesis of a Functionalized High Affinity Mannose Receptor Ligand and its Application in the Construction of Peptide-, Polyamide- and PNA-Conjugates.", J. Peptide Sci., 2003, pp. 375-385, vol. 9.
Kwong et al., "Induction of potent anti-tumor responses while el iminating systemic side effects via liposome-anchored combinatorial inmunotherapy.", Biomaterials, Mar. 28, 2011, pp. 5134-5147, vol. 32(22), XP028214646.
Lui et al., "Structure-based progranming of lymph-node targeting in molecular vaccines", Nature, Feb. 16, 2014, pp. 519-522, vol. 507(7493), XP055229918.
Wolfrum, C., et al., "Mechanisms and optimization of in vivo delivery of lipophilic siRNAs.", Nat Biotechnol, Oct. 2007, pp. 1149-1157, vol. 25(10).

(Continued)

Primary Examiner — Jane J Zara

(57) ABSTRACT

Oligodeoxynucleotide-based immunostimulatory Toll-Like Receptor 9 (TLR9) agonists are described. Also described are compositions comprising the TLR9 agonists, methods of making the TLR9 agonists, and methods of using the TLR9 agonists to treat immune diseases, disorders or conditions, such as viral infections or cancer.

2 Claims, 37 Drawing Sheets

Specification includes a Sequence Listing.

(56) References Cited

OTHER PUBLICATIONS

Xu et al., "Hepatitis B Virus-Related Hepatocellular Carcinoma: Pathogenic Mechanisms and Novel Therapeutic Interventions.", *Gastrointest Tumors*, 2014, pp. 135-145, vol. 1(3).

Yu et al., "Inmunostimulatory Properties of Lipid Modified CpG Oligonucleotides.", Molecular Pharmaceutics, Jul. 24, 2017, pp. 2815-2823, vol. 14(8), XP055557190.

International Search Report relating to co-pending International Patent Application No. PCT/IB2018/058628, filed Nov. 2, 2018, dated Feb. 25, 2019.

Written Opinion of the International Searching Authority relating to co-pending International Patent Application No. PCT/IB2018/058628, filed Nov. 2, 2018, dated Feb. 25, 2019.

Biessen, et al., "Lysine-based Cluster Mannosides that Inhibit Ligand Binding to the Human Mannose Receptor at Nanomolar Conventration.", J. Biological Chemistry, 1996, pp. 28024-28030, vol. 271(45).

Yamamoto, et al., "Current View of Toll-Like Receptors Signaling Pathways.", Gastroenterology Research and Practice, 2010, pp. 1-8, vol. 1010.

* cited by examiner

FIG. 3
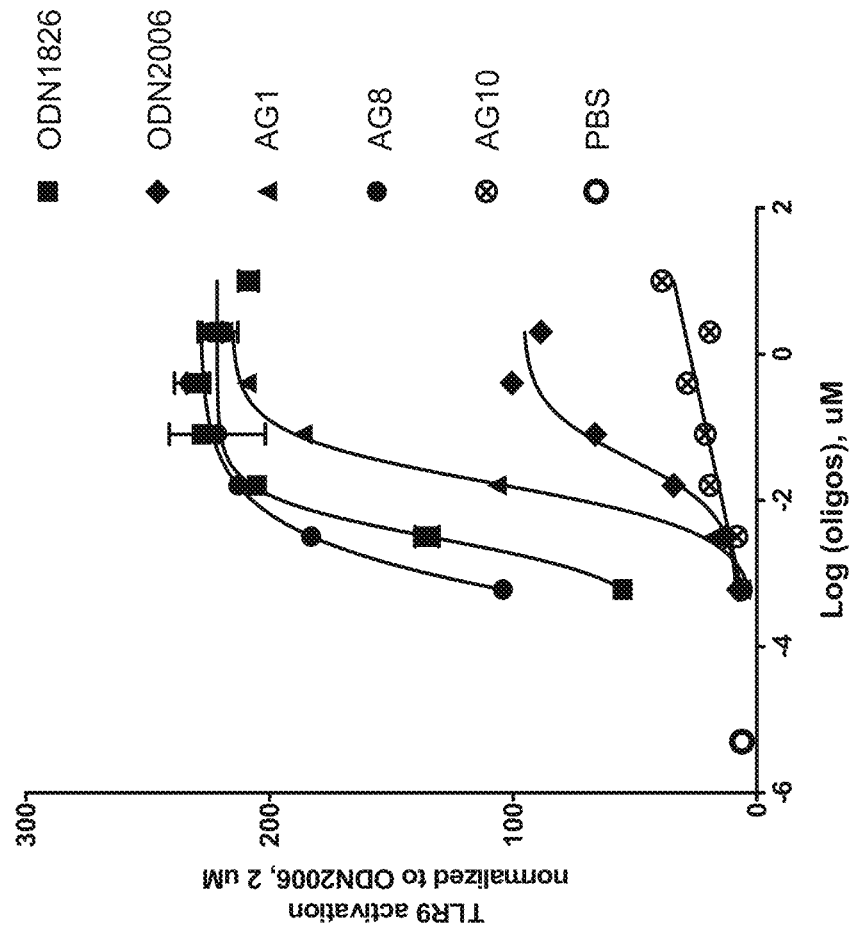
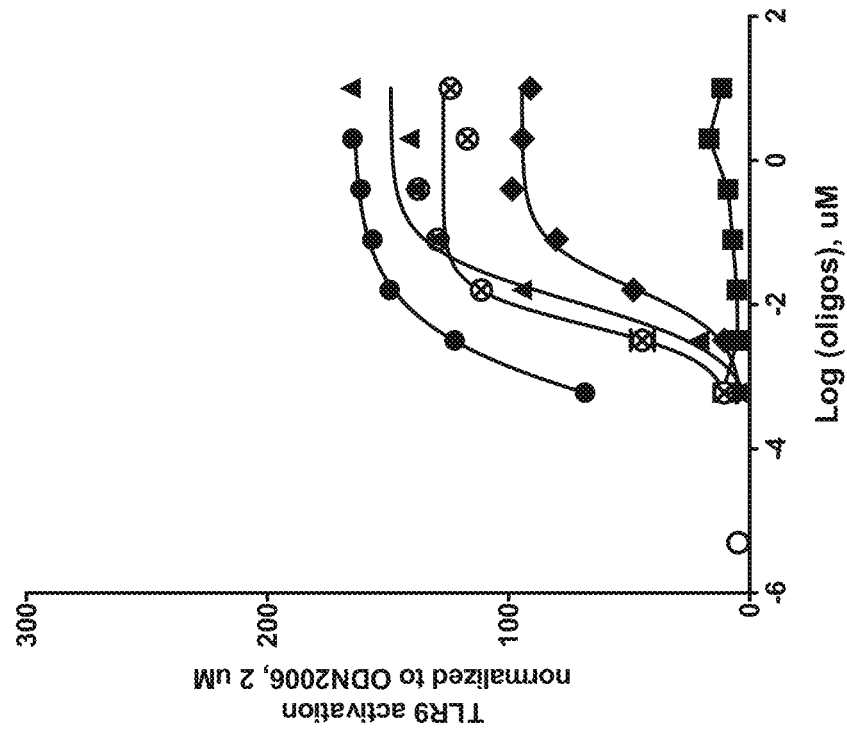

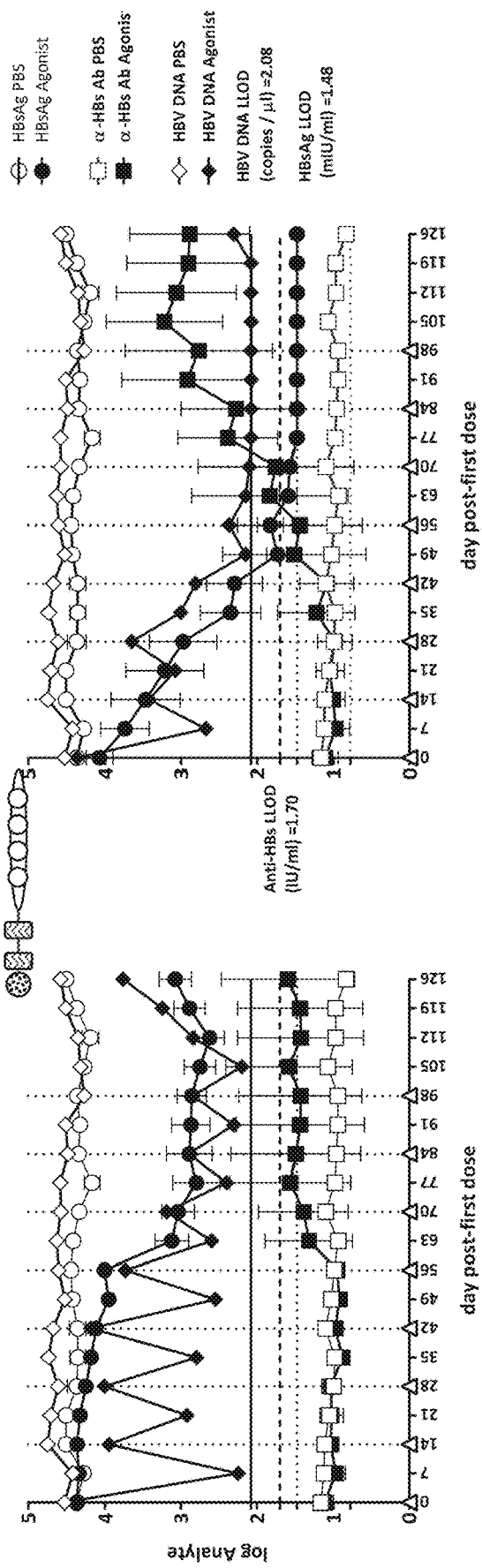
FIG. 13A  Subcutaneous, 10.8 mpk
FIG. 13B  Intravenous, 5.4 mpk

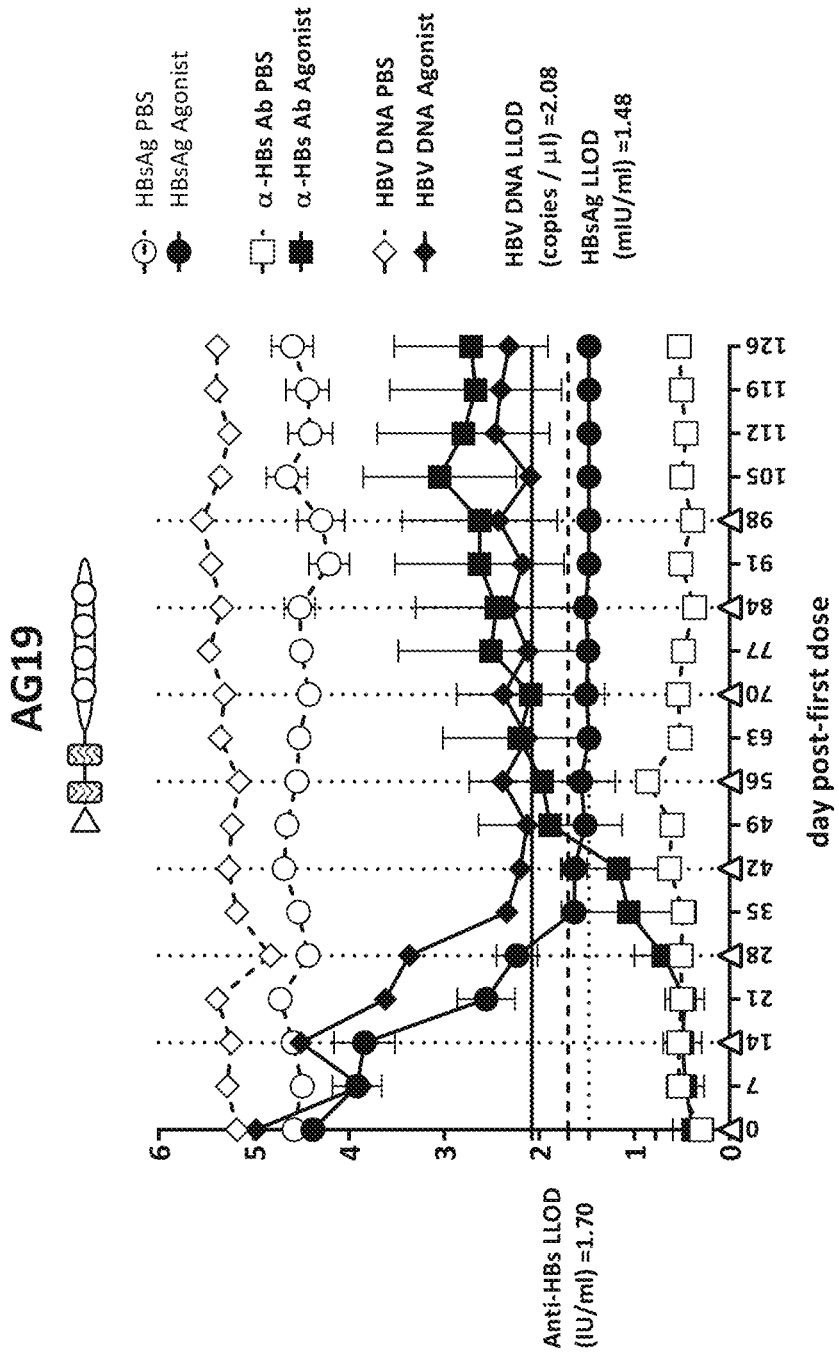

FIG. 21A
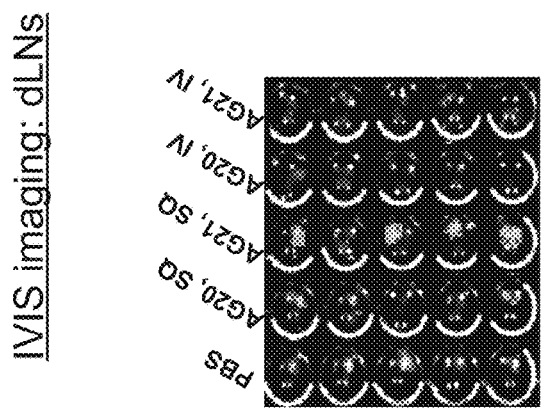
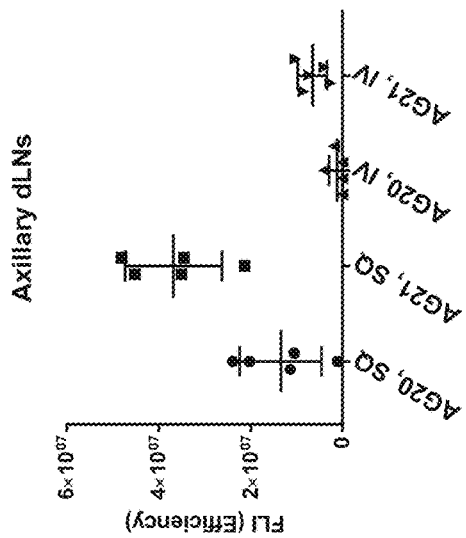
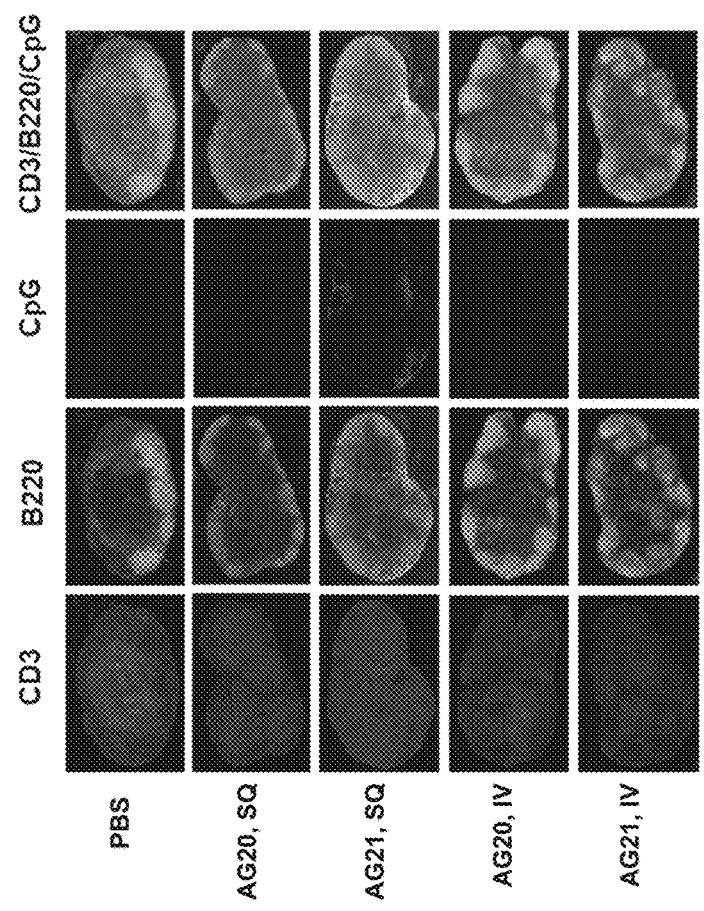

OLIGONUCLEOTIDE CONSTRUCTS AND USES THEREOF

CROSS REFERENCE TO RELATED APPLICATIONS

This application is entitled to priority pursuant to 35 U.S.C. § 119(e) to U.S. Provisional Patent Application No. 62/580,924, filed Nov. 2, 2017, the disclosure of which is incorporated by reference herein in its entirety.

REFERENCE TO SEQUENCE LISTING SUBMITTED ELECTRONICALLY

This application contains a sequence listing, which is submitted electronically via EFS-Web as an ASCII formatted sequence listing with a file name "688097_119U1 Sequence Listing", creation date of Oct. 31, 2018, and having a size of 11.3 KB. The sequence listing submitted via EFS-Web is part of the specification and is herein incorporated by reference in its entirety FIELD OF THE INVENTION The present disclosure relates to oligonucleotide constructs, compositions comprising the oligonucleotide constructs, and methods of making the oligonucleotide constructs. The oligonucleotide constructs can act as immunomodulatory molecules and, in particular, as Toll-Like Receptor 9 (TLR9) agonists. Accordingly, the present disclosure also relates to methods of using the oligonucleotide constructs as TLR9 agonists, alone or in combination with other agents, to treat or prevent diseases in which modulation of TLR9 activity would be beneficial, such as immune diseases, disorders or conditions, viral infections, and cancer.

BACKGROUND

Toll-Like Receptors (TLRs) are a class of pattern recognition receptor (PRR) proteins that play a key role in the innate immune response. TLRs recognize pathogen-associated molecular patterns (PAMPs) from microbial pathogens, such as bacteria, fungi, parasites and viruses, which can be distinguished from host molecules. TLRs are membrane-spanning proteins that typically function as dimers and are expressed by cells involved in the innate immune response, including antigen-presenting dendritic cells and phagocytic macrophages.

There are at least ten human TLR family members, TLR1 to TLR10, and at least twelve murine TLR family members, TLR1 to TLR9 and TLR11 to TLR13, each differing in the types of antigens they recognize. For example, TLR9 is a nucleotide-sensing TLR which is activated by unmethylated cytosine-phosphate-guanosine (CpG) dinucleotides, in which the cytosine is linked to a guanosine by a phosphodiester or phosphorothioate linkage, in single-stranded or double-stranded DNA, including viral DNA.

Activation of TLRs leads to a series of signaling events resulting in the production of type I interferons (IFNs), inflammatory cytokines, and chemokines, and the induction of immune responses. Eventually, this inflammation also activates the adaptive immune system, which then results in the clearance of the invading pathogens and the infected cells.

TLR9 is expressed in B cells and plasmacytoid dendritic cells of the immune system. Binding of CpG-containing DNA to TLR9 initiates a downstream signaling cascade that leads to activation of the transcription factors NF-κB, MAPK and IRF7, which ultimately results in induction of rapid inflammation, characterized by increased expression of various interleukins and cytokines (Yamamoto and Takeda, *Gastroenterology Research and Practice*, vol. 2010). In particular, stimulation of TLR9 by CpG-containing agonists results in increased production of IFN-α, TNF-α, IL-6 and/or IL-1, depending on the class of CpG.

Hepatitis B virus (HBV) is a double stranded DNA (dsDNA) virus that causes diseases including hepatitis B, fibrosis, cirrhosis, and hepatocellular carcinoma. About two billion people are infected with HBV, and almost 400 million people have chronic hepatitis B infection (chronic HBV), characterized by persistent virus and subvirus particles in the blood for more than 6 months (Xu et al., 2014, *Gastrointest Tumors*, 1(3): 135-145). Chronic HBV is currently treated with IFN-α and nucleoside or nucleotide analogs, but there is no ultimate cure due to the persistence of covalently closed circular DNA (cccDNA) in infected hepatocytes. The retained cccDNA plays an ongoing role as a template for viral RNAs and new virions. It is thought that inducing virus-specific B-cell responses through stimulation of the TLR9 signaling pathway on B-cells using synthetic CpG oligodeoxyribonucleotides (CpG ODNs) can effectively eliminate cccDNA-carrying hepatocytes (Isogawa et al., 2005, *J. Virology* 79(11) 7269-7272).

Substantial evidence indicates that immunotherapy is a feasible and effective approach for the treatment of numerous types of cancers. Ligands that target Toll-like receptors and other innate recognition pathways represent a potent strategy for modulating innate immunity to generate antitumor immunity. TLR agonists are currently under investigation as vaccine adjuvants in anticancer therapies for their ability to activate immune cells and promote inflammation (see, e.g., Kaczanowska et al., *J Leukoc Biol.* 2013 June; 93(6): 847-863 and references therein). For example, it was reported that in addition to prolonging CD4$^+$ T cell survival and suppressing T$_{Reg}$ activity, TLR9 ligands increase CD4$^+$ and CD8$^+$ T cell numbers by augmenting IL-2 production and IL-2R expression (Id. and references therein). CpG-ODN stimulation of TLR9 on neuroblastoma cell lines has been shown to decrease cell proliferation and increase caspase-dependent apoptosis, resulting in increased survival of tumor-bearing mice (Id.). However, it was also reported that engagement of TLRs on tumor cells can promote tumor growth by contributing to the maintenance of a chronically inflamed environment, inducing cancer cell proliferation, and promoting cell survival. For example, it was reported that human breast cancer and gastric carcinoma cells expressing TLR9 have enhanced invasive capability as a result of the increased secretion of MMP13 and COX-2 upon TLR9 stimulation in tissue culture, while in the case of glioma, despite its metastasis-inducing properties, TLR9 had no effect on cell proliferation, highlighting the diverse effects that TLR9 signaling can have on different tumor cell types (Id.).

Strategies used to facilitate in vivo delivery of therapeutic oligonucleotides include chemical modification of the oligonucleotide, use of lipid nanocarriers, linking the oligonucleotide to receptor-targeting agents, and the use of small molecules to enhance the effectiveness of the oligonucleotide. However, nanoparticle delivery systems may have limited range of therapeutic applications due to their inability to access most tissues and potential toxicity concerns. In addition, unlike antisense or siRNA, CpG-containing oligonucleotide agonists function by directly binding to the TLR9. Steric hindrance must be avoided when designing conjugate of the CpG-containing oligonucleotide agonists with delivery molecules, such as cholesterol.

Thus, there remains a need for effective therapeutics that can effectively treat or prevent diseases in which modulation of TLR9 activity would be beneficial, such as chronic HBV infections and cancers.

SUMMARY

The present disclosure satisfies the need for effective therapeutics that can effectively treat or prevent diseases in which modulation of TLR9 activity would be beneficial by providing oligodeoxynucleotide (ODN)-based constructs that stimulate an immune response through binding to and activating TLR9. The present disclosure is also directed to the use of these ODN constructs, alone or in combination with other agents, for treating or preventing diseases in which modulation of TLR9 activity would be beneficial, such as immune diseases, disorders or conditions, including viral infections or cancers.

The ODN constructs of the present disclosure comprise CpG oligodeoxynucleotides conjugated, through linkers, to lipid moieties.

The design of the ODN constructs includes, e.g., the number and positioning of cytosine-guanine (CpG) motifs and their internucleotide linkages, as well as the structure and location of lipid moieties and the presence or absence of a linker. Lipid moieties can include lipid molecules, such as cholesterol and tocopherol, that are conjugated to the ODN construct. In addition, the ODN constructs comprise phosphodiester internucleotide linkages within one or more CpG motifs of the oligonucleotide.

ODN constructs according to embodiments of the present disclosure have been shown to achieve an unexpected level of enhanced bioavailability and efficacy as TLR9 agonists. While not wishing to be bound by any particular theory, the enhanced TLR9 agonistic activity can effectively decrease or eliminate HBV cccDNA-carrying hepatocytes by stimulating the re-expression of latent virus while stimulating the immune system to recognize the viral products. In particular, the immune system does not recognize HBV virus in its latent state and the low-level inflammation induced by the disclosed ODN constructs can cause the virus to emerge from that latency. The resulting HBV re-expression and the formation of newly formed viral expression products are then recognized by the activated immune system to control circulating virus and kill the infected cells, effectively eliminating HBV cccDNA-carrying hepatocytes.

The disclosed ODN constructs according to embodiments of the present disclosure can also be used to treat tumors, preferably cancers, such as colorectal cancer. The disclosed CpG ODN constructs induce immunity against tumor cells in vivo and increased survival of tumor-bearing mice.

In one general aspect, the present disclosure relates to CpG ODN constructs having a lipid moiety linked to a CpG ODN through a linker. In an embodiment, the CpG ODN construct has a formula of:

5'$M_1$-$L_1$-[CpG ODN]-$L_2$-$M_2$3',  Formula I:

wherein:

each of $M_1$ and $M_2$ independently represents a lipid moiety, preferably the lipid moiety comprises at least one selected from the group consisting of cholesterol, tocopherol, a palmitoyl group, and a stearyl group, optionally one of $M_1$ and $M_2$ is absent;

each of $L_1$ and $L_2$ independently represents a linker, preferably the linker comprises at least 10 atoms selected from the group consisting of carbon, nitrogen, oxygen, hydrogen, sulfur and phosphorus, and L is covalently linked to the CpG ODN via a cleavable linkage, preferably via an ester or an amide bond, optionally one of $L_1$ and $L_2$ is absent when the respective $M_1$ or $M_2$ is absent; and preferably, CpG ODN comprises at least one CpG motif having a phosphodiester (po) internucleotide linkage;

optionally, the CpG ODN construct of formula (I) is further covalently conjugated to a targeting moiety, which is preferably selected from the group consisting of galactose, N-acetylgalactosamine (GalNAc), fucose, mannose, sialic acid, N-acetyl neuraminic acid.

In one embodiment, the present disclosure relates to a CpG ODN construct having a formula of:

5'M-L-[CpG ODN]3', or  Formula (IIa):

5'[CpG ODN]-L-M3'  Formula (IIb):

wherein:

M represents a lipid moiety, preferably the lipid moiety comprises at least one selected from the group consisting of cholesterol, tocopherol, a palmitoyl group, and a stearyl group;

L represents a linker comprising at least 10 atoms selected from the group consisting of carbon, nitrogen, oxygen, hydrogen, sulfur and phosphorus, and L is covalently linked to the CpG ODN via a cleavable linkage, preferably via an ester or an amide bond; and CpG ODN comprises at least one CpG motif having a po internucleotide linkage, preferably comprises at least two, three or four CpG motifs each having the po internucleotide linkage;

optionally, the CpG ODN construct of Formula (IIa) or (IIb) is further covalently conjugated to a targeting moiety, which is preferably selected from the group consisting of galactose, N-acetylgalactosamine (GalNAc), fucose, mannose, sialic acid, N-acetyl neuraminic acid.

In an embodiment, the linker L in Formula (IIa) or (IIb) comprises —(($CH_2$)$_2$O)$_m$—X)$_n$—, wherein m is an integer from 1 to 15, X is independently a phosphodiester (po) or phosphorothioate (ps) linkage, and n is an integer from 1 to 5.

In another embodiment, the linker L in Formula (IIa) or (IIb) is linked to the lipid moiety M through a phosphodiester (po) linkage or a phosphorothioate (ps) linkage.

In yet another embodiment, the linker L in Formula (IIa) or (IIb) is linked to the CpG ODN via a phosphodiester (po) linkage or a phosphoramidate linkage, preferably a po linkage.

In another aspect, the present disclosure relates to an ODN construct having a structure of:

5'$M_1$-$Y_1$—((($CH_2$)$_2$O)$_m$—X)$_n$—$Y_2$—[CpG ODN]—
$Y_3$-$M_2$3', or  Formula (IIIa):

5'$M_2$-$Y_3$—[CpG ODN]—$Y_2$—((($CH_2$)$_2$O)$_m$—X)$_n$—
$Y_1$-$M_1$3'  Formula (IIIb):

wherein:

$M_1$ represents a lipid moiety, preferably the lipid moiety comprises at least one selected from the group consisting of cholesterol, tocopherol, a palmitoyl group, and a stearyl group, $M_2$ represents a lipid moiety, a targeting moiety, or is absent, $Y_1$ is a bond or a linker, preferably ethylene glycol having the formula (($CH_2$)$_2$O)$_o$, wherein o is 1-15, covalently linked to ((($CH_2$)$_2$O)$_m$—X)$_n$ via a phosphodiester (po) linkage, a phosphorothioate (ps) linkage or a bond, X is independently a bond, a po linkage or a ps linkage,
each of $Y_2$ and $Y_3$ is independently a cleavable linkage, preferably comprises an ester or an amide bond, more preferably comprises a po linkage or a phosphoramidate linkage, most preferably a po linkage, provided that when $M_2$ is absent, $Y_3$ is absent, CpG ODN comprises at least one CpG motif having a po internucleotide linkage, preferably comprises at least two, three or four CpG motifs each having the po internucleotide linkage;

m is an integer from 1 to 15, and n is an integer from 1 to 5.

In one embodiment, the present disclosure relates to a CpG ODN construct having a formula of:

$$5'\text{M-}Y_1\text{—}(((CH_2)_2O)_m\text{—}X)_n\text{—}Y_2\text{—}[\text{CpG ODN}]3', \text{ or Formula (IVa)}:$$

$$5'[\text{CpG ODN}]\text{—}Y_2\text{—}(((CH_2)_2O)_m\text{—}X)_n\text{—}Y_1\text{-M}3' \quad \text{Formula (IVb)}:$$

wherein:

M represents a lipid moiety, preferably the lipid moiety comprises at least one selected from the group consisting of cholesterol, tocopherol, a palmitoyl group, and a stearyl group, $Y_1$ is a bond or a linker, preferably ethylene glycol having the formula $((CH_2)_2O)_o$, wherein o is 1-15, covalently linked to $(((CH_2)_2O)_m\text{—}X)_n$ via a phosphodiester (po) linkage, a phosphorothioate (ps) linkage or a bond, X is independently a bond, a phosphodiester (po) linkage or a phosphorothioate (ps) linkage, $Y_2$ is a cleavable linkage, preferably comprises an ester or an amide bond, more preferably comprises a po linkage or a phosphoramidate linkage, most preferably a po linkage;

CpG ODN comprises at least one CpG motif having a po internucleotide linkage, preferably comprises at least two, three or four CpG motifs each having the po internucleotide linkage;

m is an integer from 1 to 15, preferably 6; and n is an integer from 1 to 5, preferably 2;

optionally, the CpG ODN construct of Formula (IVa) or (IVb) is further covalently conjugated to a targeting moiety, which is preferably selected from the group consisting of galactose, N-acetylgalactosamine (GalNAc), fucose, mannose, sialic acid, N-acetyl neuraminic acid.

According to particular embodiments, the lipid moiety represents a cholesterol, tocopherol or a palmitoyl group.

According to particular embodiments, the CpG ODN in each of Formula (I) to (IVb) has one or more phosphorothioate (ps) internucleotide linkages. According to a more particular aspect, all of the internucleotide linkages of the ODN construct in Formula (I) are phosphorothioate (ps) linkages. According to a particular aspect, at least one of the internucleotide linkages between the C and G of a CpG dinucleotide in the ODN construct is a stereo defined phosphorothioate (ps) internucleotide linkage. According to a particular aspect, at least one of the internucleotide linkages between the C and G of a CpG dinucleotide in the CpG ODN is a phosphodiester (po) internucleotide linkage, and each of the remaining internucleotide linkages of the CpG ODN are phosphorothioate (ps) linkages. According to a particular aspect, the CpG ODN has a length of 19 to 24 nucleotides.

In another general aspect, the present disclosure relates to a pharmaceutical composition comprising an ODN construct of the present disclosure and a pharmaceutically acceptable carrier.

In another general aspect, the present disclosure relates to a method of preparing a pharmaceutical composition of the present disclosure, comprising combining an ODN construct of the present disclosure with a pharmaceutically acceptable carrier.

In another general aspect, the present disclosure relates to a method of stimulating an immune response in a subject in need thereof, comprising administering to the subject a pharmaceutical composition of the present disclosure.

In another general aspect, the present disclosure relates to a method of treating a disease in a subject in need thereof, comprising administering to the subject the pharmaceutical composition of the present disclosure. Preferably, the disease is selected from the group consisting of immune diseases, disorders or conditions, such as viral infections or cancers. More preferably, the disease is chronic HBV infection or a solid tumor cancer.

Other aspects, features and advantages of the present disclosure will be apparent from the following disclosure, including the detailed description present disclosure and its preferred embodiments and the appended claims.

BRIEF DESCRIPTION OF THE DRAWINGS

The foregoing summary, as well as the following detailed description of the present disclosure, will be better understood when read in conjunction with the appended drawings. It should be understood that the present disclosure is not limited to the precise embodiments shown in the drawings.

In the drawings:

FIG. 3 shows activation of human (left panel) and mouse (right panel) TLR9 in reporter cell lines, normalized to ODN2006, by ODN constructs according to embodiments of the present disclosure;

FIG. 13A shows the levels of HBsAg, anti-HBs antibody, and HBV DNA in AAV-HBV mice upon subcutaneous administration of AG9, a ODN construct according to an embodiment of the present disclosure;

FIG. 13B shows the levels of HBsAg, anti-HBs antibody, and HBV DNA in AAV-HBV mice upon intravenous administration of AG9;

FIG. 13C shows the levels of HBsAg, anti-HBs antibody, and HBV DNA in AAV-HBV mice upon intravenous administration of AG19, a ODN construct according to an embodiment of the present disclosure;

FIG. 15A shows the tumor volume in the mice dosed intravenously with the AG1 ODN construct;

FIG. 15B shows the tumor volume in the mice dosed intravenously with the AG9 ODN construct; and FIG. 15C shows the tumor volume in the mice dosed intravenously with the AG17 ODN construct;

FIG. 21A shows that subcutaneous (SQ) administration of AG21 (AG9 conjugated to AlexaFluor-647) to mice resulted in oligo accumulation in draining lymph nodes of the mice as compared to AG20 (AG1 conjugated to AlexaFluor 647);

DETAILED DESCRIPTION

Figure 1:
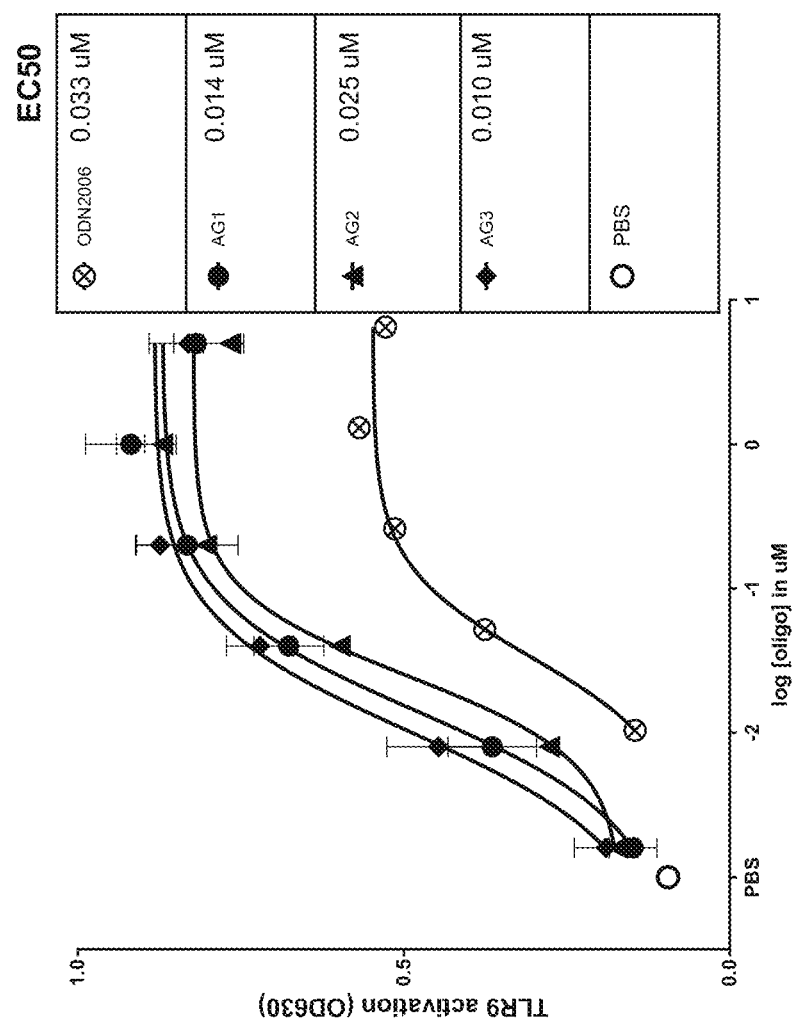
FIG. 1 shows TLR9 activation of a reporter cell line, measured by OD630 level, by TLR9 agonists having phosphodiester-linked CpG motifs at various positions.

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the present disclosure. Such discussion is not an admission that any or all of these matters form part of the prior art with respect to any inventions disclosed or claimed.

Definitions

Unless defined otherwise, all technical and scientific terms used herein have the same meaning commonly understood to one of ordinary skill in the art to which the present disclosure pertains. Otherwise, certain terms used herein have the meanings as set in the specification. All patents, published patent applications and publications cited herein are incorporated by reference as if set forth fully herein. It must be noted that as used herein and in the appended claims, the singular forms "a," "an," and "the" include plural reference unless the context clearly dictates otherwise.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having".

When used herein "consisting of" excludes any element, step, or ingredient not specified in the claim element. When used herein, "consisting essentially of" does not exclude materials or steps that do not materially affect the basic and novel characteristics of the claim. Any of the aforementioned terms of "comprising", "containing", "including", and "having", whenever used herein in the context of an aspect or embodiment of the invention can be replaced with the term "consisting of" or "consisting essentially of" to vary scopes of the disclosure.

As used herein, the term "TLR9" or "Toll like receptor 9", also known as CD289, UNQ5798 or PRO19605, refers to a nucleotide-sensing TLR that is activated by unmethylated cytosine-phosphate-guanine (CpG) dinucleotides. Examples of TLR9 include, but are not limited to, a human TLR9 that is a 1032 amino acid-long protein encoded by an mRNA transcript 3922 nucleotides long (NM_017442.3). The amino acid sequence of the exemplified human TLR9 is represented in GenBank Accession No. NP_059138.1. As used herein, the term "TLR9" includes homologs of TLR9 from species other than human, such as *Macaca Fascicularis* (cynomolgus monkey) or *Pan troglodytes* (chimpanzee). As used herein, the term "TLR9" includes proteins comprising mutations, e.g., point mutations, fragments, insertions, deletions and splice variants of full length wild type TLR9. The term "TLR9" also encompasses post-translational modifications of the TLR9 amino acid sequence.

As used herein, the term "agonist" refers to a molecule that binds to one or more TLRs and induces a receptor mediated response. For example, an agonist can induce, stimulate, increase, activate, facilitate, enhance, or up regulate the activity of the receptor. Such activities are referred to as "agonistic activities." For example, a TLR9 agonist can activate or increase cell signaling through the bound receptor. Agonists include, but are not limited to nucleic acids, small molecules, proteins, carbohydrates, lipids or any other molecules that bind or interact with receptors. Agonists can mimic the activity of a natural receptor ligand. Agonists can be homologous to these natural receptor ligands in respect to sequence, conformation, charge or other characteristics such that they can be recognized by the receptors. This recognition can result in physiologic and/or biochemical changes within the cell, such that the cell reacts to the presence of the agonist in the same manner as if the natural receptor ligand were present. As used herein, the term "TLR9 agonist" refers to any compound that acts as an agonist of TLR9.

As used herein, the terms "induce" and "stimulate" and variations thereof refer to any measurable increase in cellular activity. Induction of a TLR9-mediated cellular activity can include, for example, activation, proliferation, or maturation of a population of immune cells, increasing the production of a cytokine, and/or another indicator of increased immune function. In certain embodiments, induction of an immune response can include increasing the proliferation of B cells, producing antigen-specific antibodies, increasing the proliferation of antigen-specific T cells, improving dendritic cell antigen presentation and/or an increasing expression of certain cytokines, chemokines and co-stimulatory markers.

As used herein, a "lipid moiety" refers to a moiety containing a lipophilic structure. Lipid moieties, such as an alkyl group, a fatty acid, a triglyceride, diglyceride, steroid, sphingolipid, glycolipid or a phospholipid. For example, a lipid moiety can include a sterol such as cholesterol, a methylated chromanol ring with a methylated hydrophobic side chain such as tocopherol, or a saturated fatty acid such as palmitic acid or an ester thereof. Lipid moieties when attached to highly hydrophilic molecules, such as nucleic acids, can substantially enhance plasma protein binding and consequently circulation half-life of the hydrophilic molecules. In addition, binding to certain plasma proteins, such as lipoproteins, has been shown to increase uptake in specific tissues expressing the corresponding lipoprotein receptors (e.g., LDL-receptor HDL-receptor or the scavenger receptor SR-B1). See, e.g., Bijsterbosch, M. K., et al. (2000) *Nucleic Acids Res.* 28, 2717-25; Wolfrum, C., et al. (2007) *Nat Biotechnol* 25:1149-57 25.

A lipid moiety can also be used in combination with a targeting moiety in order to improve the intracellular trafficking of the targeted delivery approach. The targeting moiety can be any suitable moiety or ligand attached directly or indirectly to a CpG ODN of the present disclosure that can direct the ODN construct to in vivo targets such as macromolecules (e.g., receptors), cells (e.g., macrophages, dendritic cells, hepatocytes, tumor cells) or components thereof. Accordingly, a targeting moiety can include any suitable naturally occurring or synthetic molecules such as lipids, lipid acid derivatives, galactose, N-acetylgalactosamine (GalNAc), fucose, mannose, sialic acid, N-acetyl neuraminic acid, antibodies, liposomes, micelles, dendrimers, nanospheres, nanocapsules, peptides, proteins, albumin and hormones.

As used herein, the term "linker" refers to a chemical moiety that joins a nucleotide, such as the 5' or the 3' terminal nucleotide of a CpG ODN, to a lipid moiety or a targeting moiety. The term "cleavable linker" refers to a linker or portion thereof that undergoes cleavage to remove the lipid moiety or the targeting moiety from the nucleotide when desired under certain conditions without altering the nucleotide or the nucleic acid molecule to which it is attached. Depending upon the nature of the linkage, cleavage can be accomplished in vitro or in vivo, for example, by acid or base treatment (e.g. of hydrazone), by enzymatic cleavage (e.g., by nucleases or proteases), by oxidation or reduction of the linkage (e.g. of disulfide bridges), by light treatment (e.g., by photobleaching). According to particular embodiments, the linker comprises any flexible cleavable linker. The linkers include but are not limited to, for example, a covalent bond, a substituted or unsubstituted alkyl, a substituted or unsubstituted heteroalkyl such as polyethylene glycol (PEG), one, two, or three abasic and/or ribitol groups, ethylene glycol moieties, or a peptide. According to embodiments of the present disclosure, the linker is covalently linked to the CpG ODN via a cleavable linkage, such as a phosphodiester (po), phosphoramidate linkage (np) or phosphorothioate (ps) linkage, preferably via an ester or an amide bond, such as a po linkage or an np linkage, most preferably a po linkage. According to embodiments of the present disclosure, the linker comprises ethylene glycol having the formula $((CH_2)_2O)_o$, wherein o is 1-15, covalently linked to the CpG ODN via a po, np, or ps linkage.

In an embodiment, the cleavable linkage such as a po linkage is cleavable by a phosphodiesterase enzyme, such as, e.g., a cyclic nucleotide phosphodiesterase, phospholipases C, phospholipases D, autotaxin, sphingomyelin phosphodiesterase, DNase, RNase, or a restriction endonuclease.

According to embodiments of the present disclosure, a linker comprises $((CH_2)_2O)_m$, wherein m is an integer from 1 to 15, such as 1, 2, 3, 4, 5, 6, 7, 8, 9, 10, 11, 12, 13, 14 or 15. According to particular embodiments, the linker comprises one or more hexaethylene glycol (HEG) moieties having the following molecular formula: $((CH_2)_2O)_6$.

In an embodiment, the linker comprises one or more HEG moieties linked by one or more phosphodiester (po) or phosphorothioate (ps) linkages. In an embodiment, the linker comprises one HEG moiety linked to the CpG ODN via a po linkage. In an embodiment, the linker comprises two HEG moieties linked together by a po linkage and to the CpG ODN via a po linkage.

According to other embodiments, the linker comprises a cleavable disulfide group. According to other embodiments, the linker comprises a protease-cleavable peptide, such as, for example, a peptide linker comprising a cleavage site for a protease specific to a tumor microenvironment, such as uPA, legumain, matriptase, or cathepsin.

According to embodiments of the invention, a lipid moiety (M), such as a cholesterol, tocopherol, a palmitoyl group, or a stearyl group, can be covalently linked to CpG ODN through a linker. The linker can comprise one or more linker moieties such as an ethylene glycol having the formula $((CH_2)_2O)_m$, where m is 1-15. In embodiments, m is 6 and the linker moiety is a hexaethylene glycol (HEG).

According to embodiments of the invention, a lipid moiety (M), such as a cholesterol, tocopherol, a palmitoyl group, or a stearyl group, can be covalently linked to a HEG moiety directly via a bond, or indirectly via a second linker, such as a linker comprising ethylene glycol having the formula $((CH_2)_2O)_o$, wherein o is 1-15. The second linker can be covalently linked to the HEG via a bond, a phosphodiester (po) linkage, phosphoramidate linkage (np) or a phosphorothioate (ps) linkage.

Each linker moiety can be independently linked to the other linker moieties by a linkage such as a linkage selected from the group consisting of phosphodiester (po) linkage, phosphoramidate linkage (np) or a phosphorothioate (ps) linkage. The linker can further be joined to the CpG ODN through a cleavable linkage such as a cleavable linkage selected form the group consisting of a phosphodiester (po) linkage, phosphoramidate linkage (np) and a phosphorothioate (ps) linkage. In embodiments, the linker comprises one linker moiety between the lipid moiety and CpG ODN. In embodiments, the linker comprises two linker moieties between the lipid moiety and CpG ODN. In embodiments, each linker moiety is joined to at least one other linker moiety through a po linkage. In embodiments, each linker moiety is joined to at least one other linker moiety through a ps linkage. In embodiments, each linker moiety is joined to at least one other linker moiety through an np linkage. In embodiments, the linker moiety is covalently linked to the lipid moiety via a second linker, such as a linker comprising ethylene glycol having the formula $((CH_2)_2O)_o$, wherein o is 1-15, and the second linker is covalently lined to the lipid moiety via a bond, a phosphodiester (po) linkage, phosphoramidate linkage (np) or a phosphorothioate (ps) linkage. In embodiments, the linker comprises two linker moieties joined by a po linkage between the lipid moiety and CpG ODN. In embodiments, the linker comprises two linker moieties joined by a ps linkage between the lipid moiety and CpG ODN. In embodiments, the linker comprises two linker moieties joined by an np linkage between the lipid moiety and CpG ODN.

The lipid moiety (M) can be joined to the linker through a bond or linkage such as a linkage selected from the group consisting of phosphodiester (po) linkage, phosphoramidate linkage (np) or a phosphorothioate (ps) linkage. As used herein, "M-po(HEG)" or "(HEG)po-M" means that the lipid moiety M is covalently linked to the HEG moiety directly via a phosphodiester (po) linkage, or indirectly via a second linker, such as a linker comprising ethylene glycol having the formula $((CH_2)_2O)_o$, wherein o is 1-15, and the second linker is covalently linked to the HEG moiety via a phosphodiester (po) linkage. For example, as used herein, "Toco-ps(HEG)" can refer to a tocopherol group covalently linked to CpG ODN via a second linker such as ethylene glycol having the formula $((CH_2)_2O)_o$, wherein o is 1-15, which is covalently linked to a HEG moiety via a phosphodiester (po) linkage.

As used herein, "M-ps(HEG)" or "(HEG)ps-M" means that the lipid moiety M is covalently linked to the HEG moiety directly via a phosphorothioate (ps) linkage, or indirectly via a second linker, such as a linker comprising ethylene glycol having the formula $((CH_2)_2O)_o$, wherein o is 1-15, and the second linker is covalently linked to the HEG moiety via a phosphorothioate (ps) linkage. For example, as used herein, "Toco-ps(HEG)" can refer to a tocopherol group covalently linked to CpG ODN via a second linker such as ethylene glycol having the formula $((CH_2)_2O)_o$, wherein o is 1-15, which is covalently linked to a HEG moiety via a phosphorothioate (ps) linkage.

As used herein, the term "CpG" or "CpG motif" refers to a dinucleotide sequence which contains unmethylated cytosine-guanine (i.e., a cytosine (C) followed by a guanine (G), i.e., 5'-CG-3') linked by a phosphate bond or a phosphorus-containing backbone such as a phosphodiester (po) linkage.

As used herein, "oligonucleotide," "oligodeoxynucleotide" or "ODN" refers to a polynucleotide formed from a plurality of linked nucleotide units. Such oligonucleotides can be obtained from existing nucleic acid sources or can be produced by synthetic methods. In some embodiments, the oligonucleotides each have from about 5 to about 30 nucleotide residues, preferably from about 10 to about 25 nucleotide residues, more preferably from about 19 to about 24 nucleotide residues. In an embodiment, the ODN contains 19 nucleotide residues. In an embodiment, the ODN contains 20 nucleotide residues. In an embodiment, the ODN contains 21 nucleotide residues. In an embodiment, the ODN contains 22 nucleotide residues. In an embodiment, the ODN contains 23 nucleotide residues. In an embodiment, the ODN contains 24 nucleotide residues. ODNs of the present disclosure can be obtained from existing nucleic acid sources (e.g. genomic or cDNA) but are preferably synthetic (e.g. produced by oligonucleotide synthesis).

As used herein, "nucleotide" includes any native or naturally occurring nucleotides, which include a nitrogenous base selected from the group consisting of adenine (A), thymidine (T), cytosine (C), guanine (G) and uracil (U), a deoxyribose sugar, and a phosphate group. Exemplary nucleotides include, but are not limited to, naturally occurring nucleotide bases, e.g., adenine, guanine, cytosine, uracil, and thymine.

As used herein, the terms "CpG oligonucleotide," "CpG oligodeoxynucleotide" and "CpG ODN" are used interchangeably and refer to an oligonucleotide comprising at least one CpG motif. CpG ODNs of the present disclosure can include one or more classes of CpG ODNs, such as a class A, class B, class C or class P ODN, as described in Bode et al., 2011, *Expert Rev Vaccines*, 10(4): 499-511. Class A CpG ODNs, also referred to as D-type, contain a central CpG-containing palindromic motif and poly-G motifs at the 5' and/or 3' ends. Class B CpG ODNs, also referred to as K-type, are typically fully stabilized by a full phosphorothioate backbone and include one or more CpG dinucleotides within certain preferred base contexts. Class C CpG ODNs are typically fully stabilized by a full phosphorothioate backbone and include a central palindromic CpG motif as well as other CpG dinucleotides. Class P CpG ODNs are typically fully stabilized by a full phosphorothioate backbone and include two palindromes and multiple CpG dinucleotides.

As used herein, the term "internucleotide linkage" refers to a chemical linkage to join two adjacent nucleotides through their sugars consisting of a phosphorous atom and a charged or neutral group between adjacent nucleosides. Examples of internucleotide linkages include phosphodiester (po), phosphorothioate (ps), phosphoramidate (np), phosphorodithioate (ps2), methylphosphonate (mp), and methylphosphorothioate (rp). Phosphorothioate, phosphoramidate, phosphorodithioate, methylphosphonate and methylphosphorothioate are stabilizing internucleotide linkages, while phosphodiester is a naturally-occurring internucleotide linkage.

Oligonucleotide phosphorothioates are typically synthesized as a random racemic mixture of Rp and Sp phosphorothioate linkages. However, according to particular embodiments, the phosphorothioate linkages of the disclosed ODN constructs contain a mixture of Rp and Sp phosphorothioate linkages. According to particular embodiments, the CpG ODN of the ODN construct has a stereo-defined ps internucleotide linkage, i.e. the ps linkage is either Rp or Sp in at least 75%, such as at least 80%, or at least 85%, or at least 90%, or at least 95%, such as at least 99% of the oligonucleotide molecules present in the CpG ODN.

According to particular embodiments, one to four, preferably three or four, of the CpG dinucleotides in the CpG ODN each have a phosphodiester (po) internucleotide linkage, and each of the remaining internucleotide linkages of the CpG ODN are phosphorothioate internucleotide linkages. In embodiments, each of the CpG dinucleotides in the CpG ODN have a phosphodiester (po) internucleotide linkage, and each of the remaining nucleotides in the CpG ODN have a phosphorothioate (ps) internucleotide linkage.

As used herein, the term "carrier" refers to any excipient, diluent, filler, salt, buffer, stabilizer, solubilizer, oil, lipid, lipid containing vesicle, microsphere, liposomal encapsulation, or other material well known in the art for use in pharmaceutical formulations. It will be understood that the characteristics of the carrier, excipient or diluent will depend on the route of administration for a particular application. As used herein, the term "pharmaceutically acceptable carrier" refers to a non-toxic material that does not interfere with the effectiveness of a composition according to the present disclosure or the biological activity of a composition according to the present disclosure. According to particular embodiments, in view of the present disclosure, any pharmaceutically acceptable carrier suitable for use in a CpG ODN-based agonist pharmaceutical composition can be used in the present disclosure.

As used herein, the term "subject" refers to an animal. According to particular embodiments, the subject is a mammal including a non-primate (e.g., a camel, donkey, zebra, cow, pig, horse, goat, sheep, cat, dog, rat, rabbit, guinea pig or mouse) or a primate (e.g., a monkey, chimpanzee, or human). In particular embodiments, the subject is a human.

As used herein, the term "therapeutically effective amount" refers to an amount of an active ingredient or component that elicits the desired biological or medicinal response in a subject. A therapeutically effective amount can be determined empirically and in a routine manner, in relation to the stated purpose. For example, in vitro assays can optionally be employed to help identify optimal dosage ranges. Selection of a particular effective dose can be determined (e.g., via clinical trials) by those skilled in the art based upon the consideration of several factors, including the disease to be treated or prevented, the symptoms involved, the patient's body mass, the patient's immune status and other factors known by the skilled artisan. The precise dose to be employed in the formulation will also depend on the route of administration, and the severity of disease, and should be decided according to the judgment of the practitioner and each patient's circumstances. Effective doses can be extrapolated from dose-response curves derived from in vitro or animal model test systems.

As used herein, the terms "treat," "treating," and "treatment" are all intended to refer to an amelioration or reversal of at least one measurable physical parameter related to a disease in which modulation of TLR9 activity would be beneficial, such as an immune disease, disorder or condition, which is not necessarily discernible in the subject, but can be discernible in the subject. The terms "treat," "treating," and "treatment," can also refer to causing regression, preventing the progression, or at least slowing down the progression of the disease, disorder, or condition. In a particular embodiment, "treat," "treating," and "treatment" refer to an alleviation, prevention of the development or onset, or reduction in the duration of one or more symptoms associated with the disease in which modulation of TLR9 activity would be beneficial such as an immune disease, disorder or condition, including a viral infection or a cancer. In a particular embodiment, "treat," "treating," and "treatment" refer to prevention of the recurrence of the disease, disorder, or condition. In a particular embodiment, "treat," "treating," and "treatment" refer to an increase in the survival of a subject having the disease, disorder, or condition. In a particular embodiment, "treat," "treating," and "treatment" refer to elimination of the disease, disorder, or condition in the subject.

As used herein a "disease in which modulation of TLR9 activity would be beneficial" include diseases in which stimulation of TLR9 signaling would benefit the subject. For example, a disease in which modulation of TLR9 activity would be beneficial can include immune diseases, disorders or conditions. According to particular embodiments, the disease, disorder or condition to be treated is a cancer, an inflammatory disease, disorder or condition, an autoimmune disease, disorder or condition, or a disease, disorder or condition caused by a pathogen, such as a viral infection.

According to particular embodiments, the viral infection is an RNA or DNA virus such as adenovirus, cytomegalovirus, hepatitis A virus (HAV), hepadnaviruses including HBV, chronic HBV, flaviviruses including Yellow Fever virus, hepaciviruses including hepatitis C virus (HCV), herpes simplex type 1 and 2, herpes zoster, human herpesvirus 6, human immunodeficiency virus (HIV), human papilloma virus (HPV), influenza A virus, influenza B virus, measles, parainfluenza virus, pestivirus, poliovirus, poxvirus, rhinovirus, coronavirus, respiratory syncytial virus (RSV), multiple families of viruses that cause hemorrhagic fevers, including the Arenaviruses, the Bunyaviruses and Filoviruses, and a range of viral encephalitides caused by RNA and DNA viruses.

According to particular embodiments, the cancer or tumor is a solid tumor or blood cancer. According to particular embodiments, the cancer or tumor is a carcinoma, sarcoma, melanoma, lymphoma, or leukemia. According to particular embodiments, the cancer or tumor is a carcinoma, a sarcoma, a leukemia, or a cancer caused by a virus. According to particular embodiments, the cancer is a mammary, colon, bladder, lung, prostate, stomach, or pancreas carcinoma or a lymphoblastic or myeloid leukemia.

As used herein, the term "in combination," in the context of the administration of two or more therapies to a subject, refers to the use of more than one therapy. The use of the term "in combination" does not restrict the order in which therapies are administered to a subject or the time between such administration. For example, a first therapy (e.g., a composition described herein) can be administered prior to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject.

ODN Constructs

In an embodiment, the CpG ODN construct has a formula of:

$$5'M_1\text{-}L_1\text{-}[\text{CpG ODN}]\text{-}L_2\text{-}M_23', \qquad \text{Formula I:}$$

wherein:

each of $M_1$ and $M_2$ independently represents a lipid moiety, preferably the lipid moiety comprises at least one lipid moiety selected from the group consisting of cholesterol, tocopherol, a palmitoyl group, and a stearyl group, optionally one of $M_1$ and $M_2$ is absent;

each of $L_1$ and $L_2$ independently represents a linker, preferably the linker comprises at least 10 atoms selected from the group consisting of carbon, nitrogen, oxygen, hydrogen, sulfur and phosphorus, and L is covalently linked to the CpG ODN via a cleavable linkage, preferably via an ester or an amide bond, optionally one of $L_1$ and $L_2$ is absent when the respective $M_1$ or $M_2$ is absent; and preferably, CpG ODN comprises at least one CpG motif having a phosphodiester (po) internucleotide linkage.

In one embodiment, the present disclosure relates to a CpG ODN construct having a formula of:

5'M-L-[CpG ODN]3', or            Formula (IIa):

5'[CpG ODN]-L-M3'            Formula (IIb):

wherein:

M represents a lipid moiety, preferably the lipid moiety comprises at least one selected from the group consisting of cholesterol, tocopherol, a palmitoyl group, and a stearyl group;

L represents a linker comprising at least 10 atoms selected from the group consisting of carbon, nitrogen, oxygen, hydrogen, sulfur and phosphorus, and L is covalently linked to the CpG ODN via a cleavable linkage, preferably via an ester or an amide bond; and CpG ODN comprises at least one CpG motif having a po internucleotide linkage, preferably comprises at least two, three or four CpG motifs each having the po internucleotide linkage.

According to particular aspects, the linker L comprises 5-100 atoms, more preferably 20-80 atoms, 20-40 atoms, or 30-60 atoms in length selected from the group consisting of carbon, nitrogen, oxygen, hydrogen, sulfur and phosphorus. According to particular aspects, the linker comprises a phosphodiester (po) or phosphorothioate (ps) linkage, and comprises $((CH_2)_2O)_m$, wherein m is an integer from 1 to 15, preferably 5 to 10, more preferably 6.

In an embodiment, the linker L in Formula (IIa) or (IIb) comprises —$((CH_2)_2O)_m$—$X)_n$—, wherein m is an integer from 1 to 15, such as 1, 2, 3, 4, 5, 6, 7, 8, 9, 10, 11, 12, 13, 14 or 15, X is independently a phosphodiester (po) or phosphorothioate (ps) linkage, and n is an integer from 1 to 5, such as 1, 2, 3, 4, or 5.

In another embodiment, the linker L in Formula (IIa) or (IIb) is linked to the lipid moiety M through a phosphodiester (po) linkage or a phosphorothioate (ps) linkage.

In yet another embodiment, the linker L in Formula (IIa) or (IIb) is linked to the CpG ODN via a phosphodiester (po) linkage or a phosphoramidate linkage, preferably a po linkage.

In an embodiment, L is —$Y_1$—$(((CH_2)_2O)_m$—$X)_n$—$Y_2$—; or L is —$Y_2$—$(((CH_2)_2O)_m$—$X)_n$—$Y_1$—, wherein, $Y_1$ is a bond or a linker, preferably ethylene glycol having the formula $((CH_2)_2O)_o$, wherein o is 1-15, covalently linked to $(((CH_2)_2O)_m$—$X)_n$ via a phosphodiester (po) linkage, a phosphorothioate (ps) linkage or a bond;

$Y_2$ is a cleavable linkage comprising an ester or an amide bond;

each X is independently a bond, a po linkage or a ps linkage;

m is an integer from 1 to 15; and n is an integer from 1 to 5.

In embodiments, $Y_2$ is a po linkage or an np linkage.

In another aspect, the present disclosure relates to an ODN construct having a structure of:

5'$M_1$-$Y_1$—$(((CH_2)_2O)_m$—$X)_n$—$Y_2$—[CpG ODN]—$Y_3$-$M_2$3', or            Formula (IIIa):

5'$M_2$-$Y_3$—[CpG ODN]—$Y_2$—$(((CH_2)_2O)_m$—$X)_n$—$Y_1$-$M_1$3'            Formula (IIIb):

wherein:

$M_1$ represents a lipid moiety, preferably the lipid moiety comprises at least one selected from the group consisting of cholesterol, tocopherol, a palmitoyl group, and a stearyl group, $M_2$ represents a lipid moiety, a targeting moiety, or is absent, $Y_1$ is a bond or a linker, preferably ethylene glycol having the formula $((CH_2)_2O)_o$, wherein o is 1-15, covalently linked to $(((CH_2)_2O)_m$—$X)_n$ via a phosphodiester (po) linkage, a phosphorothioate (ps) linkage or a bond, X is independently a bond, a po linkage or a ps linkage, each of $Y_2$ and $Y_3$ is independently a cleavable linkage, preferably comprises an ester or an amide bond, more preferably comprises a po linkage or a phosphoramidate linkage, most preferably a po linkage, provided that when $M_2$ is absent, $Y_3$ is absent, CpG ODN comprises at least one CpG motif having a po internucleotide linkage, preferably comprises at least two, three or four CpG motifs each having a po internucleotide linkage;

m is an integer from 1 to 15, and n is an integer from 1 to 5.

In one embodiment, the present disclosure relates to a CpG ODN construct having a formula of:

5'M-$Y_1$—$(((CH_2)_2O)_m$—$X)_n$—$Y_2$—[CpG ODN]3', or Formula (IVa):

5'[CpG ODN]—$Y_2$—$(((CH_2)_2O)_m$—$X)_n$—$Y_1$-M3'      Formula (IVb):

wherein:

M represents a lipid moiety, preferably the lipid moiety comprises at least one selected from the group consisting of cholesterol, tocopherol, a palmitoyl group, and a stearyl group, $Y_1$ is a bond or a linker, preferably 1-5 elthylene glycol moieties, covalently linked to $(((CH_2)_2O)_m$—$X)_n$ via a phosphodiester (po) linkage, a phosphorothioate (ps) linkage or a bond, X is independently a bond, a phosphodiester (po) linkage or a phosphorothioate (ps) linkage, $Y_2$ is a cleavable linkage, preferably comprises an ester or an amide bond, more preferably comprises a po linkage or a phosphoramidate linkage, most preferably a po linkage;

CpG ODN comprises at least one CpG motif having a po internucleotide linkage, preferably comprises at least two, three or four CpG motifs each having the po internucleotide linkage;

m is an integer from 1 to 15, preferably 6; and n is an integer from 1 to 5, preferably 2;

optionally, the CpG ODN construct of Formula (IVa) or (IVb) is further covalently conjugated to a targeting moiety, which is preferably selected from the group consisting of galactose, N-acetylgalactosamine (GalNAc), fucose, mannose, sialic acid, N-acetyl neuraminic acid.

According to a particular embodiment, X is independently a phosphodiester (po) linkage or absent, Y is a po linkage, m is 6, n is 2, M represents a lipid moiety comprising a tocopherol or a palmitoyl group.

According to a particular embodiment, the ODN construct has a structure selected from the group consisting of:
5' M-po(HEG)po(HEG)po-[CpG ODN] 3';
5' M-ps(HEG)po(HEG)po-[CpG ODN] 3',
5' M-ps(HEG)ps(HEG)po-[CpG ODN] 3',
5' M-po(HEG)ps(HEG)po-[CpG ODN] 3',
5' [CpG ODN]-po(HEG)po(HEG)po-M 3',
5' [CpG ODN]-po(HEG)ps(HEG)po-M 3',
5' [CpG ODN]-po(HEG)ps(HEG)ps-M 3', and
5' [CpG ODN]-po(HEG)po(HEG)ps-M 3',
wherein:
M represents a lipid moiety comprising at least one selected from the group consisting of cholesterol, tocopherol, a palmitoyl group, and a stearyl group;
po represents a phosphodiester linkage;
HEG represents $((CH_2)_2O)_6$;
ps represents a phosphorothioate linkage; and
CpG ODN comprises at least one CpG motif having a po internucleotide linkage, preferably comprises at least two, three or four CpG motifs each having the po internucleotide linkage,
wherein M is covalently linked to (HEG) directly via a po or ps linkage, or indirectly via a second linker that is linked to (HEG) directly via a po or ps linkage.

According to a particular embodiment, the ODN construct has a structure selected from the group consisting of:
5' Toco-po(HEG)po(HEG)po-[CpG ODN] 3', wherein Toco represents tocopherol,
5' Chol-po(HEG)po(HEG)po-[CpG ODN] 3', wherein Cho represents cholesterol,
5' Palm-po(HEG)po(HEG)po-[CpG ODN] 3', wherein Palm represents a palmitoyl group,
5' [CpG ODN]-po(HEG)ps-Chol 3', wherein Chol represents cholesterol,
5' [CpG ODN]-po(HEG)ps-Toco 3', wherein Toco represents tocopherol, and
5' [CpG ODN]-po(HEG)ps-Palm 3', wherein Palm represents a palmitoyl group,
wherein:
po represents a phosphodiester linkage;
HEG represents $((CH_2)_2O)_6$;
ps represents a phosphorothioate linkage; and
CpG ODN comprises at least one CpG motif having a po internucleotide linkage, preferably comprises at least two, three or four CpG motifs each having the po internucleotide linkage,
wherein the tocopherol, the cholesterol, or the palmitoyl group is covalently linked to the (HEG) directly via a po or ps linkage, or indirectly via a second linker that is linked to (HEG) directly via a po or ps linkage.

In an embodiment, the CpG ODN contains a number of CpG dinucleotides suitable to activate TLR9. In an embodiment, the CpG ODN contains at least one CpG dinucleotide. In an embodiment, the CpG ODN contains at least two CpG dinucleotides. In an embodiment, the CpG ODN contains at least three CpG dinucleotides. In an embodiment, the CpG ODN contains at least four CpG dinucleotides. In an embodiment, the CpG ODN contains one CpG dinucleotide. In an embodiment, the CpG ODN contains two CpG dinucleotides. In an embodiment, the CpG ODN contains three CpG dinucleotides. In an embodiment, the CpG ODN contains four CpG dinucleotides.

In an embodiment, the CpG dinucleotides of the CpG ODN are positioned within the CpG ODN to activate TLR9. In an embodiment, a first CpG dinucleotide of the CpG ODN is separated from a second CpG dinucleotide by at least one nucleotide. In an embodiment, a first CpG dinucleotide of the CpG ODN is separated from a second CpG dinucleotide by at least two nucleotides. In an embodiment, a first CpG dinucleotide of the CpG ODN is separated from a second CpG dinucleotide by at least three nucleotides. In an embodiment, a first CpG dinucleotide of the CpG ODN is separated from a second CpG dinucleotide by at least four nucleotides. In an embodiment, a first CpG dinucleotide of the CpG ODN is separated from a second CpG dinucleotide by at least five nucleotides. In an embodiment, a first CpG dinucleotide of the CpG ODN is separated from a second CpG dinucleotide by at least six nucleotides. In an embodiment, a first CpG dinucleotide of the CpG ODN is separated from a second CpG dinucleotide by one nucleotide. In an embodiment, a first CpG dinucleotide of the CpG ODN is separated from a second CpG dinucleotide by two nucleotides. In an embodiment, a first CpG dinucleotide of the CpG ODN is separated from a second CpG dinucleotide by three nucleotides. In an embodiment, a first CpG dinucleotide of the CpG ODN is separated from a second CpG dinucleotide by four nucleotides. In an embodiment, a first CpG dinucleotide of the CpG ODN is separated from a second CpG dinucleotide by five nucleotides. In an embodiment, a first CpG dinucleotide of the CpG ODN is separated from a second CpG dinucleotide by six nucleotides.

In an embodiment, a CpG dinucleotide is separated from the 3' end of the CpG ODN by at least one nucleotide. In an embodiment, a CpG dinucleotide is separated from the 3' end of the CpG ODN by at least two nucleotides. In an embodiment, a CpG dinucleotide is separated from the 3' end of the CpG ODN by at least three nucleotides. In an embodiment, a CpG dinucleotide is separated from the 3' end of the CpG ODN by at least four nucleotides. In an embodiment, a CpG dinucleotide is separated from the 3' end of the CpG ODN by at least five nucleotides. In an embodiment, a CpG dinucleotide is separated from the 3' end of the CpG ODN by one nucleotide. In an embodiment, a CpG dinucleotide is separated from the 3' end of the CpG ODN by two nucleotides. In an embodiment, a CpG dinucleotide is separated from the 3' end of the CpG ODN by three nucleotides. In an embodiment, a CpG dinucleotide is separated from the 3' end of the CpG ODN by four nucleotides. In an embodiment, a CpG dinucleotide is separated from the 3' end of the CpG ODN by five nucleotides.

In an embodiment, a CpG dinucleotide is separated from the 5' end of the CpG ODN by at least one nucleotide. In an embodiment, a CpG dinucleotide is separated from the 5' end of the CpG ODN by at least two nucleotides. In an embodiment, a CpG dinucleotide is separated from the 5' end of the CpG ODN by at least three nucleotides. In an embodiment, a CpG dinucleotide is separated from the 5' end of the CpG ODN by at least four nucleotides. In an embodiment, a CpG dinucleotide is separated from the 5' end of the CpG ODN by at least five nucleotides. In an embodiment, a CpG dinucleotide is separated from the 5' end of the CpG ODN by one nucleotide. In an embodiment, a CpG dinucleotide is separated from the 5' end of the CpG ODN by two nucleotides. In an embodiment, a CpG dinucleotide is separated from the 5' end of the CpG ODN by three nucleotides. In an embodiment, a CpG dinucleotide is separated from the 5' end of the CpG ODN by four nucleotides. In an embodiment, a CpG dinucleotide is separated from the 5' end of the CpG ODN by five nucleotides.

According to particular aspects, the CpG ODN of the ODN construct has a phosphorothioate (ps) internucleotide linkage. According to particular aspects, the CpG ODN of the ODN construct has a stereodefined phosphorothioate (ps) internucleotide linkage. According to particular aspects, one to four, preferably three or four of the CpG dinucleotides in the CpG ODN of the ODN construct each have a phosphodiester (po) internucleotide linkage, and each of the remaining internucleotide linkages of the CpG ODN are phosphorothioate (ps) internucleotide linkages. According to other particular aspects, two of the internucleotide linkages in the CpG ODN each have a phosphodiester (po) internucleotide linkage, and each of the remaining internucleotide linkages of the CpG ODN are phosphorothioate (ps) linkages. According to other particular aspects, three of the internucleotide linkages in the CpG ODN each have a phosphodiester (po) internucleotide linkage, and each of the remaining internucleotide linkages of the CpG ODN are phosphorothioate (ps) linkages. According to other particular aspects, four of the internucleotide linkages in the CpG ODN each have a phosphodiester (po) internucleotide linkage, and each of the remaining internucleotide linkages of the CpG ODN are phosphorothioate (ps) linkages. According to yet other particular aspects, five or more of the internucleotide linkages in the CpG ODN each have a phosphodiester (po) internucleotide linkage, and each of the remaining internucleotide linkages of the CpG ODN are phosphorothioate (ps) linkages.

According to some embodiments, an ODN construct of the present disclosure comprises a TLR9 agonist comprising a CpG ODN comprising, preferably consisting of a polynucleotide sequence selected from the group consisting of:

```
                                        (SEQ ID NO: 1)
5' TCGTCGTTTTGTCGTTTTGTCGTT 3';

(SEQ ID NO: 2)
5' GGGGGACGATCGTCGGGGGG 3';

(SEQ ID NO: 3)
5' GGGGTCAACGTTGAGGGGGG 3';

(SEQ ID NO: 4)
5' TCCATGACGTTCCTGACGTT 3';

(SEQ ID NO: 5)
5' TCGTCGTTTTCGGCGCGCGCCG 3';

(SEQ ID NO: 6)
5' TCGTCGTTACGTAACGACGACGTT 3';
and
                                        (SEQ ID NO: 7)
5' TCGTCGTTTTGTCGTTTTGTCGT 3'.
```

According to some embodiments, an ODN construct of the present disclosure comprises a TLR9 agonist comprising a CpG ODN comprising, preferably consisting of a polynucleotide sequence that is, or is at least, 70%, 75%, 80%, 85%, 90%, 91%, 92%, 93%, 94%, 95%, 96%, 97%, 98%, 99% or 100% identical, or any percentage between such values, to one of SEQ ID NOs: 1-7.

According to particular aspects, an ODN construct of the present disclosure comprises a CpG ODN comprising, preferably consisting of a polynucleotide sequence selected from the group consisting of:

```
                                             (SEQ ID NO: 8)
(1)  5' TpsCpoGpsTpsCpoGpsTpsTpsTpsTpsGpsTpsCpoGps
        TpsTpsTpsTpsGpsTpsCpoGpsTpsT 3';

(SEQ ID NO: 9)
(2)  5' TpsCpsGpsTpsCpoGpsTpsTpsTpsTpsGpsTpsCpsGps
        TpsTpsTpsTpsGpsTpsCpsGpsTpsT 3';

(SEQ ID NO: 10)
(3)  5' TpsCpsGpsTpsCpoGpsTpsTpsTpsTpsGpsTpsCpoGps
        TpsTpsTpsTpsGpsTpsCpsGpsTpsT 3';

(SEQ ID NO: 11)
(4)  5' TpsCpsGpsTpsCpsGpsTpsTpsTpsTpsGpsTpsCpoGps
        TpsTpsTpsTpsGpsTpsCpsGpsTpsT 3';

(SEQ ID NO: 12)
(5)  5' TpsCpsGpsTpsCpsGpsTpsTpsTpsTpsGpsTpsCpsGps
        TpsTpsTpsTpsGpsTpsCpoGpsTpsT 3';

(SEQ ID NO: 13)
(6)  5' TpsCpsGpsTpsCpsGpsTpsTpsTpsTpsGpsTpsCpoGps
        TpsTpsTpsTpsGpsTpsCpoGpsTpsT 3';

(SEQ ID NO: 14)
(7)  5' TpsCpsGpsTpsCpoGpsTpsTpsTpsTpsGpsTpsCpoGps
        TpsTpsTpsTpsGpsTpsCpoGpsTpsT 3';

(SEQ ID NO: 15)
(8)  5' TpsCpsGpsTpsCpsGpsTpsTpsApsCpsGpsTpsApsAps
        CpsGpsApsCpsGpsApsCpsGpsTpsT 3';

(SEQ ID NO: 16)
(9)  5' TpsCpsGpsTpsCpoGpsTpsTpsApsCpsGpsTpsApsAps
        CpsGpsApsCpsGpsApsCpsGpsTpsT 3';

(SEQ ID NO: 17)
(10) 5' TpsCpsGpsTpsCpoGpsTpsTpsApsCpoGpsTpsApsAps
        CpsGpsApsCpsGpsApsCpsGpsTpsT 3';

(SEQ ID NO: 18)
(11) 5' TpsCpsGpsTpsCpoGpsTpsTpsApsCpoGpsTpsApsAps
        CpoGpsApsCpsGpsApsCpsGpsTpsT 3';

(SEQ ID NO: 19)
(12) 5' TpsCpsGpsTpsCpoGpsTpsTpsApsCpoGpsTpsApsAps
        CpoGpsApsCpoGpsApsCpsGpsTpsT 3';

(SEQ ID NO: 20)
(13) 5' GpsGpsGpsGpsGpsApsCpoGpsApsTpsCpoGpsTpsCpo
        GpsGpsGpsGpsGpsG 3';

(SEQ ID NO: 21)
(14) 5' GpsGpsGpsGpsTpsCpsApsApsCpoGpsTpsTpsGpsAps
        GpsGpsGpsGpsGpsG 3';

(SEQ ID NO: 22)
(15) 5' TpsCpsCpsApsTpsGpsApsCpsGpsTpsTpsCpsCpsTps
        GpsApsCpsGpsTpsT 3';

(SEQ ID NO: 23)
(16) 5' TpsCpsGpsTpsCpsGpsTpsTpsTpsTpsCpsGpsGpsCps
        GpsCpsGpsCpsGpsCpsCpsG3';

(SEQ ID NO: 24)
(17) 5' TpsCpoGpsTpsCpsGpsTpsTpsTpsTpsGpsTpsCpsGps
        TpsTpsTpsTpsGpsTpsCpsGpsT 3';

(SEQ ID NO: 25)
(18) 5' TpsCpoGpsTpsCpoGpsTpsTpsTpsTpsGpsTpsCpsGps
        TpsTpsTpsTpsGpsTpsCpsGpsT 3';
and
                                             (SEQ ID NO: 26)
(19) 5' TpsCpoGpsTpsCpoGpsTpsTpsTpsTpsGpsTpsCpoGps
        TpsTpsTpsTpsGpsTpsCpsGpsT 3';
``` wherein:
po represents a phosphodiester internucleotide linkage; and
ps represents a phosphorothioate internucleotide linkage.

According to some embodiments, an ODN construct of the present disclosure comprises a TLR9 agonist comprising a CpG ODN comprising, preferably consisting of a polynucleotide sequence that is, or is at least, about 70%, 75%, 80%, 85%, 90%, 91%, 92%, 93%, 94%, 95%, 96%, 97%, 98%, 99% or 100% identical, or any percentage between such values, to one of SEQ ID NOs: 8-26.

According to particular aspects, an ODN construct of the present disclosure comprises a structure selected from the group consisting of:

(1) 5' Toco-po(HEG)po(HEG)po-TpsCpoGpsTpsCpoGps
TpsTpsTpsTpsGpsTpsCpoGpsTpsTpsTpsTpsGpsTps
CpoGpsTpsT 3'; (SEQ ID NO: 27)

(2) 5' Toco-po(HEG)po(HEG)po-TpsCpsGpsTpsCpoGps
TpsTpsTpsTpsGpsTpsCpoGpsTpsTpsTpsTpsGpsTps
CpsGpsTpsT 3'; (SEQ ID NO: 28)

(3) 5' TpsCpoGpsTpsCpoGpsTpsTpsTpsTpsGpsTpsCpo
GpsTpsTpsTpsTpsGpsTpsCpoGpsTpsT-
(HEG)po(HEG)po-Toco 3'; (SEQ ID NO: 29)

(4) 5' TpsCpsGpsTpsCpoGpsTpsTpsTpsTpsGpsTpsCpo
GpsTpsTpsTpsTpsGpsTpsCpsGpsTpsT-
(HEG)po(HEG)po-Toco 3'; (SEQ ID NO: 30)

(5) 5' Chol-po(HEG)po(HEG)po-TpsCpoGpsTpsCpoGps
TpsTpsTpsTpsGpsTpsCpoGpsTpsTpsTpsTpsGpsTps
CpoGpsTpsT 3'; (SEQ ID NO: 31)

(6) 5' Chol-po(HEG)po(HEG)poTpsCpsGpsTpsCpsGps
TpsTpsTpsTpsGpsTpsCpsGpsTpsTpsTpsTpsGpsTps
CpsGpsTpsT 3'; (SEQ ID NO: 32)

(7) 5' Chol-po(HEG)po(HEG)po-TpsCpoGpsTpsCpsGps
TpsTpsTpsTpsGpsTpsCpsGpsTpsTpsTpsTpsGpsTps
CpsGpsTpsT 3'; (SEQ ID NO: 33)

(8) 5' Chol-po(HEG)po(HEG)po-TpsCpoGpsTpsCpoGps
TpsTpsTpsTpsGpsTpsCpsGpsTpsTpsTpsTpsGpsTps
CpsGpsTpsT 3'; (SEQ ID NO: 34)

(9) 5' Chol-po(HEG)po(HEG)po-TpsCpoGpsTpsCpoGps
TpsTpsTpsTpsGpsTpsCpoGpsTpsTpsTpsTpsGpsTps
CpsGpsTpsT 3'; (SEQ ID NO: 35)

(10) 5' Chol-po(HEG)po(HEG)po-TpsCpoGpsTpsCpoGps
TpsTpsTpsTpsGpsTpsCpoGpsTpsTpsTpsTpsGpsTps
CpoGpsTpsT 3'; (SEQ ID NO: 36)

(11) 5' TpsCpsGpsTpsCpsGpsTpsTpsTpsTpsGpsTpsCps
GpsTpsTpsTpsTpsGpsTpsCpsGpsTpsTps-
(HEG)po(HEG)po-Chol 3'; (SEQ ID NO: 37)

(12) 5' TpsCpoGpsTpsCpsGpsTpsTpsTpsTpsGpsTpsCps
GpsTpsTpsTpsTpsGpsTpsCpsGpsTpsTps-
(HEG)po(HEG)po-Chol 3'; (SEQ ID NO: 38)

(13) 5' TpsCpoGpsTpsCpoGpsTpsTpsTpsTpsGpsTpsCps
GpsTpsTpsTpsTpsGpsTpsCpsGpsTpsTps-
(HEG)po(HEG)po-Chol 3'; (SEQ ID NO: 39)

(14) 5' TpsCpoGpsTpsCpoGpsTpsTpsTpsTpsGpsTpsCpo
GpsTpsTpsTpsTpsGpsTpsCpoGpsTpsTps-
(HEG)po(HEG)po-Chol 3'; (SEQ ID NO: 40)

(15) 5' TpsCpsGpsTpsCpsGpsTpsTpsTpsTpsGpsTpsCps
GpsTpsTpsTpsTpsGpsTpsCpsGpsTpsTps-
(HEG)po(HEG)po-Toco 3'; (SEQ ID NO: 41)

(16) 5' Toco-po(HEG)po(HEG)po-TpsCpoGpsTpsCpoGps
TpsTpsTpsTpsGpsTpsCpoGpsTpsTpsTpsTpsGpsTps
CpoGpsTpsT 3'; (SEQ ID NO: 42)

(17) 5' TpsCpoGpsTpsCpsGpsTpsTpsTpsTpsGpsTpsCps
GpsTpsTpsTpsTpsGpsTpsCpsGpsTpsTps-
(HEG)po(HEG)po-Toco 3'; (SEQ ID NO: 43)

(18) 5' TpsCpoGpsTpsCpoGpsTpsTpsTpsTpsGpsTpsCps
GpsTpsTpsTpsTpsGpsTpsCpsGpsTpsTps-
(HEG)po(HEG)po-Toco 3'; (SEQ ID NO: 44)

(19) 5' TpsCpoGpsTpsCpoGpsTpsTpsTpsTpsGpsTpsCpo
GpsTpsTpsTpsTpsGpsTpsCpsGpsTpsTps-
(HEG)po(HEG)po-Toco 3'; (SEQ ID NO: 45)

(20) 5' TpsCpoGpsTpsCpoGpsTpsTpsTpsTpsGpsTpsCpo
GpsTpsTpsTpsTpsGpsTpsCpoGpsTpsTps-
(HEG)po(HEG)po-Toco 3'; (SEQ ID NO: 46)

(21) 5' Toco-po(HEG)po(HEG)po-TpsCpsGpsTpsCpsGps
TpsTpsTpsTpsGpsTpsCpsGpsTpsTpsTpsTpsGpsTps
CpsGpsTpsT 3'; (SEQ ID NO: 47)

(22) 5' Toco-po(HEG)po(HEG)po-TpsCpoGpsTpsCpsGps
TpsTpsTpsTpsGpsTpsCpsGpsTpsTpsTpsTpsGpsTps
CpsGpsTpsT 3'; (SEQ ID NO: 48)

(23) 5' Toco-po(HEG)po(HEG)po-TpsCpoGpsTpsCpoGps
TpsTpsTpsTpsGpsTpsCpsGpsTpsTpsTpsTpsGpsTps
CpsGpsTpsT 3'; (SEQ ID NO: 49)

(24) 5' Toco-po(HEG)po(HEG)po-TpsCpoGpsTpsCpoGps
TpsTpsTpsTpsGpsTpsCpoGpsTpsTpsTpsTpsGpsTps
CpsGpsTpsT 3'; (SEQ ID NO: 50)

(25) 5'-TpsCpoGpsTpsCGpsTpsTpsTpsTpsGpsTpsCGps
TpsTpsTpsTpsGpsTpsCpoGpsTpsTps-HEGps-
Chol 3'; (SEQ ID NO: 51)

(26) 5'-TpsCpoGpsTpsCpoGpsTpsTpsTpsTpsGpsTpsCpo
GpsTpsTpsTpsTpsGpsTpsCpsGpsTpsTps
(HEG)po(HEG)po-Chol 3'; (SEQ ID NO: 52)

(27) 5'-GpsGpsGpsGpsTpsCpsApsApsCpoGpsTpsTpsGps
ApsGpsGpsGpsGpsGpsGps-HEGps-Chol 3'; (SEQ ID NO: 53)

(28) 5'-TpsCpsCpsApsTpsGpsApsCpsGpsTpsTpsCpsCps
TpsGpsApsCpsGpsTpsTps-HEGps-Chol 3'; (SEQ ID NO: 54)

(29) 5'-TpsCpsCpsApsTpsGpsApsCpsGpsTpsTpsCpsCps
TpsGpsApsCpsGpsTpsTps-HEGps-Toco 3'; (SEQ ID NO: 55)

(30) 5' Palmitoyl-po(HEG)po(HEG)po-TpsCpoGpsTps
CpoGpsTpsTpsTpsTpsGpsTpsCpoGpsTpsTpsTpsTps
GpsTpsCpoGpsTpsT 3'; (SEQ ID NO: 56)

wherein:
Chol represents cholesterol;
Toco represents tocopherol;
Palmitoyl represents a palmitoyl group;
HEG represents $((CH_2)_2O)_6$;
po represents a phosphodiester linkage; and
ps represents a phosphorothioate linkage.

wherein the tocopherol, the cholesterol, or the palmitoyl group is covalently linked to the (HEG) directly via a po or ps linkage, or indirectly via a second linker that is linked to (HEG) directly via a po or ps linkage.

In an embodiment, the ODN construct has the following structure:

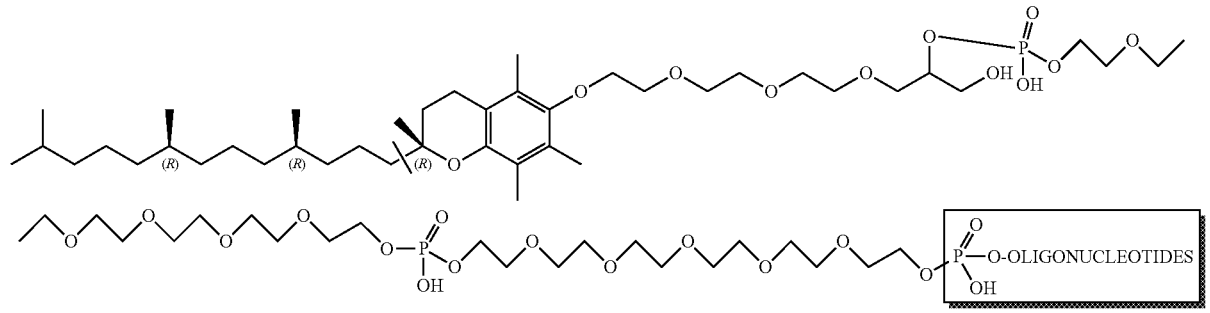

or a racemic or alternative chirality thereof, wherein "Oligonucleotides" represents a CpG ODN having agonistic activity for TLR9.

In an embodiment, the ODN construct has the following structure:

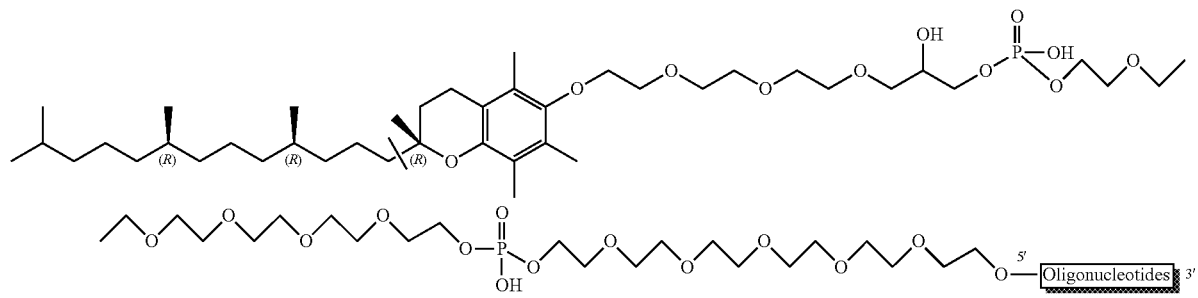

or a racemic or alternative chirality thereof, wherein "Oligonucleotides" represents a CpG ODN having agonistic activity for TLR9.

In an embodiment, CpG ODN contains SEQ ID NO:1, preferably SEQ ID NO:8: 5' TpsCpoGpsTpsCpoGpsTpsTp-sTpsTpsGpsTpsCpoGpsTpsTpsTpsTpsGpsTpsCpoGp-sTpsT 3'.

Figure 24:
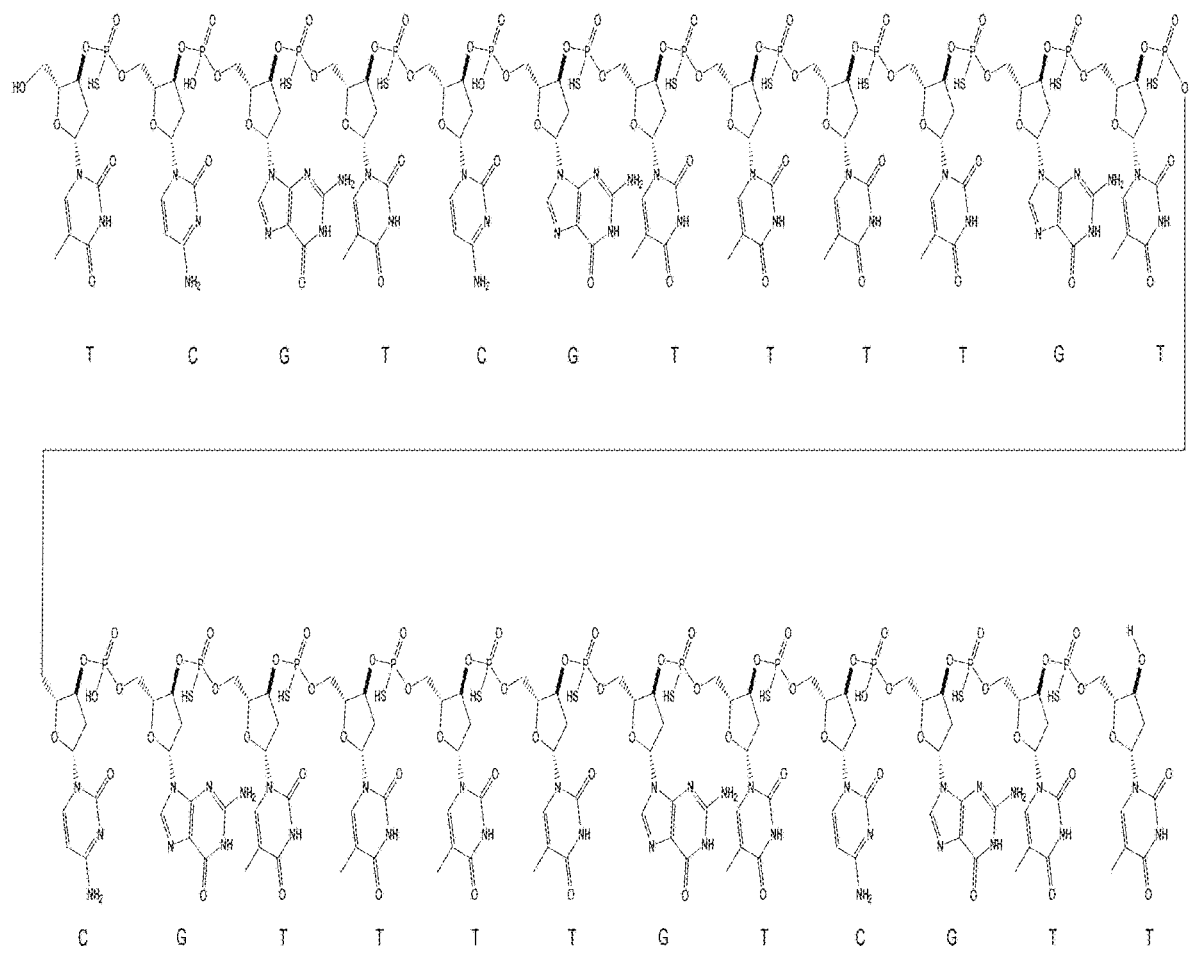
FIG. 24 shows the structure of a CpG ODN.

In an embodiment, CpG ODN contains a structure as shown in FIG. 24.

According to particular aspects, an ODN construct of the present disclosure can be further conjugated to a targeting moiety. As used herein, the term "targeting moiety" refers to any moiety suitable for the delivery of its conjugated agonist to targeted cells. Examples of targeting moiety include, e.g., a carbohydrate, a peptide, a protein, a small molecule, a lipid moiety, or a toxin, that is specifically recognized by a cell surface receptor. Useful carbohydrate moieties include, but are not limited to, galactose, N-acetylgalactosamine (Gal-NAc), fucose, mannose, and sialic acid (N-acetyl: neuraminic acid). According to particular embodiments, the targeting moiety binds to receptors present on the particular target cell types of interest. The targeting moiety helps in targeting the ODN construct to the required target site. One way a targeting moiety can improve delivery is by receptor mediated endocytotic activity. This mechanism of uptake involves the movement of the ODN construct bound to membrane receptors into the interior of an area that is enveloped by the membrane via invagination of the membrane structure or by fusion of the delivery system with the cell membrane. This process is initiated via activation of a cell-surface or membrane receptor following binding of a specific ligand to the receptor. Many receptor-mediated endocytotic systems are known and have been studied, including those that recognize sugars such as galactose, mannose, mannose-6-phosphate, peptides and proteins such as transferrin, asialoglycoprotein, vitamin B12, insulin and epidermal growth factor (EGF). The Asialoglycoprotein receptor (ASGP-R) is a high capacity receptor, which is highly abundant on hepatocytes. The ASGP-R shows a 50-fold higher affinity for N-Acetyl-D-Galactosylamine (GalNAc) than D-Gal. Previous work has shown that multivalency is required to achieve nM affinity, while spacing among sugars is also crucial. The Mannose receptor, with its high affinity to D-mannose represents another important carbohydrate-based ligand-receptor pair. The mannose receptor is highly expressed on specific cell types such as macrophages and possibly dendritic cells Mannose conjugates as well as mannosylated drug carriers have been successfully used to target drug molecules to those cells. For examples, see Biessen et al. (1996) *J. Biol. Chem.* 271, 28024-28030; Kinzel et al. (2003) *J. Peptide Sci.* 9, 375-385; Barratt et al. (1986) *Biochim. Biophys. Acta* 862, 153-64; Diebold et al. (2002) *Somat. Cell Mol. Genetics* 27, 65-74. According to embodiments, the targeting moiety is a lipid moiety. For example, tocopherol can serve as a targeting moiety for vitamin E receptors, and a palmitoyl group can serve as a targeting moiety for LDL receptors.

According to particular embodiments, the targeting moiety binds to receptors present on the particular target cell types of interest An ODN construct of the present disclosure can be conjugated to a targeting moiety directly or indirectly via a linker.

Synthesis

ODN constructs of the present disclosure can be made using methods known in the art in view of the present disclosure. For example, the oligoribonucleotides and oligoribonucleosides used in accordance with this present disclosure can be made with solid phase synthesis, see for example "Oligonucleotide synthesis, a practical approach", Ed. M. J. Gait, IRL Press, 1984; "Oligonucleotides and Analogues, A Practical Approach", Ed. F. Eckstein, IRL Press, 1991 (e.g. Chapter 1, Modern machine-aided methods of ODN synthesis, Chapter 2, Oligoribonucleotide synthesis, Chapter 4, Phosphorothioate oligonucleotides, Chapter 5, Synthesis of oligonucleotide phosphorodithioates). Other particularly useful synthetic procedures, reagents, blocking groups and reaction conditions are described in Martin, P., *Helv. Chim. Acta,* 1995, 78, 486-504; Beaucage, S. L. and Iyer, R. P., *Tetrahedron,* 1992, 48, 2223-2311 and Beaucage, S. L. and Iyer, R. P., *Tetrahedron,* 1993, 49, 6123-6194, or references referred to therein. Mixed backbone compounds having, as for instance, alternating PO or PS linkages can be prepared as is described in U.S. Pat. Nos. 5,378,825, 5,386,023, 5,489,677 and in published PCT applications PCT/US92/04294 and PCT/US92/04305 (published as WO 92/20822 WO and 92/20823, respectively).

Figure 17:
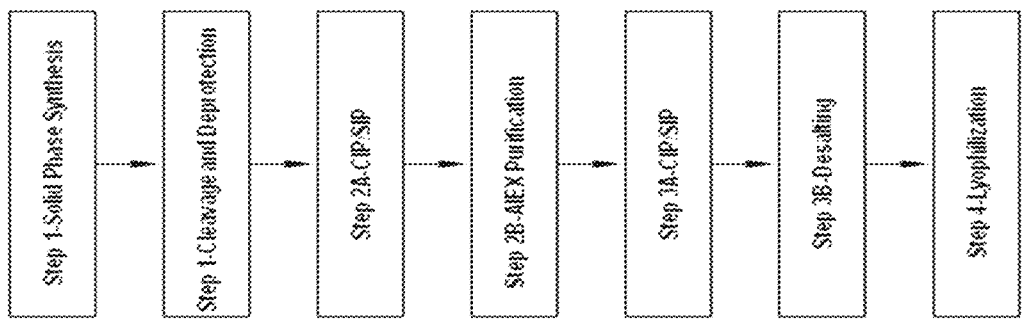
FIG. 17 illustrates a synthesis scheme for ODN constructs according to embodiments of the present disclosure.

An example of a synthesis scheme that can be used to make ODN constructs of the present disclosure is illustrated in FIG. 17 and described in Example 1.

Pharmaceutical Compositions and Methods of Treatment

According to particular aspects, the present disclosure relates to an ODN construct that induces the activity of TLR9. The effect of an ODN construct with agonistic activity for TLR9 on a TLR-dependent immune response can be determined in vitro by measuring a response of immune cells (e.g., Peripheral Blood Mononuclear Cells (PBMCs), mostly consisting of lymphocytes and monocytes) or reporter cells (e.g., HEK293 cells expressing a reporter construct for TLR9) contacted with the agonist. The effect of an ODN construct with agonistic activity for TLR9 on a TLR-dependent immune response can also be determined in vivo, e.g. by measuring cytokine induction in an animal after injection with the agonist. Exemplary methods are described herein, e.g., in the Examples below.

ODN constructs of the present disclosure can be used to treat immune diseases, disorders or conditions, such as viral infections or cancer.

Thus, in another general aspect, the present disclosure relates to a pharmaceutical composition comprising an ODN construct of the present disclosure and a pharmaceutically acceptable carrier.

In another general aspect, the present disclosure relates to a method of stimulating an immune response in a subject in need thereof, comprising administering to the subject a pharmaceutical composition comprising an ODN construct of the present disclosure and a pharmaceutically acceptable carrier.

In another general aspect, the present disclosure relates to a method of treating or reducing symptoms of a disease, disorder or condition, such as an immune disease, disorder or condition, such as a viral infection or cancer, in a subject in need thereof, comprising administering to the subject a pharmaceutical composition of the present disclosure.

According to embodiments of the present disclosure, the pharmaceutical composition comprises a therapeutically effective amount of the an ODN construct. As used herein with reference to an ODN constructs, a therapeutically effective amount means an amount of an ODN construct that stimulates an immune response in a subject in need thereof. Also as used herein with reference to an ODN construct, a therapeutically effective amount means an amount of an ODN construct that results in treatment of an immune disease, disorder, or condition, such as viral infection or cancers; prevents or slows the progression of the immune disease, disorder, or condition, such as viral infection or cancer; reduces or completely alleviates symptoms associated with the immune disease, disorder, or condition, such as viral infection or cancer.

According to particular embodiments, a therapeutically effective amount refers to the amount of therapy which is sufficient to achieve one, two, three, four, or more of the following effects: (i) reduce or ameliorate the severity of the disease, disorder or condition to be treated or a symptom associated therewith; (ii) reduce the duration of the disease, disorder or condition to be treated, or a symptom associated therewith; (iii) prevent the progression of the disease, disorder or condition to be treated, or a symptom associated therewith; (iv) cause regression of the disease, disorder or condition to be treated, or a symptom associated therewith; (v) prevent the development or onset of the disease, disorder or condition to be treated, or a symptom associated therewith; (vi) prevent the recurrence of the disease, disorder or condition to be treated, or a symptom associated therewith; (vii) reduce hospitalization of a subject having the disease, disorder or condition to be treated, or a symptom associated therewith; (viii) reduce hospitalization length of a subject having the disease, disorder or condition to be treated, or a symptom associated therewith; (ix) increase the survival of a subject with the disease, disorder or condition to be treated, or a symptom associated therewith; (x) inhibit or reduce the disease, disorder or condition to be treated, or a symptom associated therewith in a subject; and/or (xi) enhance or improve the prophylactic or therapeutic effect(s) of another therapy.

According to particular embodiments, the disease, disorder or condition to be treated is an immune disease, disorder or condition. According to particular embodiments, the disease, disorder or condition to be treated is a cancer, an inflammatory disease, disorder or condition, an autoimmune disease, disorder or condition, or a disease, disorder or condition caused by a pathogen, such as a viral infection. According to particular embodiments, the cancer or tumor is a cancer caused by a virus, a carcinoma, a sarcoma, or a leukemia. According to particular embodiments, the cancer is a mammary, colon, bladder, lung, prostate, stomach, or pancreas carcinoma or a lymphoblastic or myeloid leukemia. According to particular embodiments, the viral infection is an RNA or DNA virus such as adenovirus, cytomegalovirus, hepatitis A virus (HAV), hepadnaviruses including HBV, chronic HBV, flaviviruses including Yellow Fever virus, hepaciviruses including hepatitis C virus (HCV), herpes simplex type 1 and 2, herpes zoster, human herpesvirus 6, human immunodeficiency virus (HIV), human papilloma virus (HPV), influenza A virus, influenza B virus, measles, parainfluenza virus, pestivirus, poliovirus, poxvirus, rhinovirus, coronovirus, respiratory syncytial virus (RSV), multiple families of viruses that cause hemorrhagic fevers, including the Arenaviruses, the Bunyaviruses and Filoviruses, and a range of viral encephalitides caused by RNA and DNA viruses. According to more particular embodiments, the disease to be treated is HBV infection or chronic HBV infection.

Chronic HBV is preferably characterized by the detectable presence of HBV in a subject for more than 6 months. More preferably, a chronic HBV infection referred to herein follows the definition published by the Centers for Disease Control and Prevention (CDC), according to which a chronic HBV infection is characterized by the following laboratory criteria: (i) negative for IgM antibodies to hepatitis B core antigen (IgM anti-HBc) and positive for hepatitis B surface antigen (HBsAg), hepatitis B e antigen (HBeAg), or nucleic acid test for hepatitis B virus DNA, or (ii) positive for HBsAg or nucleic acid test for HBV DNA, or positive for HBeAg two times at least 6 months apart.

According to particular embodiments, a therapeutically effective amount refers to the amount of a therapy which is sufficient to treat a chronic HBV infection. Accordingly, a therapeutically effective amount refers to the amount of therapy which is sufficient to achieve one, two, three, four, or more of the following effects: (i) reduce or ameliorate the severity of an HBV infection or a symptom associated therewith; (ii) reduce the duration of an HBV infection or symptom associated therewith; (iii) prevent the progression of an HBV infection or symptom associated therewith; (iv) cause regression of an HBV infection or symptom associated therewith; (v) prevent the development or onset of an HBV infection, or symptom associated therewith; (vi) prevent the recurrence of an HBV infection or symptom associated therewith; (vii) reduce hospitalization of a subject having an HBV infection; (viii) reduce hospitalization length of a subject having an HBV infection; (ix) increase the survival of a subject with an HBV infection; (x) eliminate an HBV infection in a subject; (xi) inhibit or reduce HBV replication in a subject; and/or (xii) enhance or improve the prophylactic or therapeutic effect(s) of another therapy.

According to particular embodiments, a therapeutically effective amount refers to the amount of a therapy which is sufficient to achieve one, two, three or four of the following effects: (i) reduce the amount of hepatitis B surface antigen (HBsAg) in the subject by 10%, 20%, 30%, 40%, 50%, 60%, 70%, 80%, 90%, 95% or more; (ii) reduce the amount of hepatitis B e antigen (HBeAg) in the subject by 10%, 20%, 30%, 40%, 50%, 60%, 70%, 80%, 90%, 95% or more; (iii) reduce the amount of hepatitis B virus DNA in the subject by 10%, 20%, 30%, 40%, 50%, 60%, 70%, 80%, 90%, 95% or more; and/or (iv) reduce the amount of anti-HBsAg antibodies in the subject by 10%, 20%, 30%, 40%, 50%, 60%, 70%, 80%, 90%, 95% or more.

According to particular embodiments, a therapeutically effective amount refers to the amount of a therapy which is sufficient to treat a cancer. Accordingly, a therapeutically effective amount refers to the amount of therapy which is sufficient to achieve one, two, three, four, or more of the following effects: (i) reduce or ameliorate the severity of a cancer or a symptom associated therewith; (ii) reduce the duration of a cancer or symptom associated therewith; (iii) prevent the progression of a cancer or symptom associated therewith; (iv) cause regression of a cancer or symptom associated therewith; (v) prevent the development or onset of a cancer, or symptom associated therewith; (vi) prevent the recurrence of a cancer or symptom associated therewith; (vii) reduce hospitalization of a subject having a cancer; (viii) reduce hospitalization length of a subject having a cancer; (ix) increase the survival of a subject with a cancer; (x) eliminate a cancer in a subject; and/or (xi) enhance or improve the prophylactic or therapeutic effect(s) of another therapy.

The therapeutically effective amount or dosage can vary according to various factors, such as the means of administration, the target site, the physiological state of the subject (including, e.g., age, body weight, health), whether the subject is a human or an animal, other medications administered, and whether the treatment is prophylactic or therapeutic. Treatment dosages are optimally titrated to optimize safety and efficacy.

The mode of administration for therapeutic use of the an ODN constructs of the present disclosure can be any suitable route that delivers the agent to the host. For example, the compositions described herein can be formulated to be suitable for parenteral administration, e.g., intradermal, intramuscular, intraperitoneal, intravenous, subcutaneous, intranasal or intracranial administration, or they can be administered into the cerebrospinal fluid of the brain or spine.

According to particular embodiments, the compositions described herein are formulated to be suitable for the intended route of administration to a subject. For example, the compositions described herein can be formulated to be suitable for intravenous, subcutaneous, intratumoral or intramuscular administration. According to preferred embodiments, the compositions described herein are formulated to be suitable for intravenous, subcutaneous, or intratumoral administration.

The treatment can be given in a single dose schedule, or as a multiple dose schedule in which a primary course of treatment can be with 1-10 separate doses, followed by other doses given at subsequent time intervals required to maintain and/or reinforce the response, for example, at 1-4 months for a second dose, and if needed, a subsequent dose(s) after several months. Examples of suitable treatment schedules include: (i) 0, 1 month and 6 months, (ii) 0, 7 days and 1 month, (iii) 0 and 1 month, (iv) 0 and 6 months, or other schedules sufficient to elicit the desired responses expected to reduce disease symptoms or reduce severity of disease.

According to particular embodiments, a composition used in the treatment of an immune disease, disorder or condition, or a viral disease, such as chronic HBV, or a cancer, can be used in combination with other agents that are effective for treatment of related diseases, disorders or conditions. Examples of such agents include, but are not limited to, CAMs, DAAs, other TLRs, ASO/siRNA, checkpoint inhibitors, other chemotherapeutics, CAR-T.

In another general aspect, the present disclosure relates to a method of producing a pharmaceutical composition comprising an ODN construct of the present disclosure, comprising combining an ODN construct with a pharmaceutically acceptable carrier to obtain the pharmaceutical composition.

In another general aspect, the present disclosure relates to a method of treating chronic HBV infection in a subject in need thereof, comprising administering to the subject a pharmaceutical composition comprising an ODN construct of the present disclosure.

In another general aspect, the present disclosure relates to a method of treating a tumor, preferably a cancer, in a subject in need thereof, comprising administering to the subject a pharmaceutical composition comprising an ODN construct of the present disclosure.

The contents of all cited references (including literature references, issued patents, published patent applications, and co-pending patent applications) cited throughout this application are hereby expressly incorporated by reference.

EMBODIMENTS

The present disclosure provides also the following non-limiting embodiments.

Embodiment 1 is an ODN construct having the formula of Formula I:

5'$M_1$-$L_1$-[CpG ODN]-$L_2$-$M_2$3', wherein:

each of $M_1$ and $M_2$ independently represents a lipid moiety, preferably the lipid moiety comprises at least one selected from the group consisting of cholesterol, tocopherol, a palmitoyl group, and a stearyl group, optionally one of $M_1$ and $M_2$ is absent;

each of $L_1$ and $L_2$ independently represents a linker, preferably the linker comprises at least 10 atoms selected from the group consisting of carbon, nitrogen, oxygen, hydrogen, sulfur and phosphorus, and L is covalently linked to the CpG ODN via a cleavable linkage, preferably via an ester or an amide bond, optionally one of $L_1$ and $L_2$ is absent when the respective $M_1$ or $M_2$ is absent; and preferably, CpG ODN comprises at least one CpG motif having a phosphodiester (po) internucleotide linkage;

optionally, the CpG ODN construct of formula (I) is further covalently conjugated to a targeting moiety, which is preferably selected from the group consisting of galactose, N-acetylgalactosamine (GalNAc), fucose, mannose, sialic acid, N-acetyl neuraminic acid.

Embodiment 2 is a CpG ODN construct having a formula of:

| 5'M-L-[CpG ODN]3', or | Formula (IIa): |
| 5'[CpG ODN]-L-M3' | Formula (IIb): | wherein:

M represents a lipid moiety, preferably the lipid moiety comprises at least one selected from the group consisting of cholesterol, tocopherol, a palmitoyl group, and a stearyl group;

L represents a linker comprising at least 1 atoms selected from the group consisting of carbon, nitrogen, oxygen, hydrogen, sulfur and phosphorus, and L is covalently linked to the CpG ODN via a cleavable linkage, preferably via an ester or an amide bond; and CpG ODN comprises at least one CpG motif having a po internucleotide linkage, preferably comprises at least two, three or four CpG motifs each having the po internucleotide linkage;

optionally, the CpG ODN construct of Formula (IIa) or (IIb) is further covalently conjugated to a targeting moiety, which is preferably selected from the group consisting of galactose, N-acetylgalactosamine (GalNAc), fucose, mannose, sialic acid, N-acetyl neuraminic acid.

Embodiment 2a is the ODN construct of Embodiment 1 or 2, wherein the linker comprises 10-100 atoms selected from the group consisting of carbon, nitrogen, oxygen, hydrogen, sulfur and phosphorus.

Embodiment 2b is the ODN construct of Embodiment 2a, wherein the linker comprises 20-100 atoms selected from the group consisting of carbon, nitrogen, oxygen, hydrogen, sulfur and phosphorus.

Embodiment 2c is the ODN construct of Embodiment 2a, wherein the linker comprises 30-100 atoms selected from the group consisting of carbon, nitrogen, oxygen, hydrogen, sulfur and phosphorus.

Embodiment 2d is the ODN construct of Embodiment 2a, wherein the linker comprises 40-100 atoms selected from the group consisting of carbon, nitrogen, oxygen, hydrogen, sulfur and phosphorus.

Embodiment 2e is the ODN construct of Embodiment 2a, wherein the linker comprises 50-100 atoms selected from the group consisting of carbon, nitrogen, oxygen, hydrogen, sulfur and phosphorus.

Embodiment 2f is the ODN construct of Embodiment 2a, wherein the linker comprises 60-100 atoms selected from the group consisting of carbon, nitrogen, oxygen, hydrogen, sulfur and phosphorus.

Embodiment 2g is the ODN construct of Embodiment 2a, wherein the linker comprises 70-100 atoms selected from the group consisting of carbon, nitrogen, oxygen, hydrogen, sulfur and phosphorus.

Embodiment 2h is the ODN construct of Embodiment 2a, wherein the linker comprises 80-100 atoms selected from the group consisting of carbon, nitrogen, oxygen, hydrogen, sulfur and phosphorus.

Embodiment 3 is the ODN construct of Embodiment 1 or 2, wherein the linker comprises $((CH_2)_2O)_m$, wherein m is an integer from 1 to 15, such as 1, 2, 3, 4, 5, 6, 7, 8, 9, 10, 11, 12, 13, 14 or 15.

Embodiment 4 is the ODN construct of Embodiment 3, wherein the linker comprises $(((CH_2)_2O)_m—X)_n$, wherein n is an integer from 1 to 5, such as 1, 12, 3, 4, or 5, and X is independently a phosphodiester (po) or phosphorothioate (ps) linkage.

Embodiment 4a is the ODN construct of Embodiment 4, wherein the linker comprises $(((CH_2)_2O)_6—X)_n$.

Embodiment 4b is the ODN construct of Embodiment 4a, wherein the linker comprises $((CH_2)_2O)_6$-po.

Embodiment 4c is the ODN construct of Embodiments 4a, wherein the linker comprises $((CH_2)_2O)_6$-po-$((CH_2)_2O)_6$-po.

Embodiment 4d is the ODN construct of Embodiments 4a, wherein the linker comprises $((CH_2)_2O)_6$-ps-$((CH_2)_2O)_6$-po.

Embodiment 5 is a CpG ODN construct having a structure of:

| 5'M-Y—$(((CH_2)_2O)_m—X)_n$—$Y_2$—[CpG ODN]—$Y_3$-$M_2$3', or | Formula (IIIa): |
| 5'$M_2$-$Y_3$—[CpG ODN]—$Y_2$—$(((CH_2)_2O)_m—X)_n$—$Y_1$-$M_1$3' | Formula (IIIb): | wherein:

$M_1$ represents a lipid moiety, preferably the lipid moiety comprises at least one selected from the group consisting of cholesterol, tocopherol, a palmitoyl group, and a stearyl group, $M_2$ represents a lipid moiety, a targeting moiety, or is absent, $Y_1$ is a bond or a linker, preferably ethylene glycol having the formula $((CH_2)_2O)_o$, wherein o is 1-15, covalently linked to $(((CH_2)_2O)_m—X)_n$ via a phosphodiester (po) linkage, a phosphorothioate (ps) linkage or a bond, X is independently a bond, a po linkage or a ps linkage, each of $Y_2$ and $Y_3$ is independently a cleavable linkage, preferably comprises an ester or an amide bond, more preferably comprises a po linkage or a phosphoramidate linkage, most preferably a po linkage, provided that when $M_2$ is absent, $Y_3$ is absent, CpG ODN comprises at least one CpG motif having a po internucleotide linkage, preferably comprises at least two, three or four CpG motifs each having the po internucleotide linkage;

m is an integer from 1 to 15, and n is an integer from 1 to 5.

Embodiment 6 is the ODN construct of embodiment 5, wherein $M_2$ is a targeting.

Embodiment 6a is the ODN construct of embodiment 6, wherein $M_2$ is the targeting selected from the group consisting of galactose, N-acetylgalactosamine (GalNAc), fucose, mannose, sialic acid, N-acetyl neuraminic acid.

Embodiment 6b is the ODN construct of embodiment 5, wherein $M_2$ and $Y_3$ are absent.

Embodiment 7 is a CpG ODN construct having a formula of:

$$5'M-Y-(((CH_2)_2O)_m-X)_n-Y_2-[CpG\ ODN]3', \text{ or Formula (IVa):}$$

$$5'[CpG\ ODN]-Y_2-(((CH_2)_2O)_m-X)_n-Y_1-M3' \quad \text{Formula (IVb):}$$

wherein:

M represents a lipid moiety, preferably the lipid moiety comprises at least one selected from the group consisting of cholesterol, tocopherol, a palmitoyl group, and a stearyl group, $Y_1$ is a bond or a linker, preferably ethylene glycol having the formula $((CH_2)_2O)_o$, wherein o is 1-15, covalently linked to $(((CH_2)_2O)_m-X)_n$ via a phosphodiester (po) linkage, a phosphorothioate (ps) linkage or a bond, X is independently a bond, a phosphodiester (po) linkage or a phosphorothioate (ps) linkage, $Y_2$ is a cleavable linkage, preferably comprises an ester or an amide bond, more preferably comprises a po linkage or a phosphoramidate linkage, most preferably a po linkage;

CpG ODN comprises at least one CpG motif having a po internucleotide linkage, preferably comprises at least two, three or four CpG motifs each having the po internucleotide linkage;

m is an integer from 1 to 15, preferably 6; and n is an integer from 1 to 5, preferably 2;

optionally, the CpG ODN construct of Formula (IVa) or (IVb) is further covalently conjugated to a targeting moiety, which is preferably selected from the group consisting of galactose, N-acetylgalactosamine (GalNAc), fucose, mannose, sialic acid, N-acetyl neuraminic acid.

Embodiment 8 is the ODN construct of any one of Embodiment 5 to 7, wherein $Y_2$ comprises an ester bond.

Embodiment 8a is the ODN construct of Embodiment 8, wherein $Y_2$ is a phosphodiester (po) linkage.

Embodiment 8b is the ODN construct of any one of Embodiment 5 to 7, wherein $Y_2$ comprises an amide bond.

Embodiment 8c is the ODN construct of Embodiment 8b, wherein $Y_2$ is a phosphoramidate linkage.

Embodiment 9 is the ODN construct of any one of Embodiment 5 to 8c, wherein $Y_1$ comprises ethylene glycol having the formula $((CH_2)_2O)_o$, wherein o is 1-15, covalently linked to $(((CH_2)_2O)_m-X)_n$ via a bond.

Embodiment 9a is the ODN construct of Embodiment 9, wherein $Y_1$ comprises ethylene glycol having the formula $((CH_2)_2O)_o$, wherein o is 1-15, covalently linked to $(((CH_2)_2O)_m-X)_n$ via a po linkage.

Embodiment 9b is the ODN construct of Embodiment 9, wherein $Y_1$ comprises ethylene glycol having the formula $((CH_2)_2O)_o$, wherein o is 1-15, covalently linked to $(((CH_2)_2O)_m-X)_n$ via a ps linkage.

Embodiment 10 is the ODN construct of any one of Embodiment 4 to 9b, wherein m is an integer of 1 to 15.

Embodiment 10a is the ODN construct of Embodiment 10, wherein m is 1.

Embodiment 10b is the ODN construct of Embodiment 10, wherein m is 2.

Embodiment 10c is the ODN construct of Embodiment 10, wherein m is 3.

Embodiment 10d is the ODN construct of Embodiment 10, wherein m is 4.

Embodiment 10e is the ODN construct of Embodiment 10, wherein m is 5.

Embodiment 10f is the ODN construct of Embodiment 10, wherein m is 6.

Embodiment 10g is the ODN construct of Embodiment 10, wherein m is 7.

Embodiment 10h is the ODN construct of Embodiment 10, wherein m is 8.

Embodiment 10i is the ODN construct of Embodiment 10, wherein m is 9.

Embodiment 10j is the ODN construct of Embodiment 10, wherein m is 10.

Embodiment 10k is the ODN construct of Embodiment 10, wherein m is 11.

Embodiment 10l is the ODN construct of Embodiment 10, wherein m is 12.

Embodiment 10m is the ODN construct of Embodiment 10, wherein m is 11.

Embodiment 10n is the ODN construct of Embodiment 10, wherein m is 14.

Embodiment 10o is the ODN construct of Embodiment 10, wherein m is 15.

Embodiment 11 is the ODN construct of any one of Embodiments 4 to 10o, wherein n is an integer of 1 to 5.

Embodiment 11a is the ODN construct of Embodiment 11, wherein n is 1.

Embodiment 11b is the ODN construct of Embodiment 11 wherein n is 2.

Embodiment 11c is the ODN construct of Embodiment 11 wherein n is 3.

Embodiment 11d is the ODN construct of Embodiment 11, wherein n is 4.

Embodiment 11e is the ODN construct of Embodiment 11, wherein n is 5.

Embodiment 12 is the ODN construct of any one of Embodiments 4-10 and 11, wherein m is 6 and n is 2.

Embodiment 13 is an ODN construct having a structure selected from the group consisting of:

5' M-po(HEG)po(HEG)po-[CpG ODN] 3';

5' M-ps(HEG)po(HEG)po-[CpG ODN] 3',

5' M-ps(HEG)ps(HEG)po-[CpG ODN] 3',

5' M-po(HEG)ps(HEG)po-[CpG ODN] 3',

5' [CpG ODN]-po(HEG)po(HEG)po-M 3',

5' [CpG ODN]-po(HEG)ps(HEG)po-M 3',

5' [CpG ODN]-po(HEG)ps(HEG)ps-M 3', and

5' [CpG ODN]-po(HEG)po(HEG)ps-M 3', wherein:

M represents a lipid moiety comprising at least one selected from the group consisting of cholesterol, tocopherol, a palmitoyl group, and a stearyl group;

po represents a phosphodiester linkage;

HEG represents $((CH_2)_2O)_6$;

ps represents a phosphorothioate linkage; and

CpG ODN comprises at least one CpG motif having a po internucleotide linkage, preferably comprises at least two, three or four CpG motifs each having the po internucleotide linkage, wherein M is covalently linked to (HEG) directly via a po or ps linkage, or indirectly via a second linker that is linked to (HEG) directly via a po or ps linkage.

Embodiment 14 is the ODN construct of any one of Embodiments 1 to 13, wherein the lipid moiety is cholesterol.

Embodiment 14a is the ODN construct of any one of Embodiments 1 to 13, wherein the lipid moiety is tocopherol.

Embodiment 14b is the ODN construct of any one of Embodiments 1 to 13, wherein the lipid moiety is a palmitoyl group.

Embodiment 14c is the ODN construct of any one of Embodiments 1 to 13, wherein the lipid moiety is a stearyl group.

Embodiment 15 is an ODN construct having a structure selected from the group consisting of:

5' Toco-po(HEG)po(HEG)po-[CpG ODN] 3', wherein Toco represents tocopherol,

5' Chol-po(HEG)po(HEG)po-[CpG ODN] 3', wherein Chol represents cholesterol,

5' Palm-po(HEG)po(HEG)po-[CpG ODN] 3', wherein Palm represents a palmitoyl group, 5' [CpG ODN]-po(HEG)ps-Chol 3', wherein Chol represents cholesterol, 5' [CpG ODN]-po(HEG)ps-Toco 3', wherein Toco represents tocopherol, and 5' [CpG ODN]-po(HEG)ps-Palm 3', wherein Palm represents a palmitoyl group, wherein:
po represents a phosphodiester linkage;
HEG represents $((CH_2)_2O)_6$;
ps represents a phosphorothioate linkage; and
CpG ODN comprises at least one CpG motif having a po internucleotide linkage, preferably comprises at least two, three or four CpG motifs each having the po internucleotide linkage, wherein the tocopherol, the cholesterol, or the palmitoyl group is covalently linked to the (HEG) directly via a po or ps linkage, or indirectly via a second linker that is linked to (HEG) directly via a po or ps linkage.

Embodiment 15a is the ODN construct of embodiment 15, wherein the tocopherol, the cholesterol, or the palmitoyl group is covalently the second linker and the second linker is covalently linked to the (HEG) directly via the po or ps linkage.

Embodiment 16 is an ODN construct having the following structure:

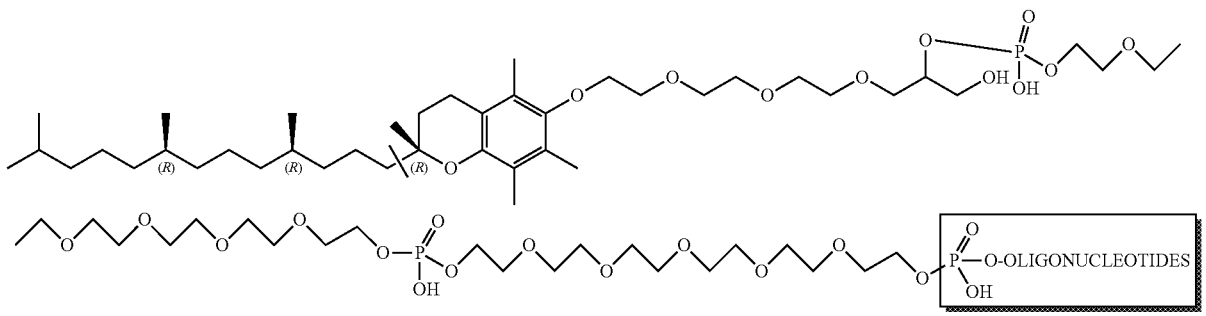

or a racemic or alternative chirality thereof, wherein "Oligonucleotides" represents a CpG ODN comprising at least one CpG motif having a po internucleotide linkage, preferably comprising at least two, three or four CpG motifs each having the po internucleotide linkage, optionally, the ODN construct is further conjugated to a targeting moiety, directly or via a linker.

Embodiment 16a is an ODN construct having the following structure:

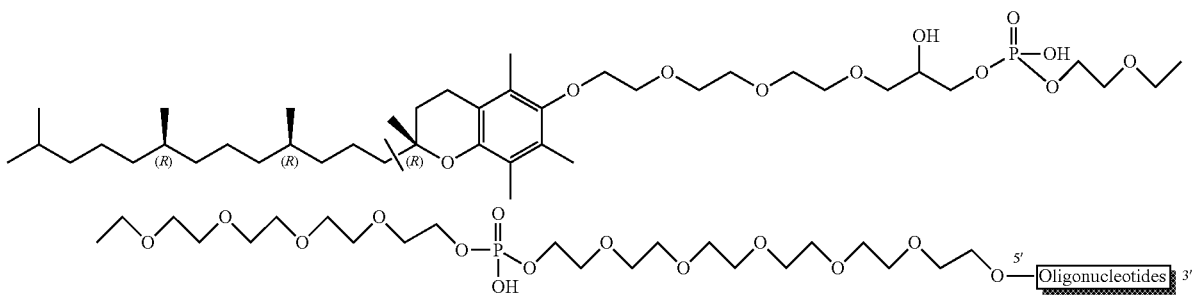

or a racemic or alternative chirality thereof, wherein "Oligonucleotides" represents a CpG ODN comprising at least one CpG motif having a po internucleotide linkage, preferably comprising at least two, three or four CpG motifs each having the po internucleotide linkage, optionally, the ODN construct is further conjugated to a targeting moiety, directly or via a linker.

Figure 25:
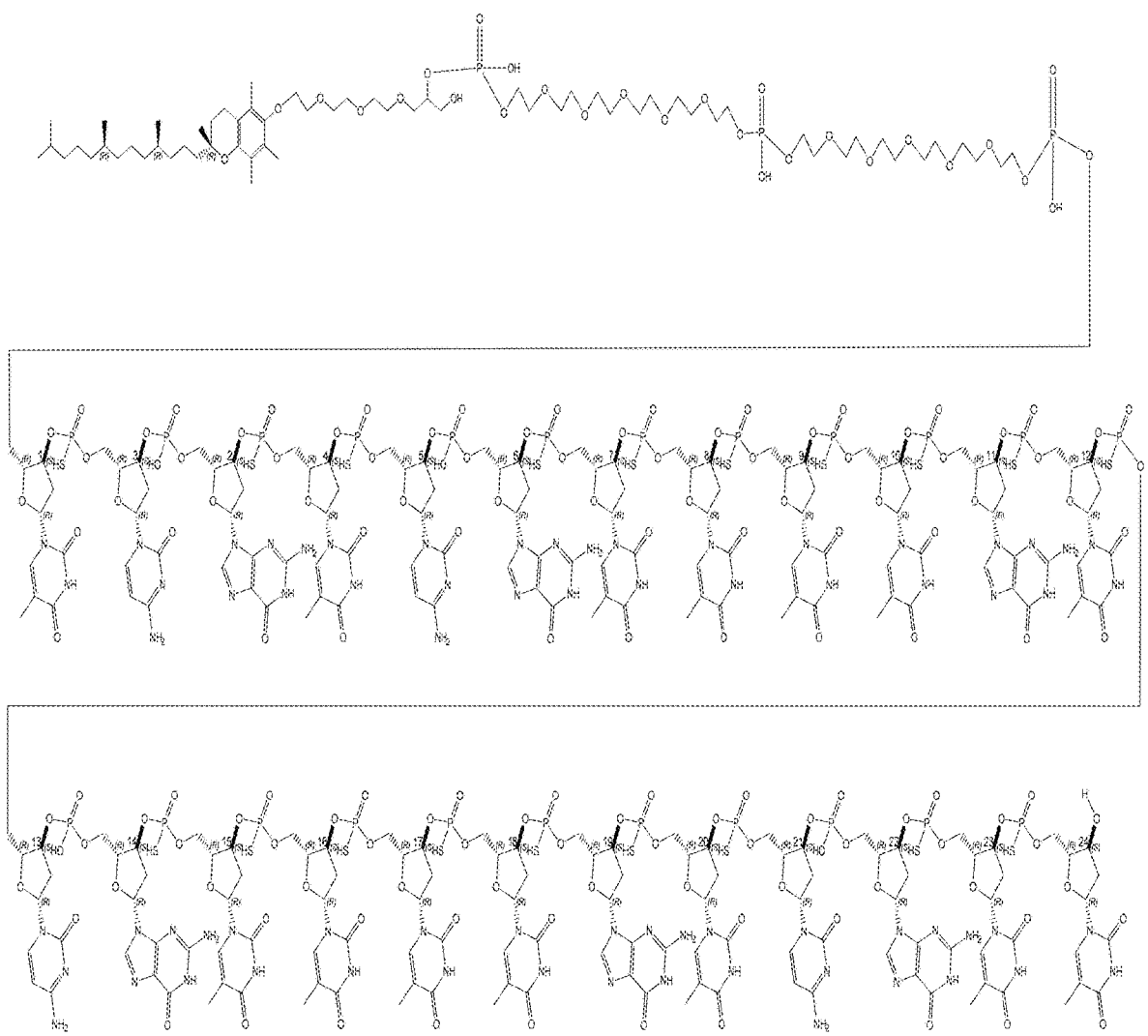
FIG. 25 shows the structure of an ODN construct.

Embodiment 16b is an ODN construct having a structure as shown in FIG. 25 or a racemic or alternative chirality thereof.

Figure 26:
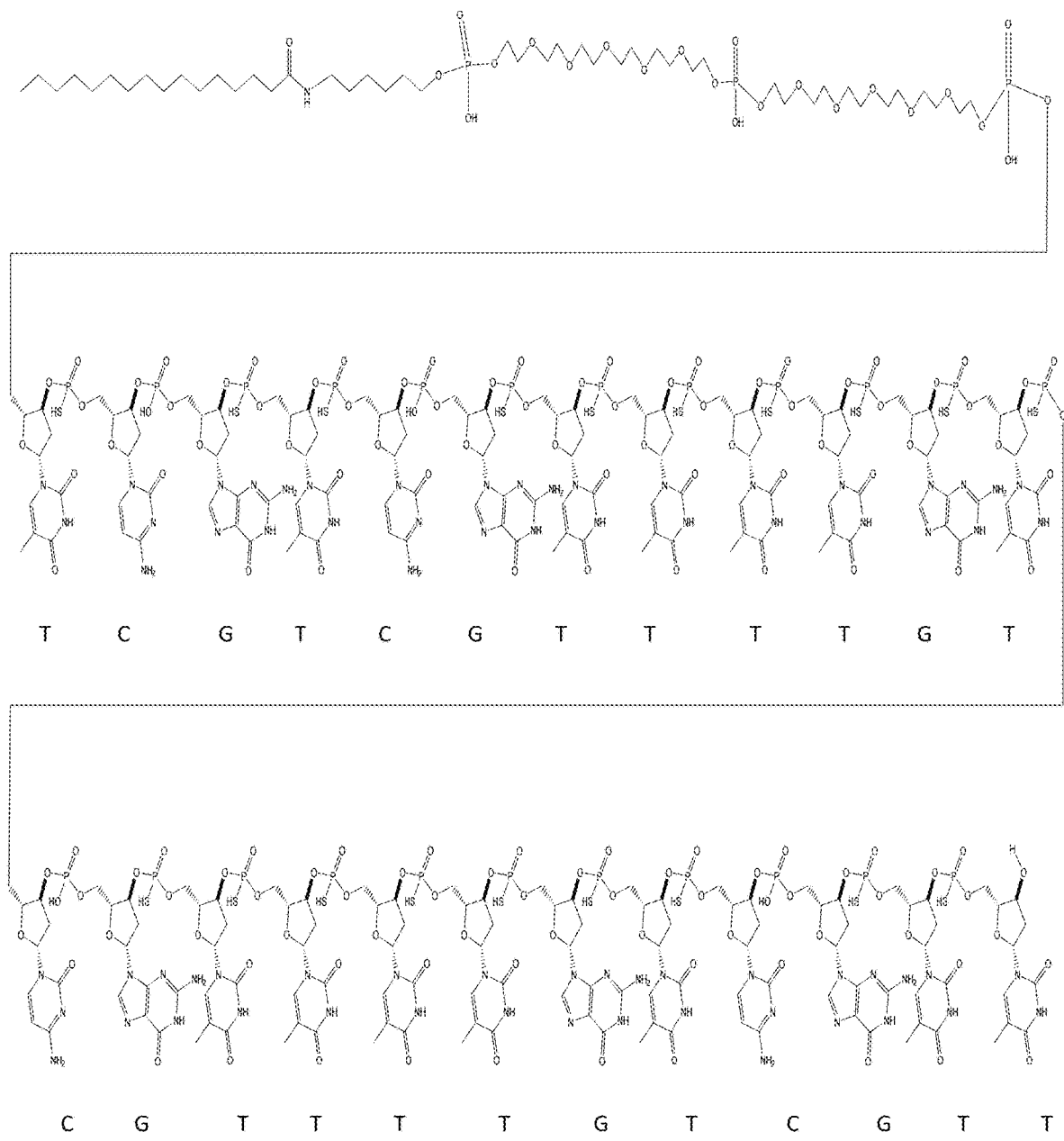
FIG. 26 shows the structure of an ODN construct.

Embodiment 16c is an ODN construct having a structure as shown in FIG. 26.

Figure 27:
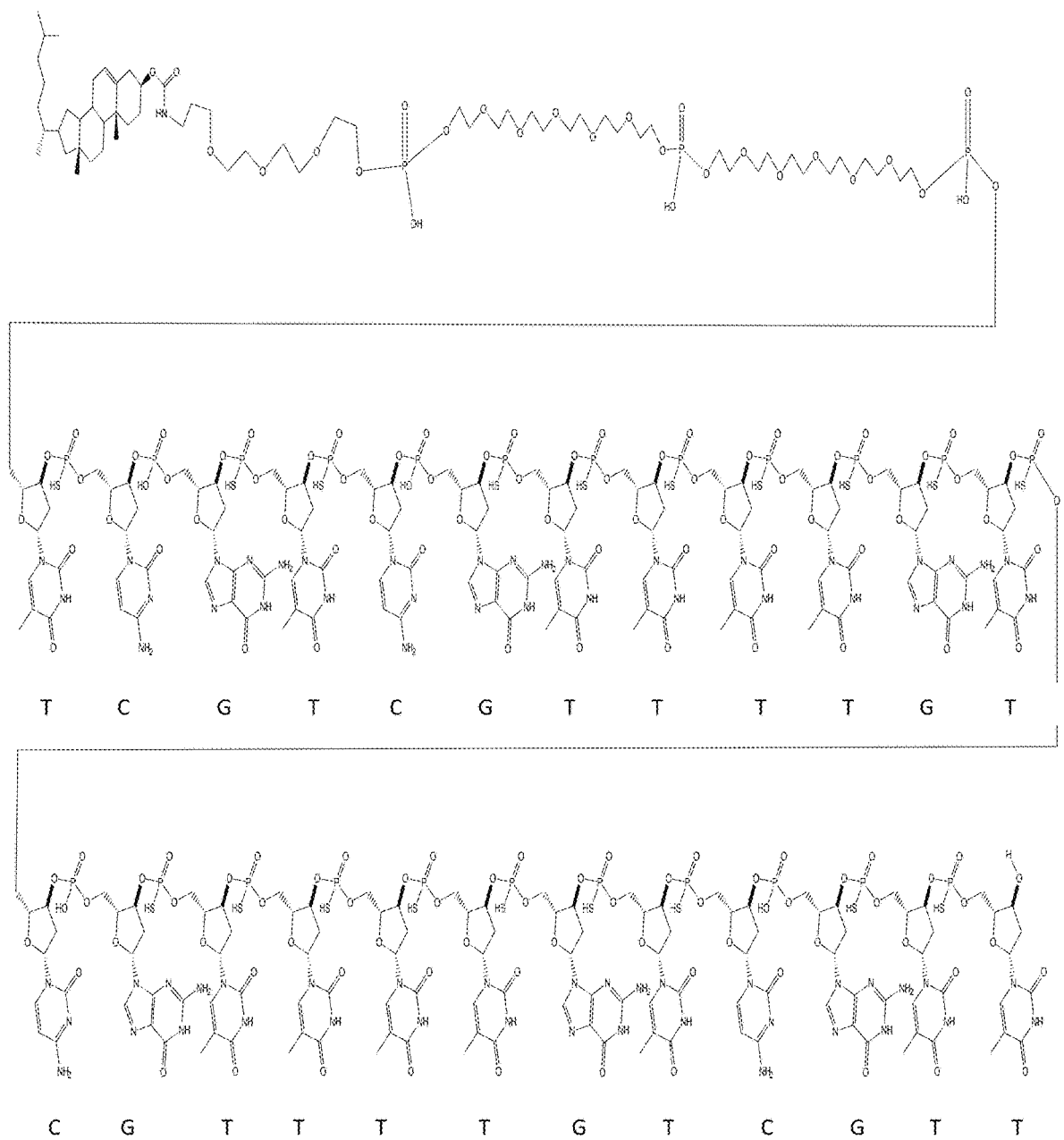
FIG. 27 shows the structure of an ODN construct.

Embodiment 16d is an ODN construct having a structure as shown in FIG. 27 or a racemic or alternative chirality thereof.

Embodiment 17 is the ODN construct of any of Embodiments 1 to 16, wherein the CpG ODN has a phosphorothioate (ps) internucleotide linkage.

Embodiment 18 is the ODN construct of any of Embodiments 1 to 17, wherein the CpG ODN has a stereodefined phosphorothioate (ps) internucleotide linkage.

Embodiment 19 is the ODN construct of any of Embodiments 1 to 18, wherein one to four of the CpG dinucleotides in the CpG ODN each have a phosphodiester (po) internucleotide linkage.

Embodiment 19a is the ODN construct of Embodiment 19, wherein the CpG ODN comprises at least two CpG motifs each having a po internucleotide linkage.

Embodiment 19b is the ODN construct of Embodiment 19, wherein the CpG ODN comprises at least three CpG motifs each having a po internucleotide linkage.

Embodiment 19c is the ODN construct of Embodiment 19, wherein the CpG ODN comprises at least four CpG motifs each having a po internucleotide linkage.

Embodiment 20 is the ODN construct of any of Embodiments 19 to 19c, wherein each of the remaining internucleotide linkages of the CpG ODN are phosphorothioate (ps) internucleotide linkages.

Embodiment 21 is the ODN construct of any one of Embodiments 1 to 20, wherein the CpG ODN comprises, preferably consists of, a polynucleotide sequence selected from the group consisting of:

```
                                (SEQ ID NO: 1)
(1)     5' TCGTCGTTTTGTCGTTTTGTCGTT 3';

(SEQ ID NO: 2)
(2)     5' GGGGGACGATCGTCGGGGGG 3';

(SEQ ID NO: 3)
(3)     5' GGGGTCAACGTTGAGGGGGG 3';

(SEQ ID NO: 4)
(4)     5' TCCATGACGTTCCTGACGTT 3';

(SEQ ID NO: 5)
(5)     5' TCGTCGTTTTCGGCGCGCGCCG 3';

(SEQ ID NO: 6)
(6)     5' TCGTCGTTACGTAACGACGACGTT 3';
and (SEQ ID NO: 7)
(7)     5' TCGTCGTTTTGTCGTTTTGTCGT 3'.
```

Embodiment 21a is the ODN construct of Embodiment 21, wherein the CpG ODN comprises, preferably consists of, a polynucleotide sequence that is, or is at least, 70%, 75%, 80%, 85%, 90%, 91%, 92%, 93%, 94%, 95%, 96%, 97%, 98%, 99% or 100% identical to one of SEQ ID NOs: 1-7.

Embodiment 22 is the ODN construct of any one of Embodiments 1 to 21, wherein the CpG ODN comprises, preferably consists of, a polynucleotide sequence selected from the group consisting of:

```
                                (SEQ ID NO: 8)
(1)    5' TpsCpoGpsTpsCpoGpsTpsTpsTpsTpsGpsTpsCpoGps
          TpsTpsTpsTpsGpsTpsCpoGpsTpsT 3';

(SEQ ID NO: 9)
(2)    5' TpsCpsGpsTpsCpoGpsTpsTpsTpsTpsGpsTpsCpsGps
          TpsTpsTpsTpsGpsTpsCpsGpsTpsT 3';

(SEQ ID NO: 10)
(3)    5' TpsCpsGpsTpsCpoGpsTpsTpsTpsTpsGpsTpsCpoGps
          TpsTpsTpsTpsGpsTpsCpsGpsTpsT 3';

(SEQ ID NO: 11)
(4)    5' TpsCpsGpsTpsCpsGpsTpsTpsTpsTpsGpsTpsCpoGps
          TpsTpsTpsTpsGpsTpsCpsGpsTpsT 3';

(SEQ ID NO: 12)
(5)    5' TpsCpsGpsTpsCpsGpsTpsTpsTpsTpsGpsTpsCpsGps
          TpsTpsTpsTpsGpsTpsCpoGpsTpsT 3';

(SEQ ID NO: 13)
(6)    5' TpsCpsGpsTpsCpsGpsTpsTpsTpsTpsGpsTpsCpoGps
          TpsTpsTpsTpsGpsTpsCpoGpsTpsT 3';

(SEQ ID NO: 14)
(7)    5' TpsCpsGpsTpsCpoGpsTpsTpsTpsTpsGpsTpsCpoGps
          TpsTpsTpsTpsGpsTpsCpoGpsTpsT 3';

(SEQ ID NO: 15)
(8)    5' TpsCpsGpsTpsCpsGpsTpsTpsApsCpsGpsTpsApsAps
          CpsGpsApsCpsGpsApsCpsGpsTpsT 3';

(SEQ ID NO: 16)
(9)    5' TpsCpsGpsTpsCpoGpsTpsTpsApsCpsGpsTpsApsAps
          CpsGpsApsCpsGpsApsCpsGpsTpsT 3';

(SEQ ID NO: 17)
(10)   5' TpsCpsGpsTpsCpoGpsTpsTpsApsCpoGpsTpsApsAps
          CpsGpsApsCpsGpsApsCpsGpsTpsT 3';

(SEQ ID NO: 18)
(11)   5' TpsCpsGpsTpsCpoGpsTpsTpsApsCpoGpsTpsApsAps
          CpoGpsApsCpsGpsApsCpsGpsTpsT 3';

(SEQ ID NO: 19)
(12)   5' TpsCpsGpsTpsCpoGpsTpsTpsApsCpoGpsTpsApsAps
          CpoGpsApsCpoGpsApsCpsGpsTpsT 3';

(SEQ ID NO: 20)
(13)   5' GpsGpsGpsGpsGpsApsCpoGpsApsTpsCpoGpsTpsCpo
          GpsGpsGpsGpsGpsG 3';

(SEQ ID NO: 21)
(14)   5' GpsGpsGpsGpsTpsCpsApsApsCpoGpsTpsTpsGpsAps
          GpsGpsGpsGpsGpsG 3';

(SEQ ID NO: 22)
(15)   5' TpsCpsCpsApsTpsGpsApsCpsGpsTpsTpsCpsCpsTps
          GpsApsCpsGpsTpsT 3';

(SEQ ID NO: 23)
(16)   5' TpsCpsGpsTpsCpsGpsTpsTpsTpsTpsCpsGpsGpsCps
          GpsCpsGpsCpsGpsCpsCps G3';

(SEQ ID NO: 24)
(17)   5' TpsCpoGpsTpsCpsGpsTpsTpsTpsTpsGpsTpsCpsGps
          TpsTpsTpsTpsGpsTpsCps GpsT 3';

(SEQ ID NO: 25)
(18)   5' TpsCpoGpsTpsCpoGpsTpsTpsTpsTpsGpsTpsCpsGps
          TpsTpsTpsTpsGpsTpsCpsGpsT 3';
and (SEQ ID NO: 26)
(19)   5' TpsCpoGpsTpsCpoGpsTpsTpsTpsTpsGpsTpsCpoGps
          TpsTpsTpsTpsGpsTpsCpsGpsT 3';
``` wherein:

po represents a phosphodiester internucleotide linkage; and ps represents a phosphorothioate internucleotide linkage.

Embodiment 22a is the ODN construct of Embodiment 22, wherein the CpG ODN comprises, preferably consists of, a polynucleotide sequence that is, or is at least, 70%, 75%, 80%, 85%, 90%, 91%, 92%, 93%, 94%, 95%, 96%, 97%, 98%, 99% or 100% identical to one of SEQ ID NOs: 8-26.

Embodiment 23 is an ODN construct, having the structure of:

(1) 5' Toco-po(HEG)po(HEG)po-TpsCpoGpsTpsCpoGps
TpsTpsTpsTpsGpsTpsCpoGpsTpsTpsTpsTpsGpsTps
CpoGpsTpsT 3'; (SEQ ID NO: 27)

(2) 5' Toco-po(HEG)po(HEG)po-TpsCpsGpsTpsCpoGps
TpsTpsTpsTpsGpsTpsCpoGpsTpsTpsTpsTpsGpsTps
CpsGpsTpsT 3'; (SEQ ID NO: 28)

(3) 5' TpsCpoGpsTpsCpoGpsTpsTpsTpsTpsGpsTpsCpo
GpsTpsTpsTpsTpsGpsTpsCpoGpsTpsT-
(HEG)po(HEG)po-Toco 3'; (SEQ ID NO: 29)

(4) 5' TpsCpsGpsTpsCpoGpsTpsTpsTpsTpsGpsTpsCpo
GpsTpsTpsTpsTpsGpsTpsCpsGpsTpsT-
(HEG)po(HEG)po-Toco 3'; (SEQ ID NO: 30)

(5) 5' Chol-po(HEG)po(HEG)po-TpsCpoGpsTpsCpoGps
TpsTpsTpsTpsGpsTpsCpoGpsTpsTpsTpsTpsGpsTps
CpoGpsTpsT 3'; (SEQ ID NO: 31)

(6) 5' Chol-po(HEG)po(HEG)poTpsCpsGpsTpsCpsGps
TpsTpsTpsTpsGpsTpsCpsGpsTpsTpsTpsTpsGpsTps
CpsGpsTpsT 3'; (SEQ ID NO: 32)

(7) 5' Chol-po(HEG)po(HEG)po-TpsCpoGpsTpsCpsGps
TpsTpsTpsTpsGpsTpsCpsGpsTpsTpsTpsTpsGpsTps
CpsGpsTpsT 3'; (SEQ ID NO: 33)

(8) 5' Chol-po(HEG)po(HEG)po-TpsCpoGpsTpsCpoGps
TpsTpsTpsTpsGpsTpsCpsGpsTpsTpsTpsTpsGpsTps
CpsGpsTpsT 3'; (SEQ ID NO: 34)

(9) 5' Chol-po(HEG)po(HEG)po-TpsCpoGpsTpsCpoGps
TpsTpsTpsTpsGpsTpsCpoGpsTpsTpsTpsTpsGpsTps
CpsGpsTpsT 3'; (SEQ ID NO: 35)

(10) 5' Chol-po(HEG)po(HEG)po-TpsCpoGpsTpsCpoGps
TpsTpsTpsTpsGpsTpsCpoGpsTpsTpsTpsTpsGpsTps
CpoGpsTpsT 3'; (SEQ ID NO: 36)

(11) 5' TpsCpsGpsTpsCpsGpsTpsTpsTpsTpsGpsTpsCps
GpsTpsTpsTpsTpsGpsTpsCpsGpsTpsTps-
(HEG)po(HEG)po-Chol 3'; (SEQ ID NO: 37)

(12) 5' TpsCpoGpsTpsCpsGpsTpsTpsTpsTpsGpsTpsCps
GpsTpsTpsTpsTpsGpsTpsCpsGpsTpsTps-
(HEG)po(HEG)po-Chol 3'; (SEQ ID NO: 38)

(13) 5' TpsCpoGpsTpsCpoGpsTpsTpsTpsTpsGpsTpsCps
GpsTpsTpsTpsTpsGpsTpsCpsGpsTpsTps-
(HEG)po(HEG)po-Chol 3'; (SEQ ID NO: 39)

(14) 5' TpsCpoGpsTpsCpoGpsTpsTpsTpsTpsGpsTpsCpo
GpsTpsTpsTpsTpsGpsTpsCpoGpsTpsTps-
(HEG)po(HEG)po-Chol 3'; (SEQ ID NO: 40)

(15) 5' TpsCpsGpsTpsCpsGpsTpsTpsTpsTpsGpsTpsCps
GpsTpsTpsTpsTpsGpsTpsCpsGpsTpsTps-
(HEG)po(HEG)po-Toco 3'; (SEQ ID NO: 41)

(16) 5' Toco-po(HEG)po(HEG)po-TpsCpoGpsTpsCpoGps
TpsTpsTpsTpsGpsTpsCpoGpsTpsTpsTpsTpsGpsTps
CpoGpsTpsT 3'; (SEQ ID NO: 42)

(17) 5' TpsCpoGpsTpsCpsGpsTpsTpsTpsTpsGpsTpsCps
GpsTpsTpsTpsTpsGpsTpsCpsGpsTpsTps-
(HEG)po(HEG)po-Toco 3'; (SEQ ID NO: 43)

(18) 5' TpsCpoGpsTpsCpoGpsTpsTpsTpsTpsGpsTpsCps
GpsTpsTpsTpsTpsGpsTpsCpsGpsTpsTps-
(HEG)po(HEG)po-Toco 3'; (SEQ ID NO: 44)

(19) 5' TpsCpoGpsTpsCpoGpsTpsTpsTpsTpsGpsTpsCpo
GpsTpsTpsTpsTpsGpsTpsCpsGpsTpsTps-
(HEG)po(HEG)po-Toco 3'; (SEQ ID NO: 45)

(20) 5' TpsCpoGpsTpsCpoGpsTpsTpsTpsTpsGpsTpsCpo
GpsTpsTpsTpsTpsGpsTpsCpoGpsTpsTps-
(HEG)po(HEG)po-Toco 3'; (SEQ ID NO: 46)

(21) 5' Toco-po(HEG)po(HEG)po-TpsCpsGpsTpsCpsGps
TpsTpsTpsTpsGpsTpsCpsGpsTpsTpsTpsTpsGpsTps
CpsGpsTpsT 3'; (SEQ ID NO: 47)

(22) 5' Toco-po(HEG)po(HEG)po-TpsCpoGpsTpsCpsGps
TpsTpsTpsTpsGpsTpsCpsGpsTpsTpsTpsTpsGpsTps
CpsGpsTpsT 3'; (SEQ ID NO: 48)

(23) 5' Toco-po(HEG)po(HEG)po-TpsCpoGpsTpsCpoGps
TpsTpsTpsTpsGpsTpsCpsGpsTpsTpsTpsTpsGpsTps
CpsGpsTpsT 3'; (SEQ ID NO: 49)

(24) 5' Toco-po(HEG)po(HEG)po-TpsCpoGpsTpsCpoGps
TpsTpsTpsTpsGpsTpsCpoGpsTpsTpsTpsTpsGpsTps
CpsGpsTpsT 3'; (SEQ ID NO: 50)

(25) 5'- TpsCpoGpsTpsCGpsTpsTpsTpsTpsGpsTpsCGps
TpsTpsTpsTpsGpsTpsCpoGpsTpsTps-HEGps-
Chol 3'; (SEQ ID NO: 51)

(26) 5'-TpsCpoGpsTpsCpoGpsTpsTpsTpsTpsGpsTpsCpo
GpsTpsTpsTpsTpsGpsTpsCpsGpsTpsTps
(HEG)po(HEG)po-Chol 3'; (SEQ ID NO: 52)

(27) 5'-GpsGpsGpsGpsTpsCpsApsApsCpoGpsTpsTpsGps
ApsGpsGpsGpsGpsGpsGps-HEGps-Chol 3'; (SEQ ID NO: 53)

(28) 5'-TpsCpsCpsApsTpsGpsApsCpsGpsTpsTpsCpsCps
TpsGpsApsCpsGpsTpsTps-HEGps-Chol 3'; (SEQ ID NO: 54)

(29) 5'-TpsCpsCpsApsTpsGpsApsCpsGpsTpsTpsCpsCps
TpsGpsApsCpsGpsTpsTps-HEGps-Toco 3'; (SEQ ID NO: 55)

(30) 5' Palmitoyl-po(HEG)po(HEG)po-TpsCpoGpsTps
CpoGpsTpsTpsTpsTpsGpsTpsCpoGpsTpsTpsTpsTps
GpsTpsCpoGpsTpsT 3'; (SEQ ID NO: 56)

wherein:
Chol represents cholesterol;
Toco represents tocopherol;
Palmitoyl represents a palmitoyl group;
HEG represents $((CH_2)_2O)_6$;
po represents a phosphodiester linkage; and
ps represents a phosphorothioate linkage, wherein the tocopherol, the cholesterol, or the palmitoyl group is covalently linked to the (HEG) directly via a po or ps linkage, or indirectly via a second linker that is linked to (HEG) directly via a po or ps linkage.

Embodiment 23a is the ODN construct of embodiment 23, wherein the tocopherol, the cholesterol, or the palmitoyl group is covalently the second linker and the second linker is covalently linked to the (HEG) directly via the po or ps linkage.

Figure 28:
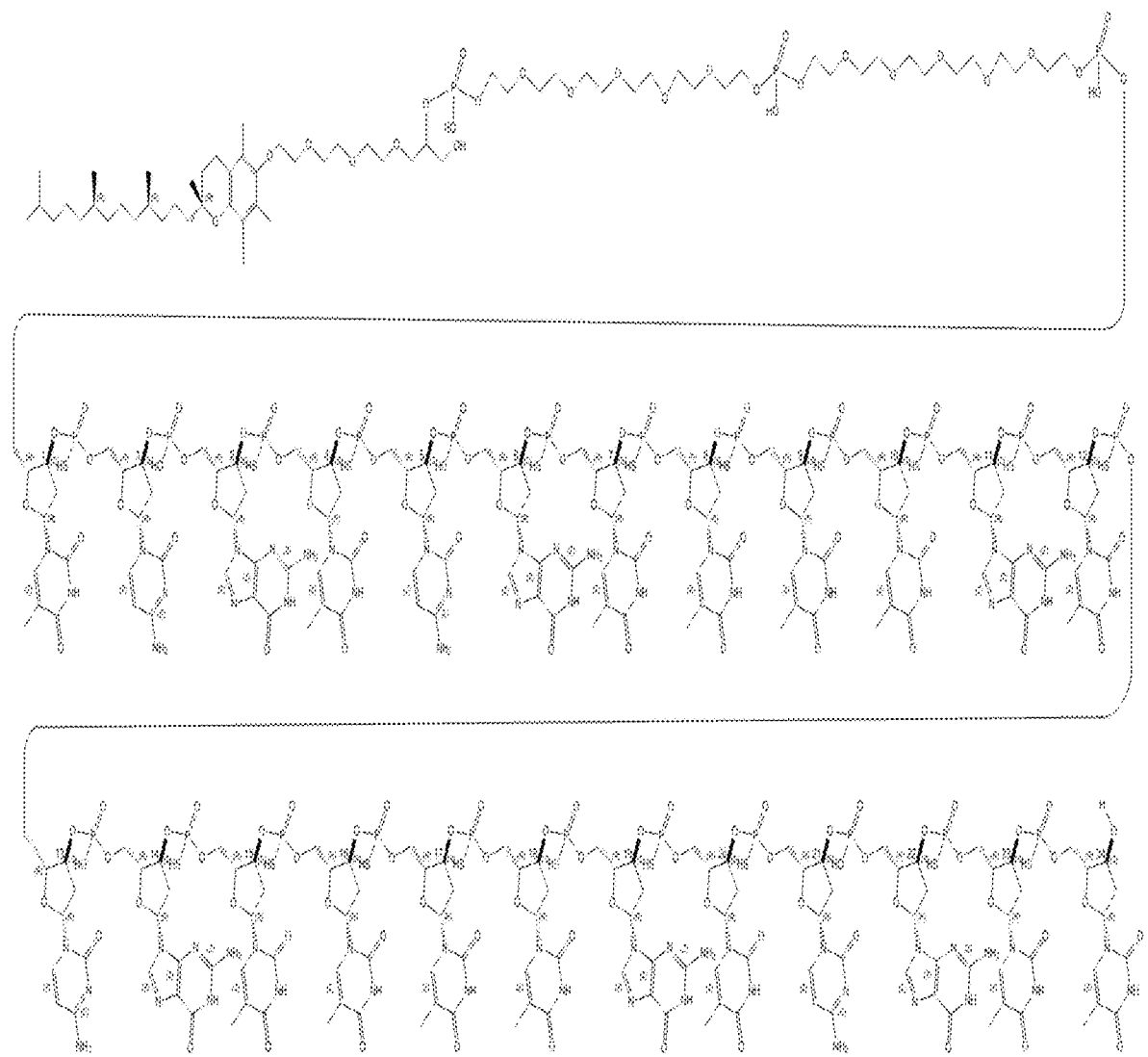
FIG. 28 shows the structure of an ODN construct.

Embodiment 23b is the ODN construct of embodiment 23, having a structure as shown in FIG. 28.

Figure 29:
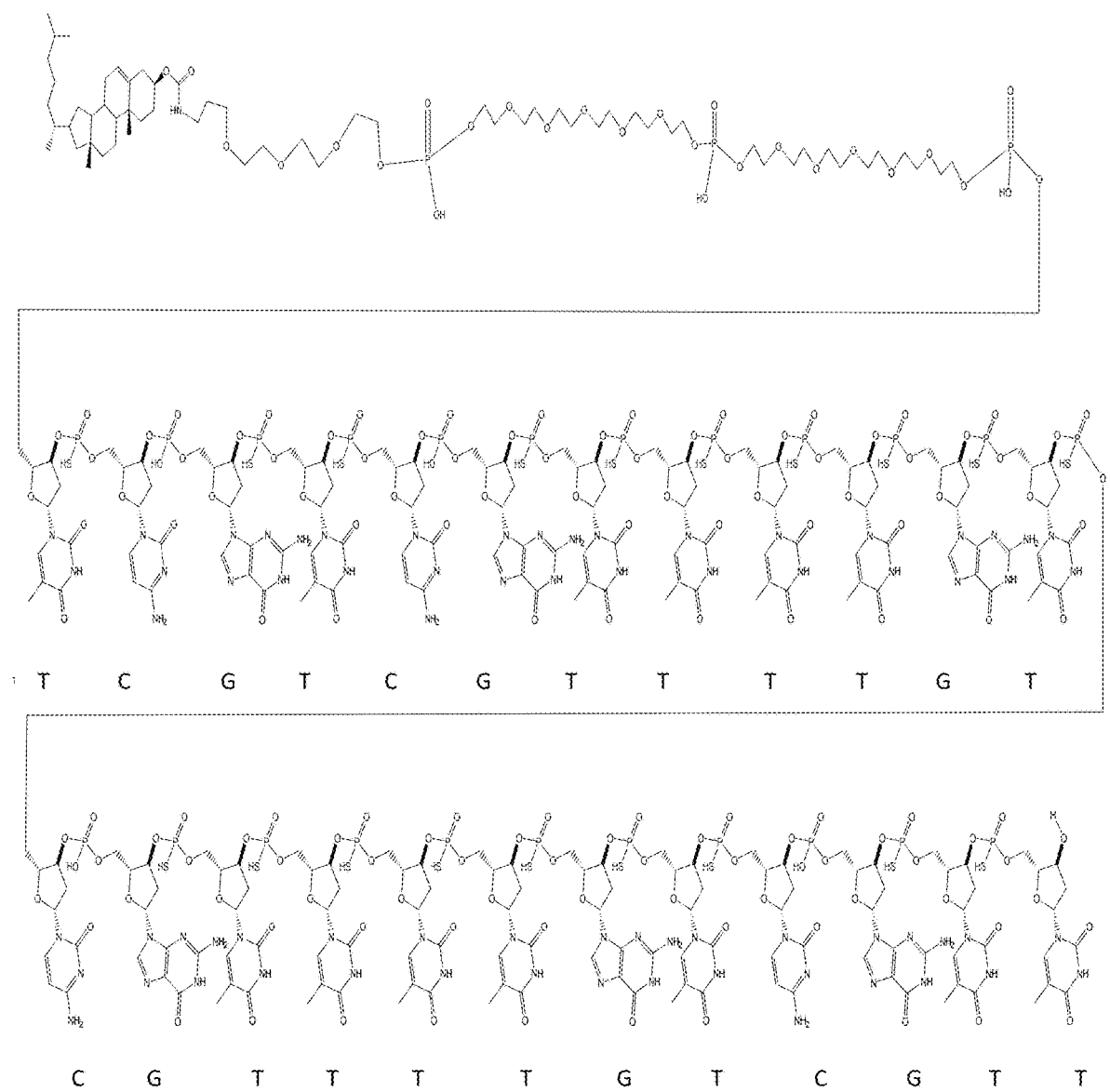
FIG. 29 shows the structure of an ODN construct.

Embodiment 23c is the ODN construct of embodiment 23, having a structure as shown in FIG. 29.

Figure 30:
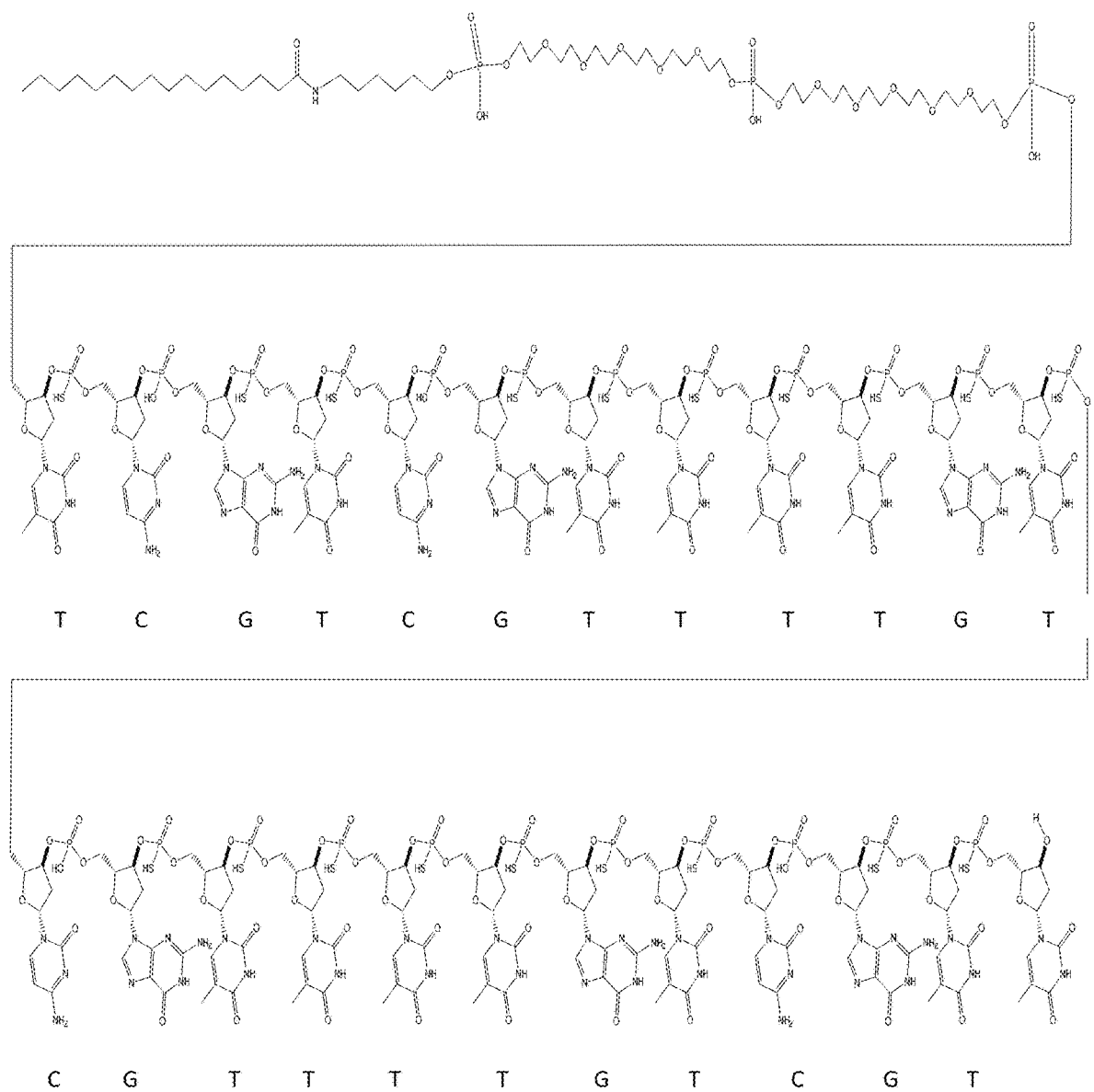
FIG. 30 shows the structure of an ODN construct.

Embodiment 23d is the ODN construct of embodiment 23, having a structure as shown in FIG. 30.

Embodiment 24 is a pharmaceutical composition comprising an ODN construct of any of Embodiments 1 to 23c and a pharmaceutically acceptable carrier.

Embodiment 25 is a method of preparing a pharmaceutical composition, comprising combining an ODN construct of any of Embodiments 1 to 23c with a pharmaceutically acceptable carrier.

Embodiment 26 is a method of stimulating an immune response in a subject in need thereof, comprising administering to the subject the pharmaceutical composition of Embodiment 24.

Embodiment 27 is a method of treating a disease in a subject in need thereof, comprising administering to the subject the pharmaceutical composition of Embodiment 24, wherein the disease is selected from the group consisting of Hepatitis B virus (HBV) and cancer.

Embodiment 28 is an ODN construct comprising a CpG ODN, wherein at least one of the CpG dinucleotides in the CpG ODN has a stereodefined phosphorothioate internucleotide linkage.

Embodiment 29 is the ODN construct of Embodiment 28, wherein two to four of the CpG dinucleotides in the CpG ODN each have a stereodefined phosphorothioate internucleotide linkage.

Embodiment 30 is the ODN construct of Embodiment 28 or 29, comprising a CpG ODN comprising a polynucleotide sequence selected from the group consisting of:

(1)    5' TCGTCGTTTTGTCGTTTTGTCGTT 3';    (SEQ ID NO: 1)

(2)    5' GGGGGACGATCGTCGGGGGG 3';    (SEQ ID NO: 2)

(3)    5' GGGGTCAACGTTGAGGGGGG 3';    (SEQ ID NO: 3)

(4)    5' TCCATGACGTTCCTGACGTT 3';    (SEQ ID NO: 4)

(5)    5' TCGTCGTTTTCGGCGCGCGCCG 3';    (SEQ ID NO: 5)

(6) and    5' TCGTCGTTACGTAACGACGACGTT 3';    (SEQ ID NO: 6)

(7)    5' TCGTCGTTTTGTCGTTTTGTCGT 3'.    (SEQ ID NO: 7)

Embodiment 31 is a ODN construct having the formula of Formula I(s):

5'M$_1$-L$_1$-[CpG ODN]-L$_2$-M$_2$3', wherein:
each of M$_1$ and M$_2$ independently represents a lipid moiety, preferably the lipid moiety comprises at least one selected from the group consisting of cholesterol, tocopherol, a palmitoyl group, and a stearyl group, optionally one of M$_1$ and M$_2$ is absent;

each of L$_1$ and L$_2$ independently represents a linker, preferably the linker comprises at least 10 atoms selected from the group consisting of carbon, nitrogen, oxygen, hydrogen, sulfur and phosphorus, and L is covalently linked to the CpG ODN via a cleavable linkage, preferably via an ester or an amide bond, optionally one of L$_1$ and L$_2$ is absent when the respective M$_1$ or M$_2$ is absent; and CpG ODN represents the CpG ODN of any of claims 28 to 30;

optionally, the CpG ODN construct of formula (I) is further covalently conjugated to a targeting moiety, which is preferably selected from the group consisting of galactose, N-acetylgalactosamine (GalNAc), fucose, mannose, sialic acid, N-acetyl neuraminic acid.

Embodiment 32 is a CpG ODN construct having a formula of:

5'M-L-[CpG ODN]3', or    Formula (IIa)(s):

5'[CpG ODN]-L-M3'    Formula (IIb)(s):

wherein:
M represents a lipid moiety, preferably the lipid moiety comprises at least one selected from the group consisting of cholesterol, tocopherol, a palmitoyl group, and a stearyl group;

L represents a linker comprising at least 1 atoms selected from the group consisting of carbon, nitrogen, oxygen, hydrogen, sulfur and phosphorus, and L is covalently linked to the CpG ODN via a cleavable linkage, preferably via an ester or an amide bond; and CpG ODN represents the CpG ODN of any of Embodiments 28 to 30;

optionally, the CpG ODN construct of Formula (IIa) or (IIb) is further covalently conjugated to a targeting moiety, which is preferably selected from the group consisting of galactose, N-acetylgalactosamine (GalNAc), fucose, mannose, sialic acid, N-acetyl neuraminic acid.

Embodiment 33 is a CpG ODN construct having a structure of:

5'M$_1$-Y$_1$—(((CH$_2$)$_2$O)$_m$—X)$_n$—Y$_2$—[CpG ODN]—Y$_3$-M$_2$3', or    Formula (IIIa)(s):

5'M$_2$-Y$_3$—[CpG ODN]—Y$_2$—(((CH$_2$)$_2$O)$_m$—X)$_n$—Y$_1$-M$_1$3'    Formula (IIIb)(s):

wherein:
M$_1$ represents a lipid moiety, preferably the lipid moiety comprises at least one selected from the group consisting of cholesterol, tocopherol, a palmitoyl group, and a stearyl group, M$_2$ represents a lipid moiety, a targeting moiety, or is absent, Y$_1$ is a bond or a linker, preferably ethylene glycol having the formula ((CH$_2$)$_2$O)$_o$, wherein o is 1-15, covalently linked to (((CH$_2$)$_2$O)$_m$—X)$_n$ via a phosphodiester (po) linkage, a phosphorothioate (ps) linkage or a bond, X is independently a bond, a po linkage or a ps linkage, each of Y$_2$ and Y$_3$ is independently a cleavable linkage, preferably comprises an ester or an amide bond, more preferably is a po linkage or a phosphoramidate linkage, most preferably a po linkage, provided that when M$_2$ is absent, Y$_3$ is absent, CpG ODN represents the CpG ODN of any of embodiments 28 to 30;
m is an integer from 1 to 15, and
n is an integer from 1 to 5.
Embodiment 34 is a CpG ODN construct having a formula of:

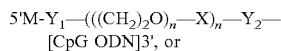   Formula (IVa)(s):

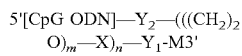   Formula (IVb)(s):

wherein:
M represents a lipid moiety, preferably the lipid moiety comprises at least one selected from the group consisting of cholesterol, tocopherol, a palmitoyl group, and a stearyl group,
$Y_1$ is a bond or a linker, preferably ethylene glycol having the formula $((CH_2)_2O)_o$, wherein o is 1-15, covalently linked to $(((CH_2)_2O)_n-X)_n$ via a phosphodiester (po) linkage, a phosphorothioate (ps) linkage or a bond,
X is independently a bond, a phosphodiester (po) linkage or a phosphorothioate (ps) linkage,
$Y_2$ is a cleavable linkage, preferably comprises an ester or an amide bond, more preferably comprises a po linkage or a phosphoramidate linkage, most preferably a po linkage;
CpG ODN represents the CpG ODN of any of embodiments 28 to 30
n is an integer from 1 to 5, preferably 2;
optionally, the CpG ODN construct of Formula (IVa) or (IVb) is further covalently conjugated to a targeting moiety, which is preferably selected from the group consisting of galactose, N-acetylgalactosamine (GalNAc), fucose, mannose, sialic acid, N-acetyl neuraminic acid.
Embodiment 35 is a pharmaceutical composition comprising the ODN construct of any of Embodiments of 28 to 34.
Embodiment 36 is a method of preparing a pharmaceutical composition, comprising combining the ODN construct of any of Embodiments of 28 to 24 with a pharmaceutically acceptable carrier.
Embodiment 37 is a method of stimulating an immune response in a subject in need thereof, comprising administering to the subject the pharmaceutical composition of Embodiment 35.
Embodiment 37a is the method of embodiment 37, wherein the subject is in need of treatment of an HBV infection.
Embodiment 37b is the method of embodiment 37, wherein the subject is in need of treatment of a cancer.
Embodiment 37c is the method of embodiment 37, wherein the subject is in need of treatment of a colorectal cancer.
Embodiment 38 is a method of treating a cancer in a subject in need thereof, comprising administering to the subject the pharmaceutical composition of Embodiment 35.
Embodiment 38a is the method of embodiment 38, wherein the cancer is a gastrointestinal cancer.
Embodiment 38b is the method of embodiment 38, wherein the cancer is a colorectal cancer.
Embodiment 39 is a method of treating an HBV infection in a subject in need thereof, comprising administering to the subject the pharmaceutical composition of Embodiment 35.
Embodiment 39a is the method of embodiment 39, wherein the treatment results in a reduction of the copy numbers of the HBV DNA in the subject.

Embodiment 39b is the method of embodiment 39 or 39a, wherein the treatment results in an increase in the titer of antibody specific to Hepatitis B surface antigen (HBSAg) in the subject.
Embodiment 39c is the method of any one of embodiments 39 to 39b, wherein the treatment results in an increase in Hepatitis B surface antigen (HBSAg) specific T cells.

EXAMPLES

The following examples of the present disclosure are to further illustrate the nature of the present disclosure. It should be understood that the following examples do not limit the present disclosure and that the scope of the present disclosure is to be determined by the appended claims.
The experimental methods used in the following examples, unless otherwise indicated, are all ordinary methods. The reagents used in the following embodiments, unless otherwise indicated, are all purchased from ordinary reagent suppliers.

Example 1

Synthesis of AG9

Figure 31:
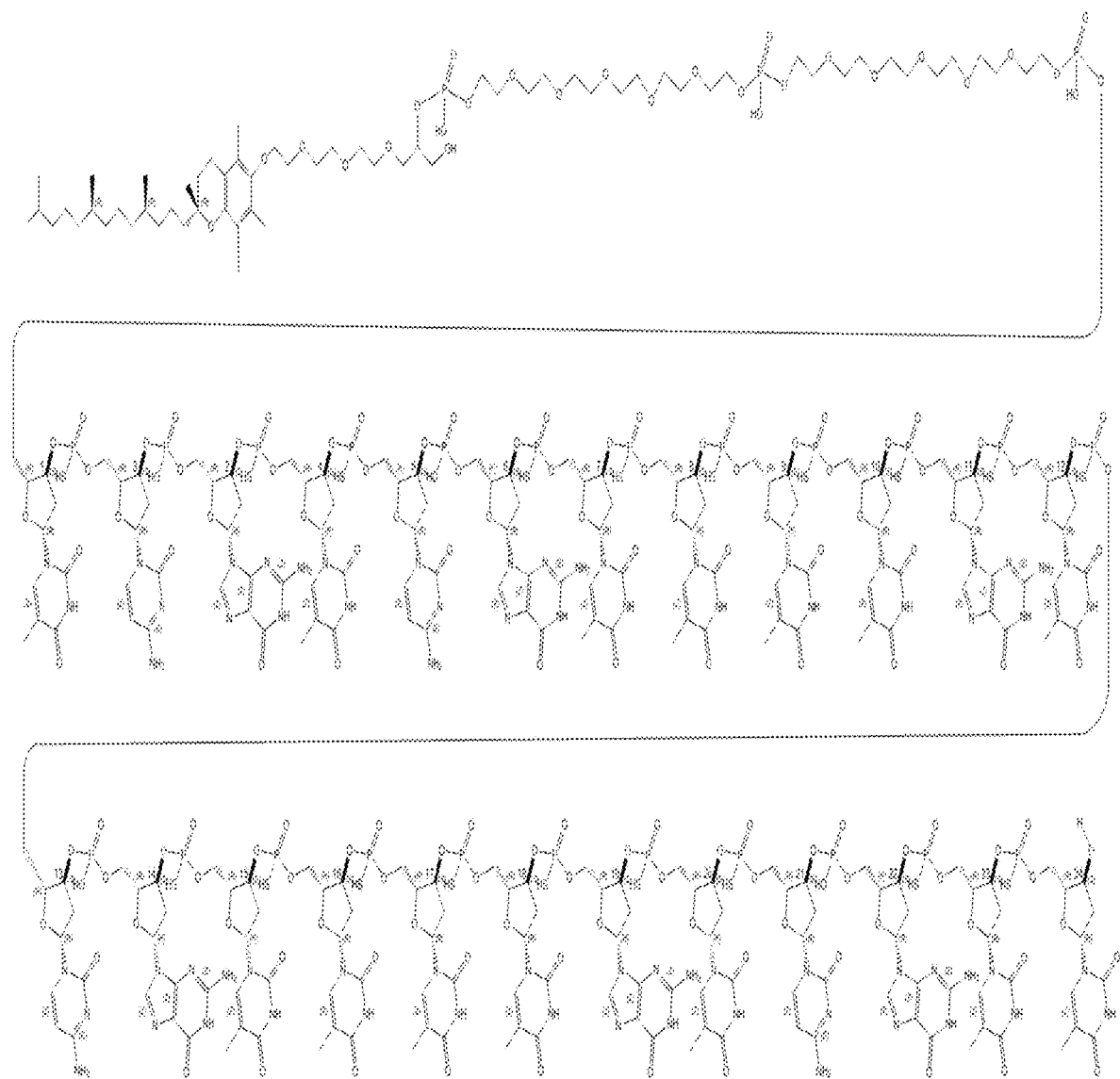
FIG. 31 shows the structure of an ODN construct.

AG9: Chemical Formula: C298H420N70O164P26S19, Molecular Weight: 9021.42 (5'-Toco-(po)-HEG(po)-HEG(po)-TpsCGpsTpsCGpsTpsTpsTpsTpsGpsTpsCGpsTpsTpsTpsTpsGpsTpsCGpsTpsT-3') as shown in FIG. 31.
AG9 was synthesized using a synthesis scheme illustrated in FIG. 17. More specifically, synthesis of AG9 was performed utilizing solid phase synthesis technology and an automated synthesizer. The synthesis was performed two times at a 218 umol scale for a total scale of 436 umol. The synthesis was performed using a fixed 6.3 ml column (GE healthcare). The OligoPilot 100 was used for the synthesis of the compound. Unylinker NittoPhase support with a loading of ~303 μmol/g was the solid support used for this synthesis. The synthesis was executed by running a 4-step iterative method specifically designed for the manufacture of AG9. The four steps include detritylation, coupling, sulfurization, and capping, and were repeated for 16 cycles using the specific amidites to yield the desired product. After each step, an appropriate wash of acetonitrile was performed to prevent unwanted reactions. The detritylation of the solid support was performed utilizing 3% dichloroacetic acid in toluene and monitored at 436 nm. Coupling was performed by mixing 40% (by volume) of a 0.1 M amidite solution with 60% of the activator in-line prior to addition to the column. The total of 2.5 equivalents of the amidite added per coupling. After loading the activator/amidite mixture onto the column, the coupling mixture was circulated via a recycling loop for 5 minutes for DNA. The α-Tocopherol phosphoramidites was dissolved in 10% DMF in Acetonitrile. An extended coupling of 10 min were used for HEG linker and α-Tocopherol phosphoramidites. To ensure high coupling efficiency, the amidite and activator solutions remained over molecular sieves for at least 4-6 hours after preparation. The third step, sulphurization, was performed by the addition of 1.2 column volumes of a solution of 0.2 M Phenyl acetyl disulfide (PADS) in lutidine: acetonitrile (1:1). The solution was allowed to age at least 12 hours prior to use in the synthesis. A contact time of 2.0 minutes with 2.0 CV for thiolation was performed. For oxidation, the 0.05 M Iodine in Pyridine/Water 90/10 was used The last step in the elongation cycle, capping, was performed by the addition of one half of the column volume of a mixture of the three capping reagents (Capping A: Capping B1: Capping B2; 50/25/25; v/v/v).

After the full-length AG9 sequence was synthesized, the support was washed with 2.0 CV of 20% Diethylamine (DEA) in acetonitrile. This step allowed for removal of the beta cyanoethyl protecting groups from the product while the product was still attached to the support.

TABLE 1

List of Synthesis Reagents and Vendors

| Synthesis Reagent | Vendor | MST# |
|---|---|---|
| dA 5'-O-DMT-β-Cyanoethyl Phosphoramidite | Thermo | 21-1732-75 |
| dC 5'-O-DMT-β-Cyanoethyl Phosphoramidite | Thermo | 21-1727-75 |
| dG 5'-O-DMT-β-Cyanoethyl Phosphoramidite | Thermo | 21-1734-75 |
| T 5'-O-DMT-β-Cyanoethyl Phosphoramidite | Thermo | 21-1736-75 |
| HEG-phosphoramidites | Thermo | 27-1786-02 |
| α-Tocopherol phosphoramidites | Chemgenes | CLP-2706 |
| NittoPhase Unylinker Support | Kinnovate | — |
| Acetonitrile (50 lit) | TEDIA | UN1648 (AH3801-130) |
| Cap A Solution 20% Methylimidazole/80% ACN | Novabiochem | BIO224-1005 |
| Cap B1 Solution 40% Acetic Anhydride, 60% ACN | Novabiochem | BIO347-0505 |
| Cap B2 Solution 60% 2,6 - Lutidine/40% ACN | Novabiochem | BIO349-0505 |
| 0.2M PADS in Lutidine: Acetonitrile (1:1) | AIC | |
| Lutidine | Sigma | N/A* |
| 20% Diethylamine (DEA) | Novabiochem | NC0017-0505 |
| 3% Dichloroacetic Acid (DCA) in Toluene | Novabiochem | BIO832-2505 |
| Oxidizing agent (0.05M Iodine in Pyridine/Water 90/10 | Novabiochem | BIO424-2505 |
| Activator Solution: 0.3M 5-Benzylmercaptotetrazole (BTT) in Acetonitrile | Novabiochem | BIO166-1005 |

*

| Variables | Value |
|---|---|
| Column Volume (CV) | 6.3 mL |
| Amidites (equiv./flow) | 2.5 equiv |
| Activator (flow) | 300 mL/min |
| DNA Thiolation (equiv./flow) | 2.5 equiv |
| HEG coupling (equiv./time) | 3.0 equiv/10 min coupling |
| Tocopherol Coupling (equiv./time) | 3.0 equiv/10 min coupling |
| Capping solutions | 0.5 CV, 0.5 min CT |
| DEA Treatment | 1.2.0 CV, 10 min CT |

0.7 g of the Unylinker™ resin was filled into the Akta 6.3 mL column and the column was placed into the column position 1. The flow through the column and potential leakages of the column were checked by the Flow Test.

Cleavage and deprotection of the synthesized oligonucleotide was performed using concentrated ammonium hydroxide. Ammonium hydroxide (~60 ml) was added to the oligonucleotide bound to the solid support and gently stirred until the support was well dispersed. The mixture was shaken at 55° C. for approximately 16 hours. After the allotted time elapsed, the solid support was separated from the product containing solution by filtering through a sintered glass filter. The solid support in the filter was then washed (3×20 ml) with a solution of 50:50 (v/v) Ethanol:H₂O. A small aliquot of the crude oligonucleotide solution was removed for mass spectral, HPLC, and UV analysis.

Purification was performed using Reverse phase chromatography on a Akta Pur HPLC system (GE Healthcare) and a Luna C8 phenomenox Column 250*21.2 with an internal diameter of 21.2 cm.

List of Purification Reagents and Vendors

| Purification Reagent | Vendor | MST# |
|---|---|---|
| Sodium Acetate (NaCl) | EMD | |
| Luna C8 phenomenox Column 250*21.2 | phenomenox | 00G-4249PO |
| 20 mM Sod Acetate, 10% AcCN (Eluent A) | | |
| Acetonitrile (Eluent B) | | |

After sample loading, the column was equilibrated for 2 column volumes (CV) of Eluent A. The gradient consisted of an initial segment in which 8% Eluent B was delivered over 2.0 CV in order to wash off any unbound sample from the column and then the gradient was run from 8% to 50% Eluent B over a length of 6.0 CV. Fractions were collected in sterile 50 ml vials and then analyzed by HPLC.

Purification Conditions

| Variable | Specification |
|---|---|
| Column | Luna C8 phenomenox Column, 21.2 cm diameter |
| Anion Exchange Resin | C8, 100 μm particle size |
| Column Bed Height | 21.2 cm |
| Column Volume | 75 ml L |
| Eluent A | 20 mM NaOAc, 10% AcCN |
| Eluent B | AcCN |
| Inlet temperature | RT |
| Outlet temperature | RT |
| Loading Flow Rate | 30 ml/min |
| Flow Rate | 30 ml/min |
| Gradient Wash | 8% B for 1.0 CV |

| Variable | Specification |
|---|---|
| Gradient | 8% B to 50% B over 6.0 CV |
| Fraction size | ~30 ml |

Once the fraction data was complete, mock pools were prepared. The mock pools contained all fractions greater than 75% FLP. After analysis, these same fractions were pooled for desalting by ultrafiltration.

The crude product, fractions, mock pools, pools, desalted product and final product were analyzed by RP-HPLC. The crude and final product was also analyzed by LCMS. The methods were as follows:

RP-HPLC Analysis of AG9
ESI/MS Analysis of AG9

The selected pools for each purified synthesis batch, which had remained separate up to that point, were combined for the ultrafiltration. The combined pools were subjected to concentration and desalting using ultrafiltration with a total of three 0.1 m² PES membranes (Pall Corp). The pools were concentrated to approximately 2 liters at which point diafiltration was initiated. Diafiltration continued until the conductivity of the permeate was less than or equal to 50 μS/cm.

Lyophilization was performed using a VirTis SP Scientific Bench Top Pro Freeze Dryer System. The concentrated solution was filtered through a 0.2-micron filter then evenly distributed into 50 ml vials and lyophilized. The final product was sampled by QC and ready for in vivo testing.

Example 2

TLR9 Activation Assays

HEK293 Reporter Assay

HEK-Blue hTLR9 and HEK-Blue mTLR9 cell lines are commercial cell lines (Invivogen, San Diego, Calif.) that are stably transfected with a reporter construct NF-kB-SEAP (secreted embryonic alkaline phosphatase), and either human TLR9 or mouse TLR9.

24 hours before starting the assay, a subconfluent layer of cells is plated in a 96-well, flat bottom dish. On the day of the assay, titrating concentrations of compound to be analyzed are added to the cells, and the cultures are incubated overnight. In these cells, the ability of the compound to activate the receptor TLR9 is proportional to the concentration of the reporter molecule, SEAP, in the supernatant. The concentration of SEAP can be determined by a colorimetric assay where the substrate QUANTI-Blue (Invivogen) is added to the culture supernatant for 3 hours. Cleaved substrate is detected using a spectrophotometer at OD630 nm, and relative concentrations are compared.

PBMC Assay

PBMCs are isolated from whole blood by ficoll gradient centrifugation. $1\times10^6$ PBMC are seeded at the bottom of 96-well culture dishes, and titrating concentrations of compound to be analyzed are added to the cells. Cultures are incubated for 48 hours, during which cellular targets are induced to express cytokines. Cytokine levels are measured by sampling supernatant and detecting individual cytokines using a Luminex assay. In addition, PBMCs are harvested and stained using fluorochrome-conjugated antibodies directed to individual receptors. Expression levels are measured using a flow cytometer.

PHH Cell Assay

Primary human hepatocytes are cultured and infected with Hepatitis B. On day 4 post infection, the media is exchanged for media from PBMCs treated with compound (see above). After 4 days of further incubation (day 8 post infection), the media is changed and the supernatant is measured for HBsAg production. After 4 more days (day 12 post infection), the supernatant is again measured for HBsAg production.

In Vivo Cytokine Induction

C57BL/6 mice are injected subcutaneously or intravenously with compound to be analyzed. Four hours later, mice are bled by submandibular vein puncture. Serum cytokines are measured using a Luminex assay.

AAV-HBV Model

C57BL/6 mice are infected with AAV-HBV particles. Approximately 1 month after infection, mice are injected subcutaneously or intravenously with compound to be analyzed. Compound dosing is repeated biweekly (every two weeks) for a specified period of time, typically over 8 weeks. Mice are bled weekly. Serum is measured for various endpoints, such as circulating HBsAg, HBV DNA and anti-HBs Ab.

MC38 Tumor Model

C57/BL6 mice are subcutaneously implanted with $0.5\times 10^6$ MC38 colon carcinoma cells, and tumor growth is monitored. When the mean tumor volume reaches 100-200 mm³ (approximately 12 days past implantation), dosing is initiated. Tumor size is monitored every 3-4 days.

ELISpot Procedure

Fresh spleen cells were isolated from treated mice that were sacrificed on predetermined time points, approximately 1 month after the final dose. Splenocytes were aliquoted in triplicate into microtiter plate wells at a concentration of $2\times10^5$ cells/well. Individual known HBV epitopes from core and surface and 15-mer overlapping peptides from HBV consensus B, C & D (overlapping by 11 amino acids) were added to the wells at a final concentration of 2 μg/ml. Cells were incubated for varying amounts of time, then activated cells were revealed by Mouse IFN-γ ELISpot kit (Mabtech 3321-2A) according to manufacturer's instructions. Activated cells were quantified by CTL-FluoroSpot Analyzer.

IVIS imaging

For in vivo imaging, C57Bl/6 male mice between 7-8 weeks were used. AF647-labeled CpG oligonucleotides (AG20 and AG21) were injected via either intravenous or subcutaneous routes (20 nmol in total volume of 100 μl). 24 hours post injection, animals were sacrificed and spleens, draining lymph nodes, livers, kidneys and lungs were excised. The organs were imaged using IVIS (Ami HTX). Image sets (Ex: 605, Em: 670, f 5, 10 Sec) were collected. Spectral Instruments Imaging Software Aura was used to acquire and quantitate the fluorescence imaging data sets. A Region of Interest tool was used to measure the radiant efficiency from each organ.

Immunofluorescence

C57Bl/6 male mice between 7-8 weeks were used. AF647-labeled CpG oligonucleotides (AG20 and AG21) were injected via either intravenous or subcutaneous routes (20 nmol in total volume of 100 μl). 24 hours post injection, animals were sacrificed and spleens, draining lymph nodes, livers, kidneys and lungs were excised. Organs were formalin fixed, then sectioned on a microtome using standard procedures. Immunofluorescence staining was performed using Leica Bond automated immunostainer on formalin-fixed paraffin-embedded (FFPE) mouse lymph node and spleen. Heat induced antigen retrieval was performed using Leica Bon Epitope Retrieval Buffer 2 (EDTA solution, pH9.0) for 20 minutes. Staining was performed with an overnight incubation for primary antibodies, a rat anti-CD45R (B220) (RA3-6B2), eFluor 570 antibody and rabbit anti-CD3 antibody. A secondary antibody, Goat-anti Rabbit IgG Alexa Fluor Plus 488 was applied and slides were mounted with DAPI in Fluprogel II for nuclear visualization.

HPLC and Serum Protein Binding

An Ultimate-3000 HPLC system equipped with both UV and fluorescence detectors was used for the analysis. Samples of oligonucleotides, proteins, and oligonucleotide—protein mixtures were prepared in 1×PBS with 20 mM KCL and analyzed by size-exclusion chromatography. For micelle formation assays, oligonucleotides were prepared in a solution of 2M or 4M urea or PBS. Samples were injected on a Superdex 75 Increase (GE Healthcare). A mobile phase of 1×PBS with 20 mM. KCL at 0.075 ml/min was used for the chromatography and the size-exclusion column was kept at room temperature. UV chromatograms were recorded at 260, 280 and 500 nm. The excitation wavelength of 490 nm and emission wavelength of 530 nm were used to obtain chromatograms by the fluorescence detector.

Example 3

Phosphodiesters in a CpG ODN Potentiated Activity

Based on the literature, the prototypic 5'-TCGTCGTTTTGTCGTTTTGTCGTT-3' (ODN2006) can stimulate human and mouse cells expressing TLR9. This sequence has a phosphorothioate (ps) backbone for in vivo stability. The ps linkages at the CpG motifs of ODN2006 (5'-TCGTCGTTTTGTCGTTTTGTCGTT-3') were replaced with phosphodiester (po) linkages, and TLR9 activation was assessed. The results, depicted in FIG. 1, demonstrate that replacement of 3 or 4 of the CpG motifs' ps linkages with po linkages resulted in highly active ODN constructs having agonistic activity for TLR9. The version of ODN2006 having all four of the CpG motifs' ps linkages replaced with po linkages (AG1) has an EC50 value 2-3× lower than that of ODN2006, and a maximum activity 20-35% greater than ODN2006. Similar activity to AG1 was observed for AG2 and AG3 which have 3 CpG motifs' ps linkages replaced with po linkages. This experiment demonstrates that substituting po at the backbone of the CpG motifs enhances the agonistic properties of the oligonucleotide.

Example 4

Direct Cholesterol Linkage to a CpG ODN Abrogated Activity

The oligonucleotides were conjugated to various moieties that would allow for differential distribution of the oligo. For example, cholesterol and tocopherol are lipophilic molecules that are believed to localize to the liver. When cholesterol and tocopherol were directly conjugated to either the 5' or 3' end of the CpG ODN, the resulting molecule did not activate TLR9-expressing cells (data not shown). These experiments demonstrated that direct conjugation of a compound onto the end of the oligonucleotide could impact its ability to agonize TLR9.

Example 5

Cholesterol Indirectly Conjugated Via a Cleavable Linker to a CpG ODN Potentiated Activity Due to possible steric effects, conjugation of a lipophilic moiety proximal to the oligonucleotide may have abrogated the ability of the molecule to bind to the TLR9 receptor. To explore this possibility, cholesterol was conjugated to ODN constructs having agonistic activity for TLR9, also referred to herein as a TLR9 agonists, as a targeting moiety using a cleavable linker, and TLR9 activation was assessed. The results, shown in FIG. 2, indicate that conjugation of a targeting moiety to the TLR9 agonists via a cleavable linker preserves their agonistic activity.

Figure 2:
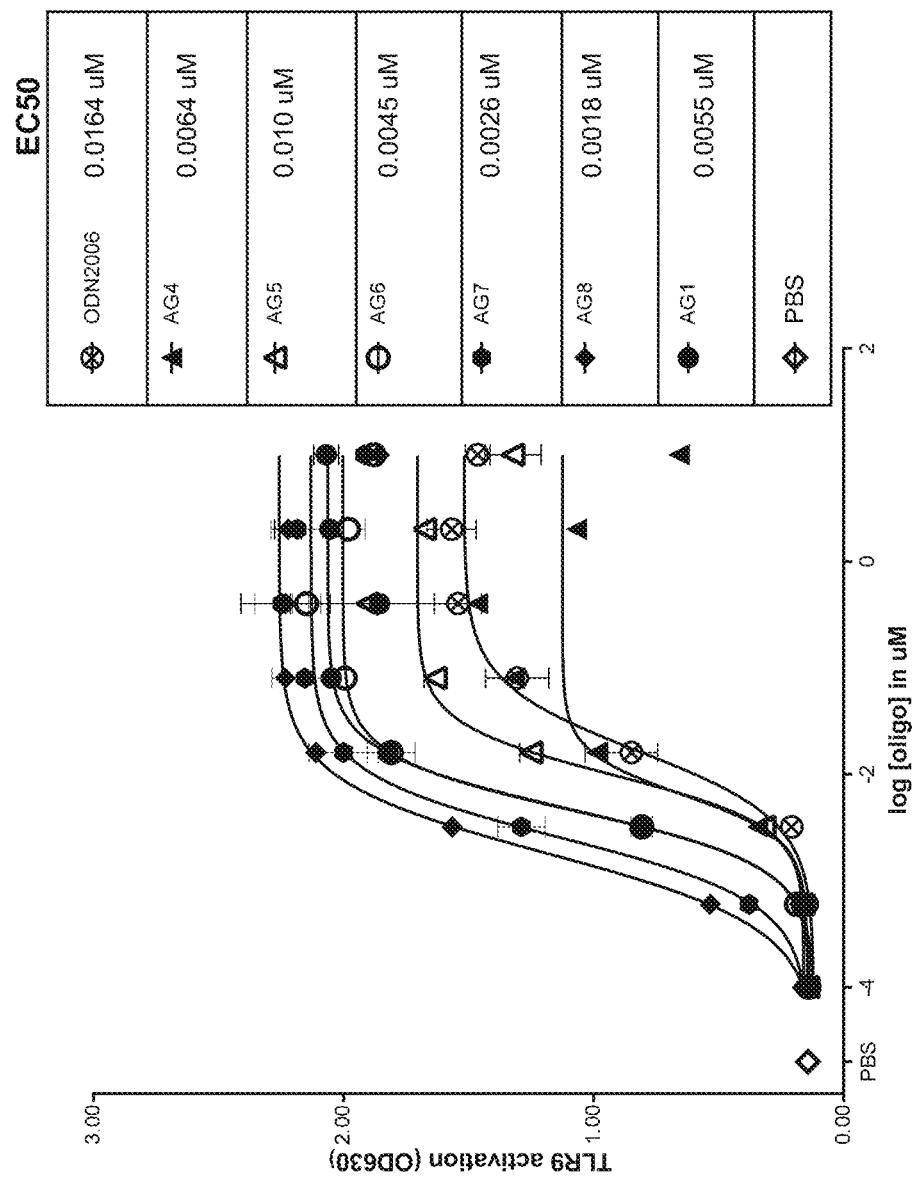
FIG. 2 shows TLR9 activation of a reporter cell line, measured by OD630 level, by ODN constructs according to embodiments of the present disclosure comprising phosphodiester-linked CpG motifs conjugated to cholesterol by a cleavable linker.

For example, a TLR9 agonist referred to as AG8 was designed using a cleavable linker to separate cholesterol from the CpG ODN of AG1. The linker for AG8 was (HEG)po(HEG)po-. When HEK-Blue hTLR9 cells were stimulated with AG8, the activity was potentiated, relative to the unconjugated parent, AG1. AG8 had an EC50 value 2-3× lower than that of AG1, and more than 9× lower than that of ODN2006. The maximum activity of AG8 was approximately 10% greater than that of AG1, and approximately 50% greater than that of ODN2006. We tested analogs of AG1 that were linked to cholesterol in the same manner as AG8. AB4, AG5, AG6 and AG7 have 0, 1, 2, and 3 (respectively) CpG motifs' ps replaced with po. As shown in FIG. 2, the higher the number of CpG motifs with po linkages, the greater the activity. AG4 has a full ps backbone and is conjugated to cholesterol via an indirect linker. AG5 is similar to AG4, but has 1 CpG motif replaced with a po linkage. These two compounds have similar activity in the HEK-Blue hTLR9 cellular assay, with their EC50 being 6.4-10 nM. AG6 and AG7 have 2 and 3 CpG motifs replaced with a po linkages, and their EC50's were approximately 4.5 nM and 2.6 nM respectively. This experiment demonstrated that by conjugated a targeting moiety indirectly through a cleavable linker, the activity of the pharmacophore was preserved.

Example 6

Tocopherol Indirectly Conjugated Via a Cleavable Linker a CpG ODN Potentiated Activity In order to test the versatility of the conjugation strategy, tocopherol was conjugated to a TLR9 agonist using a cleavable linker. For example, the TLR9 agonist referred to as AG9, the synthesis of which is described in Example 1 above, was designed using a cleavable linker to separate tocopherol from the oligonucleotide of AG1. The linker for AG9 was (HEG)po(HEG)po-. When HEK-Blue hTLR9 cells were stimulated with AG9, the activity was equivalent to that of the cholesterol conjugate AG8 (data not shown). These experiments demonstrated that different targeting moieties could be conjugated to the CpG ODN, and the CpG ODN could retain activity.

Example 7

Indirect Conjugation Using a Cleavable Linker on Either the 5' or the 3' End of a CpG ODN Resulted in Equivalent Activity In order to test the polarity of the conjugated moiety, cholesterol or tocopherol was conjugated to the 3' end of a TLR9 ODN using a cleavable linker. For example, a TLR9 agonist referred to as AG10 was designed using a cleavable linker, -po(HEG)po(HEG), to separate cholesterol from the 3' end of the oligonucleotide of AG1, and a TLR9 agonist referred to as AG11 was designed using a cleavable linker, -po(HEG)po(HEG), to separate tocopherol from the 3' end of the oligonucleotide of AG1. The activity of the conjugates was analyzed using the HEK-BLUE hTLR9. As shown in FIG. 3, AG8 and AG10, which had a cholesterol indirectly conjugated to the 5'- or 3'-ends of the CpG ODN respectively, had equivalent activity.

Interestingly, in HEK-BLUE hTLR9 cells, AG10 and AG11 had similar activity as their 5' conjugate counterparts, AG8 and AG9, respectively. However, they were not active on HEK-BLUE mTLR9 cells, indicating that the polarity of the conjugate is important for recognition by the mouse TLR9 receptor but not for the human TLR9 receptor (AG8 and AG10 are shown in FIG. 3, data not shown for AG9 and AG11).

Figure 12:
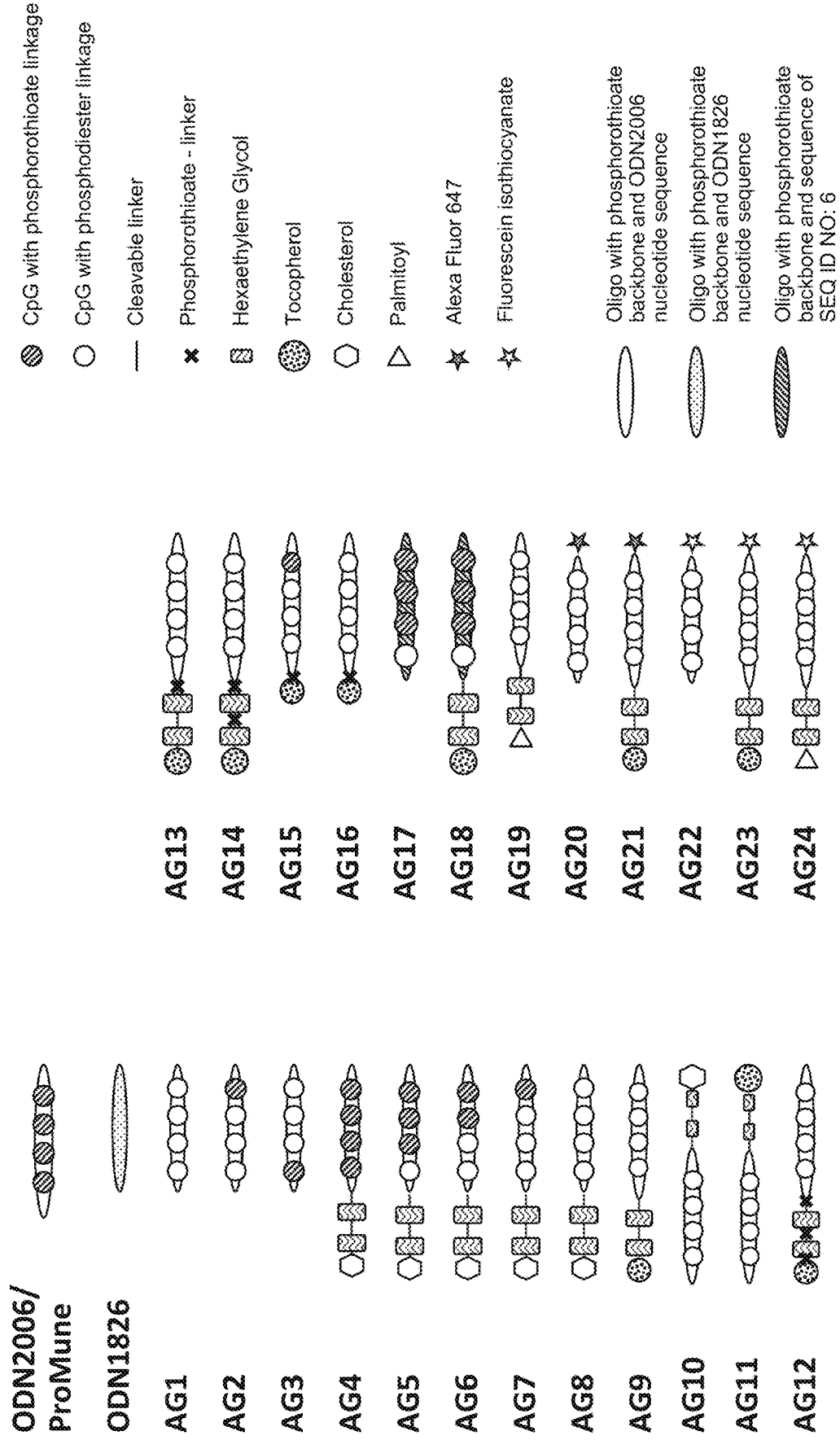
FIG. 12 illustrates exemplary ODN constructs according to embodiments of the present disclosure.

In order to test the effects of the cleavage sites within the linker, analogs of AG9 were synthesized in which the phosphodiester cleavage sites were replaced with phosphorothioate bonds that are resistant to cleavage. As illustrated in FIG. 12, AG12 has non-cleavable phosphorothioate linkages replacing the cleavable phosphodiester linkages between the oligo and the linker, between the tocopherol moiety and the linker, and between the HEG molecules of the linker. It is thought that this molecule cannot be efficiently cleaved, and the complete molecule will interact with TLR9. AG13 has non-cleavable phosphorothioate linkers replacing the cleavable phosphodiester linkages between the linker and oligo. It is thought that after cleavage, part of the linker remains bound to the oligo. AG14 has non-cleavable phosphorothioate linkers replacing the cleavable phosphodiester linkages between the linker and tocopherol. It is thought that after cleavage, tocopherol is removed and the entire linker remains bound to the oligo. AG16 is a variant of AG1 that is conjugated to tocopherol via a phosphorothioate bond. AG15 is a variant of AG that is conjugated to tocopherol via a phosphorothioate bond and that has a phosphorothioate linkage between bases 21 and 22.

Figure 19:
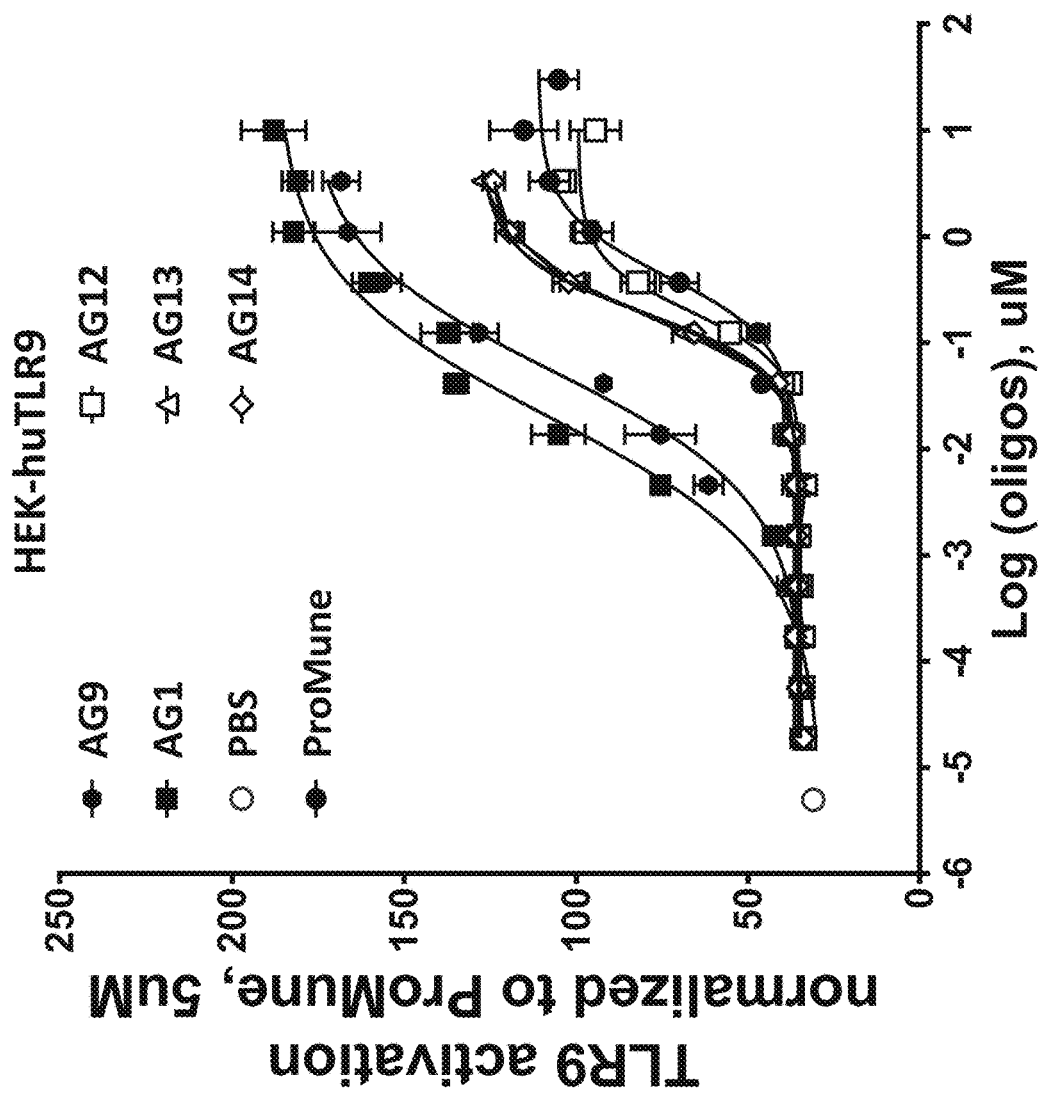
FIG. 19 shows activation of human TLR9 in a reporter cell line, normalized to ProMune, by ODN constructs according to embodiments of the present disclosure.
Figure 20:
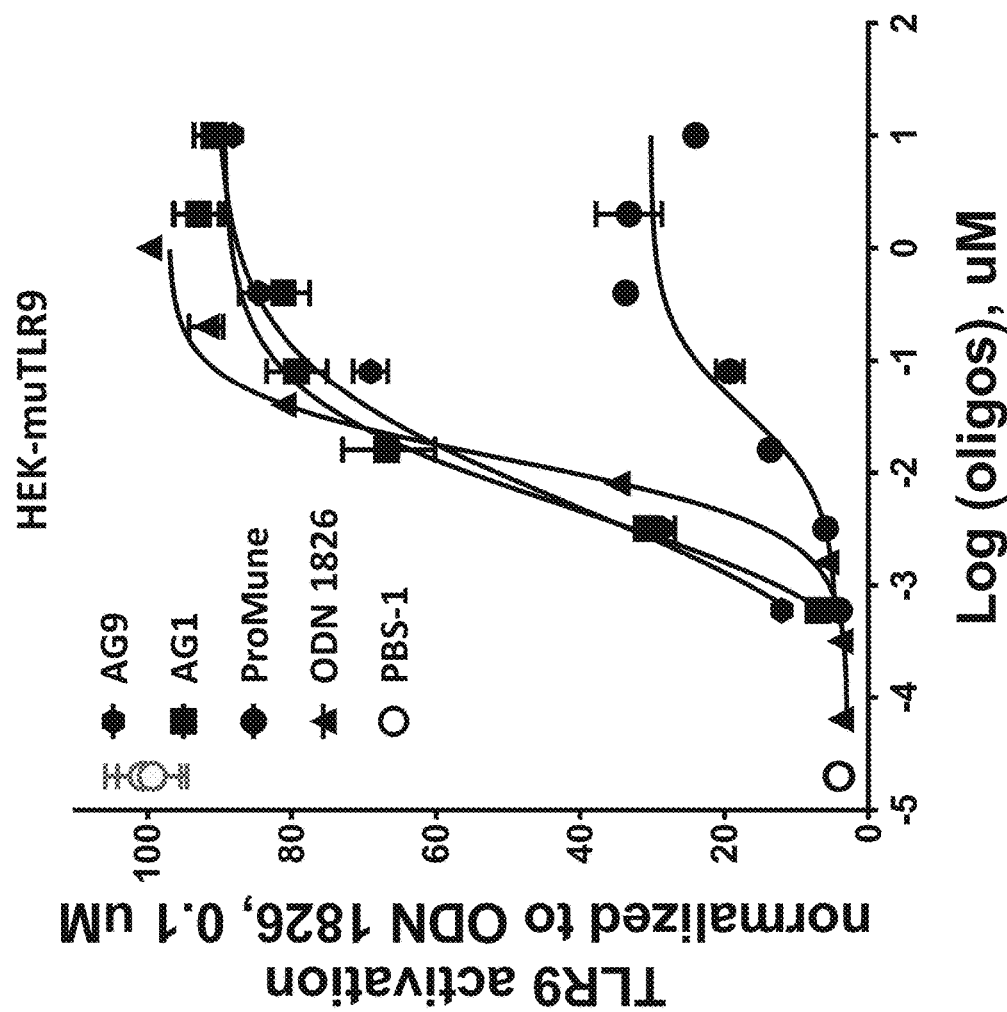
FIG. 20 shows activation of mouse TLR9, normalized to ODN1826, by ODN constructs according to embodiments of the present disclosure.

All analogs that retained any portion of the linker and/or tocopherol had reduced activity in the HEK-Blue reporter assay, as shown in FIGS. 19 and 20. In particular, it was shown that direct conjugation of a targeting moiety (such as tocopherol) to an oligo as represented by the constructs AG15 and AG16 abrogated the TLR9 agonist activity of the oligo (data not shown). Conjugation of the oligo to tocopherol via a cleavable linker preserved the TLR9 agonist activity of the oligo, and optimal activity was obtained when both tocopherol and the linker were cleaved (FIG. 19). The data suggest that once endocytosed by the cell, the ODN is released by cleavage from the linker and targeting moiety, and that this release is require for full activity. Similar results were obtained with cholesterol or palmitic acid were conjugated to the oligo by this method. The results suggest that any molecule, such as a peptide, protein, toxin, organic or inorganic molecule, etc., can be conjugated to the oligo using this cleavable linker strategy.

Using HEK-Blue mTLR9 reporter cells, it was found that AG9 also activated mouse TLR9 and achieved activity similar to unconjugated parent AG1 and superior to Pro-Mune, an unmodified, full phosphorothioate containing ODN2006, in the reporter cells, indicating that AG9 could be used in mouse in vivo models (FIG. 20). The results indicate that in a TLR9 agonist according to an embodiment of the present disclosure, a cleavable linker is preferred in order to optimize its TLR9 stimulatory capability.

Example 8

In Vivo Analysis of TLR9 Agonists

Figure 4:
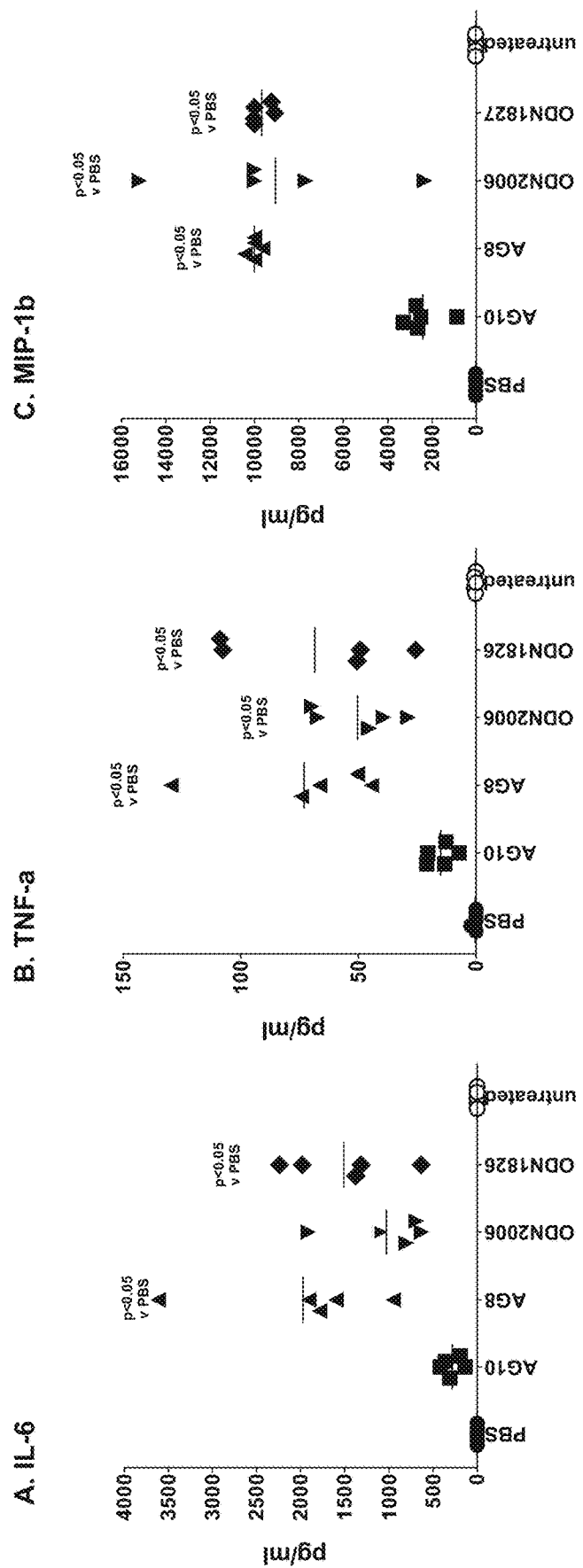
FIG. 4 shows in vivo cytokine induction in mice (IL-6, left panel; TNF-α, middle panel; MIP-1, right panel) by ODN constructs according to embodiments of the present disclosure at 4 h after the administration of the ODN constructs.

Mice were injected subcutaneously with 7.6-10.8 mg/kg of TLR9 agonists AG8 and AG10 and bled 4 hours later. AG8 is conjugated to cholesterol and a cleavable linker on the 5' end of the oligo, and AG10 is conjugated to cholesterol and a cleavable linker on the 3' end of the oligo. The collected samples were analyzed for cytokine levels using a Luminex assay. The results, shown in FIG. 4, indicate that the TLR9 agonists induced cytokine production in vivo. These experiments indicated that, as observed in vitro with the HEK-BLUE mTLR9 cells reporter assay, the polarity of the linker and cholesterol was important in the ability of AG10 to agonize TLR9. While AG10 had little activity in vivo, AG8 could induce proinflammatory cytokines such as IL-6, TNFa and MIP-1b after dosing. Notably, the levels of cytokines produced were on average higher than that of the control ODN2006, and on par with ODN1826. Thus the cholesterol conjugated CpG ODN is active in vivo.

Example 9

Analysis of the Effect of TLR9 Agonists on AAV-HBV Infected Mice

Figure 5:
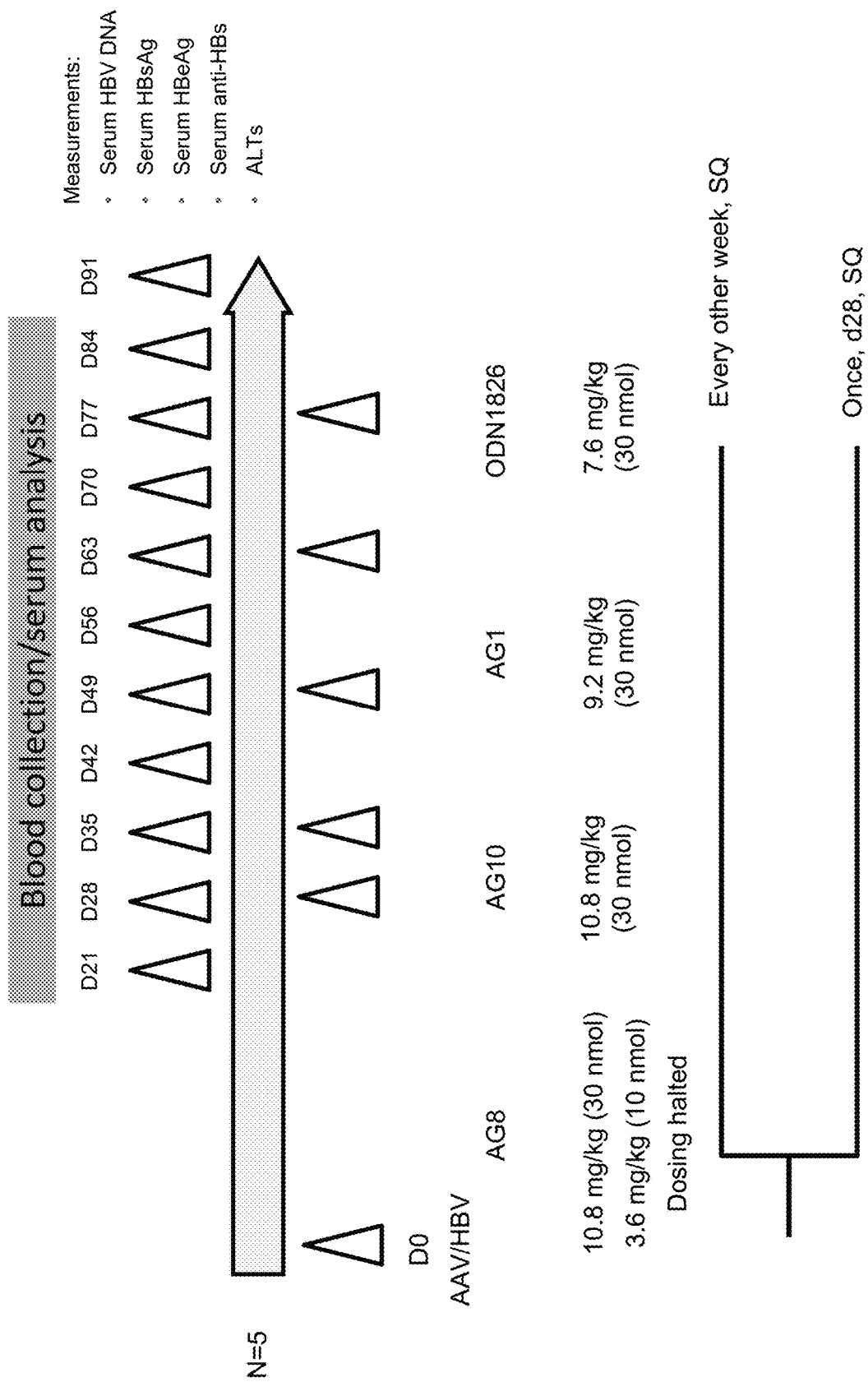
FIG. 5 shows a schematic of an experiment carried out to analyze the effect of ODN constructs according to embodiments of the present disclosure on HBV infection in mice.

A schematic of an experiment carried out to analyze the effect of TLR9 agonists on HBV infection in mice is shown in FIG. 5.

Figure 6:
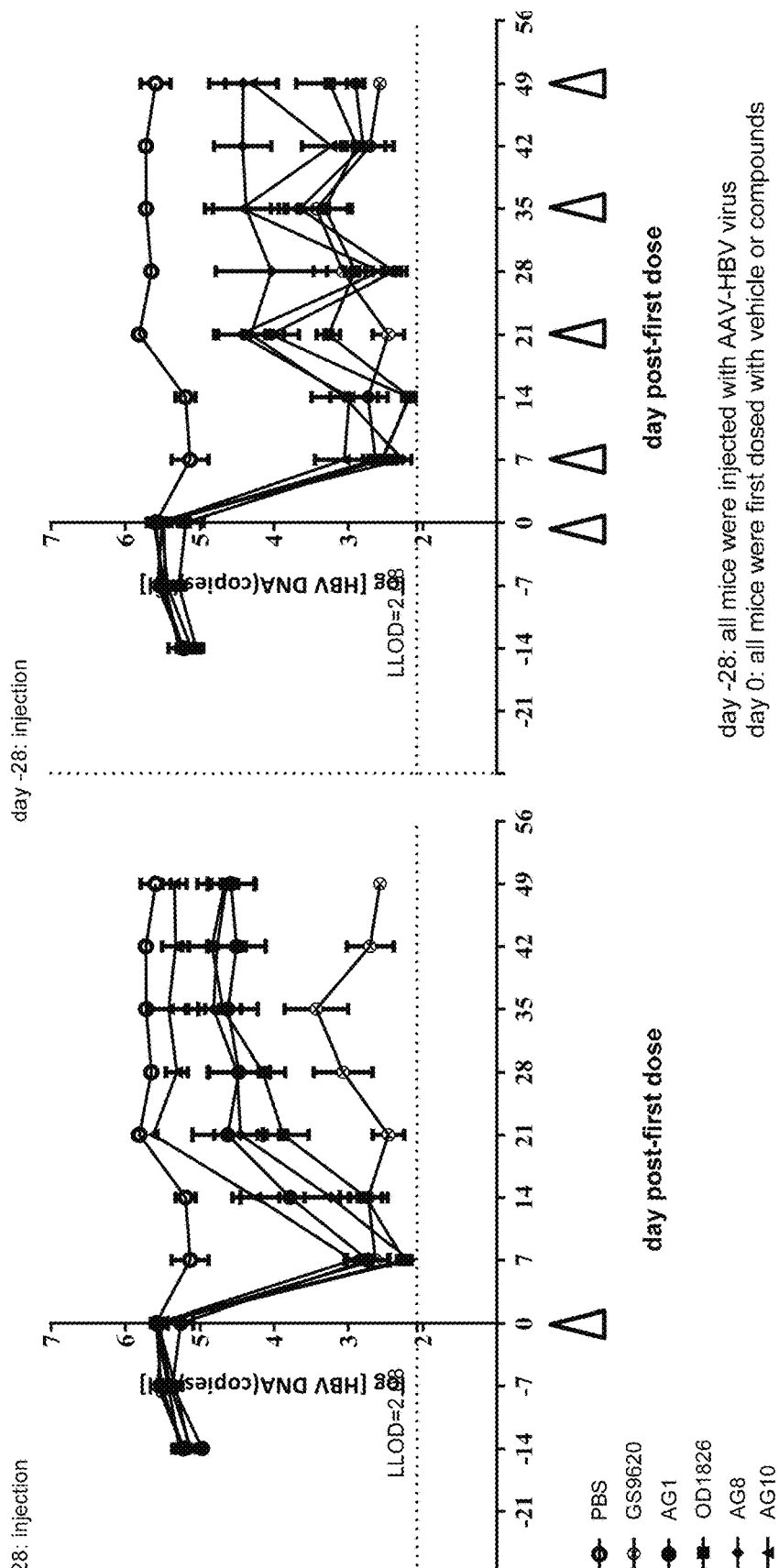
FIG. 6 shows the levels of HBV DNA in mice upon treatment with a single dose (left panel) or multiple doses (right panel) of ODN constructs according to embodiments of the present disclosure.
Figure 7:
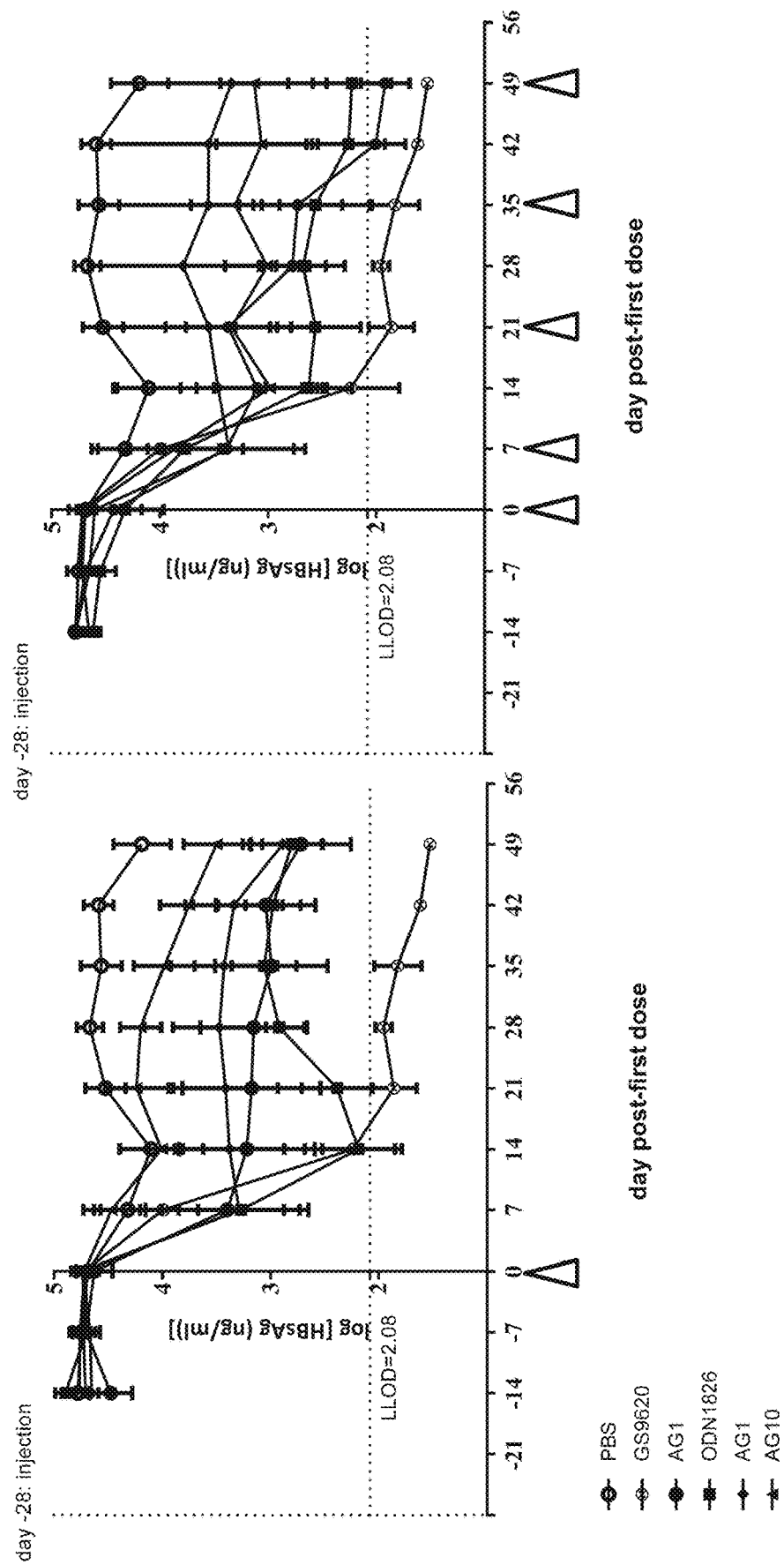
FIG. 7 shows the levels of HBsAg in mice upon treatment with a single dose (left panel) or multiple doses (right panel) of ODN constructs according to embodiments of the present disclosure.
Figure 8:
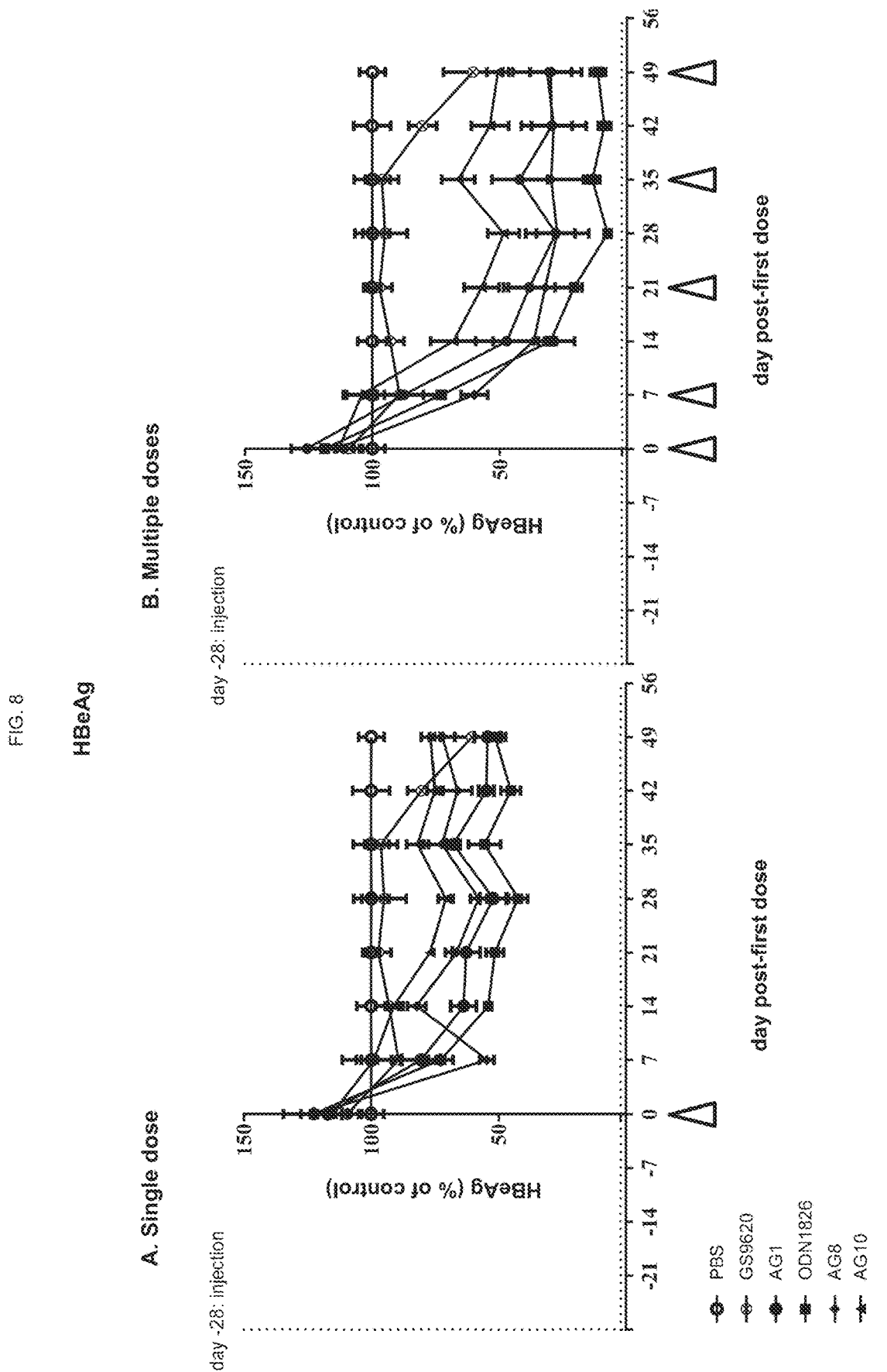
FIG. 8 shows the levels of HBeAg in mice upon treatment with a single dose (left panel) or multiple doses (right panel) of ODN constructs of the present disclosure.

Mice that had been injected with AAV-HBV virus on Day −28 were dosed with vehicle or TLR9 agonists and assessed for levels of HBV indicators. Mice were either given a single dose on Day 0 or multiple doses, on Days 7, 21, 35 and 49. As a benchmark, one group of mice were dosed orally with GS9620, a small molecule agonist of TLR7. All mice were assessed for the level of HBV DNA (see FIG. 6), HBsAg (the surface antigen of HBV; see FIG. 7), and HBeAg (the envelope antigen of HBV; see FIG. 8). The results indicated that administration of the TLR9 agonists successfully suppressed HBV DNA, HBsAg and HBeAg in AAV-HBV-administered mice.

Mice that were subcutaneously injected with the TLR9 agonist AG8 were assessed for induced cytokine production. The results, shown in FIG. 9, indicate that 3 nmol of the TLR9 agonist AG8, which did not produce induction-site reactions, induced cytokine levels similar to the TLR9 agonist AG10.

Figure 10:
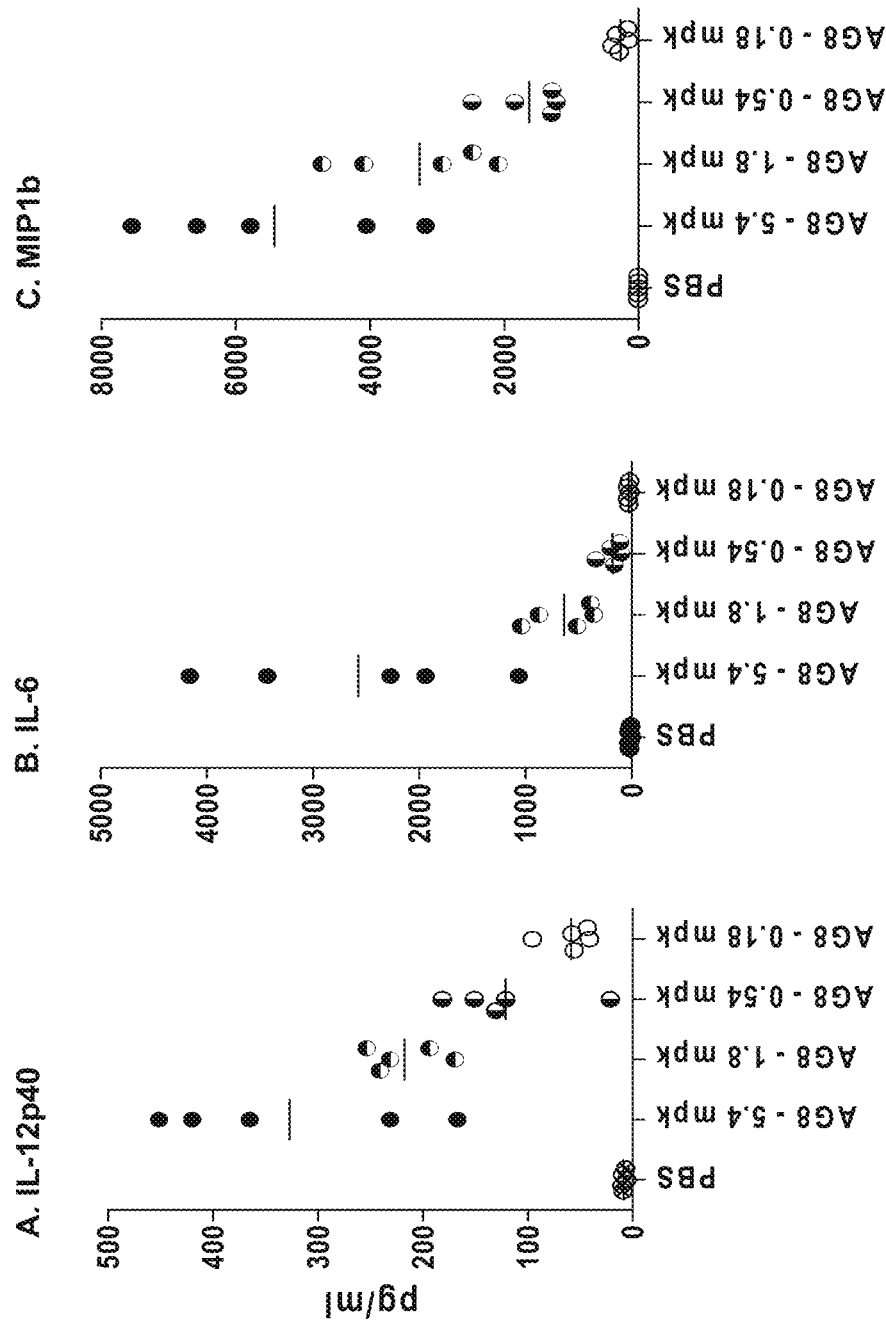
FIG. 10 shows in vivo cytokine induction (IL-12p40, left panel; IL-6, middle panel; MIP-1, right panel) in mice by intravenous injection of an ODN construct of the present disclosure referred to as AG8.
Figure 11:
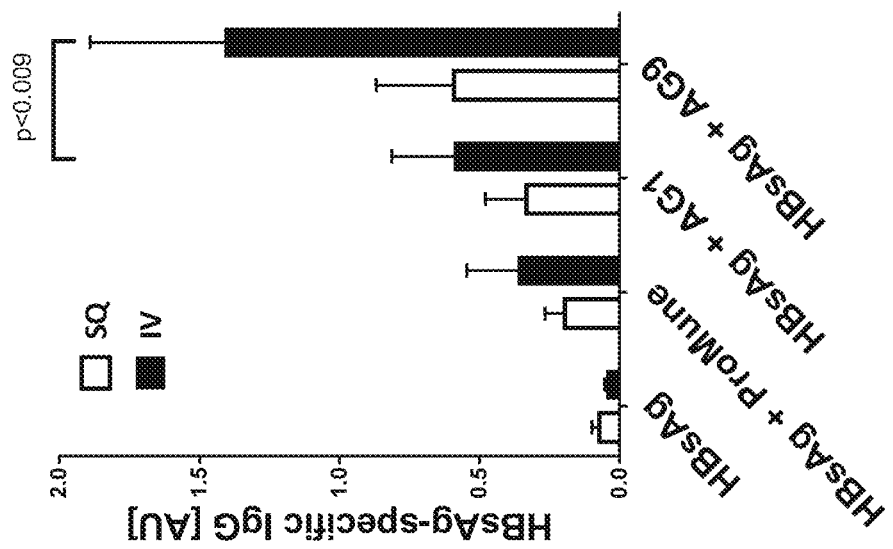
FIG. 11 shows the level of HBsAg specific IgG at Day 14 of mice dosed intravenously (IV) or subcutaneously (SQ) with HBsAg and an ODN construct.

Mice that were intravenously (IV) injected with the TLR9 agonist AG8 were assessed for induced cytokine production. The results, shown in FIG. 10, indicate that 15 nmol of the TLR9 agonist AG8 induced cytokine levels. The IV-injected mice were also analyzed for their HBV viral load. As shown in FIG. 11, IV dosage with AG8 reduced the HBV viral load.

These experiments demonstrated that AG8, either as a single dose, or given QOW for 8 weeks could suppress viral load.

Example 10

TLR9 Agonists Induced a Differential Cytokine Profile

Naïve C57BL/6 mice were injected with the TLR9 agonists AG1, AG8 and AG9, respectively. Serum was sampled at 4 h post injection and measured for cytokines by a Luminex assay.

Figure 9:
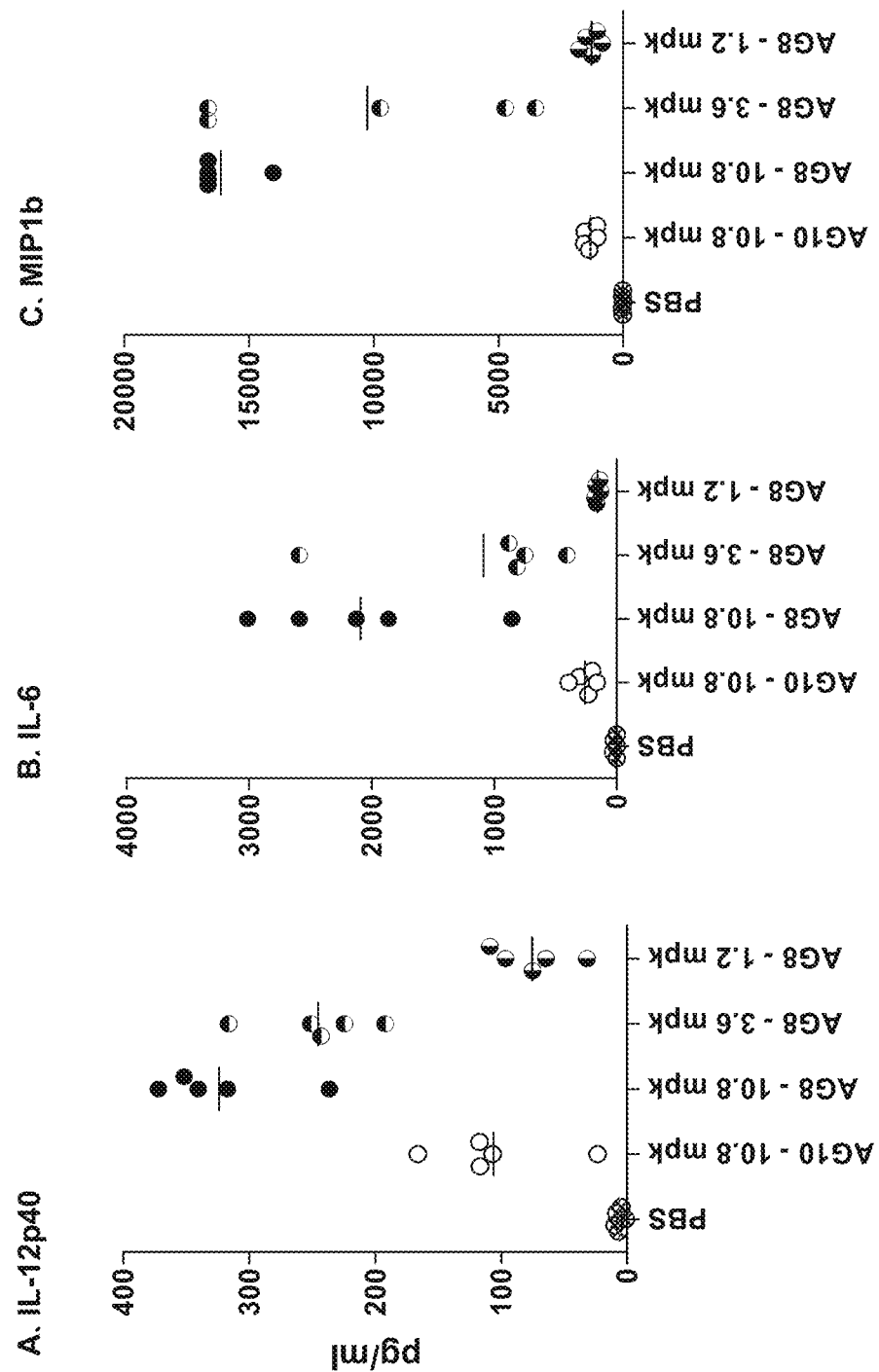
FIG. 9 shows in vivo cytokine induction (IL-12p40, left panel; IL-6, middle panel; MIP-1, right panel) in mice by subcutaneous injection of ODN constructs of the present disclosure.

As shown by the results in FIG. 9, both AG8 and AG9 had increased activity in inducing cytokines IL-12p40, IL-6 and M1P1b, and both activated a different cytokine profile than that of the parent molecule, AG1 (data not shown). Similar pattern of induction was also observed for other cytokines, e.g., IL-12p70, IL-10, G-CSF, IFN-g, IFN-α, TNF-α (data not shown). The cytokine induction was dosage dependent (FIG. 10).

Example 11

AG9 Induces Higher Levels of α-HBsAg than AG1

Mice were immunized subcutaneously or intravenously with 10 μg of recombinant HBsAg in combination with 30 nmol of either AG1 or AG9. Seven days later, mice were bled and serum concentrations of HBsAg-specific antibodies were quantified by ELISA.

As shown in FIG. 11, when dosed subcutaneously, there was a on average a 1.65 fold increase in the levels of α-HBsAg between mice dosed with AG1 (0.332 AU) and AG9 (0.551 AU). When dosed intravenously, the amount of HBsAg-specific antibodies induced by AG9 (1.41 AU) was 2.5 fold more than the amount of antibodies induced by AG1 (0.59 AU) (p<0.009). This suggests that the tocopherol conjugation to the oligonucleotide augments the immunostimulatory activity in order to amplify the immunization process. In addition, intravenous administration of the tocopherol conjugated CpG ODN was much more effective at inducing a humoral response than subcutaneous administration, or intravenous administration of the non conjugated parent, AG1. This result suggests that tocopherol affects biodistribution of the CpG ODN that results in enhanced activity on the humoral response.

Example 12

Conjugation of TLR Agonists to Lipophilic Moieties Via Cleavable Linkers Achieved Functional Cures in AVV-HBV Mice Naïve C57BL/6 mice were infected with AAV-HBV. Once the infection was established, mice were dosed intravenously or subcutaneously every two weeks, with 15 or 30 nmol of the tocopherol conjugate AG9 or the parent, AG1.

Although infected mice responded to subcutaneous administration of either compound, a reduction in either circulating HBV DNA or HBsAg was transient, and levels rebounded after two weeks (FIGS. 13 A&B).

Repeated intravenous administration of 15 nmol AG9 was more potent than that of the parent AG1, as measured by the ability to reduce circulating HBV DNA and HBsAg to below the lower level of quantitation. In addition, after the treatment period, mice were monitored for viral rebound. AG9-treated mice achieved a durable response, with stable suppression of HBsAg and minimal rebound of HBV DNA levels observed at 1 month post dose (FIGS. 13 A&B). This was accompanied by the induction of α-HBsAg Ab in the majority of mice, and by the induction of HBsAg-specific CTLs in some of the mice. In contrast, 3/5 mice treated with the parent, AG1, achieved a durable response, and this was accompanied by α-HBsAg Ab seroconversion and development of HBsAg-specific CTLd. 2/5 AG1-treated mice did not seroconvert. Intravenous administration appeared to be more efficacious than subcutaneous administration.

Analysis of α-HBsAg Ab revealed that more mice treated with AG9 had seroconverted, and on average had greater circulating concentrations of α-HBsAg Ab compared to mice treated with the parent, AG1. These results demonstrate that the tocopherol conjugated CpG oligonucleotide AG9 had a greater ability to produce functional cures in AAV-HBV infected mice than the unconjugated parent, AG1.

To test whether the enhanced efficacy could be applied to other lipophilic moieties, we synthesized AG19 in which we substituted palmitoyl for tocopherol. In vitro experiments in the HEK-hTLR9 line confirmed that AG19 had similar activity to AG9 (data not shown). We repeated the dosing regimen in AAV-HBV infected mice as before, with AG19. Mice were dosed subcutaneously or intravenously every 2 weeks for 14 weeks with 15 nmol of compound. When dosed intravenously (FIG. 13C), AG19 was as effective as AG9 at reducing circulating HBsAg and HBV DNA. After the treatment period, levels of HBsAg remained below the limit of quantification, and HBV-DNA levels were stably suppressed. Similar to AG9 treated mice, suppression of viral load was accompanied by a robust induction of α-HBsAg Ab.

Figure 13D:
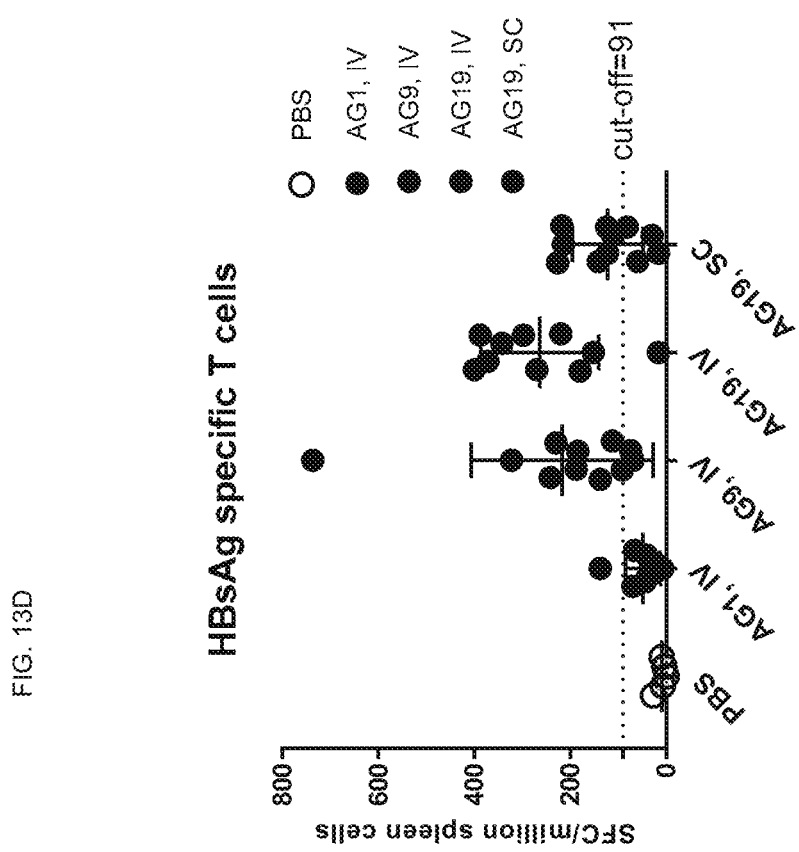
FIG. 13D shows the levels of HBsAg specific T cells in AAV-HBV mice upon administration of ODN constructs according to embodiments of the present disclosure.

At the end of the study, we measured the HBV-specific CTL response by ELISpot. We quantified the number of CTL responding to peptides from HBsAg and found that mice that were treated with AG9 and AG19 had significantly greater numbers of α-HBs CTL, compared to PBS or parental AG1 treated mice (FIG. 13D). Thus conjugating CpG ODNs to lipophilic moieties such as tocopherol or palmitoyl enhanced the agonistic properties of the ODN. HBV specific humoral and cellular responses were generated that suppressed viral load even after drug was withdrawn. By definition, AG9 and AG19 were able to establish a functional cure in subject infected with HBV.

Example 13

Figure 14:
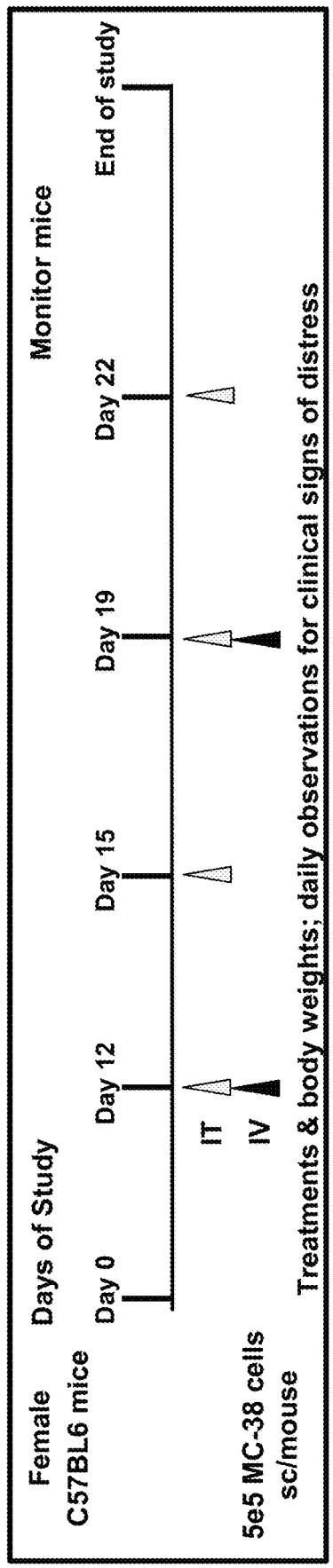
FIG. 14 shows a schematic of a pilot efficacy study with an ODN construct according to embodiments of the present disclosure dosed intratumorally (IT) and intravenously (IV) in MC-38 tumor-bearing mice (colorectal cancer model)

AG9 Achieves Complete Tumor Regression and Tumor Control in the MC-38 Tumor Model Naïve C57BL/6 mice were implanted with MC-38 colon carcinoma cells, and tumor size was monitored. After the tumor was established, mice were dosed intratumorally or intravenously with increasing amounts of the tocopherol conjugate AG9 or the parent AG1. AG14, another CpG ODN having the sequence of TpsCpsGpsTpsCpoGpsTpsTpsApsCpsGpsTpsApsApsCpsGpsApsCpsGpsApsCpsGpsTpsT, was also tested. The doses used were 40 μg, 120 μg and 360 μg, corresponding to 1.6 mpk, 4.8 mpk and 14.4 mpk, respectively. When the mice were treated intratumorally, they were given 4 doses over 10 days (d12, d15, d19 and d22 post implantation). When the mice were dosed intravenously, they were given 2 doses, 7 days apart (d12, d19 post implantation). Tumor growth was monitored every 3 days. See FIG. 14 for additional information about the study.

Intratumoral dosing of either AG1 or AG9 had equivalent efficacy (data not shown). At the 40 μg dose of each group, one mouse had complete tumor regression, and the remaining mice had delayed tumor growth. In the 120 μg dose of each group, three mice had complete tumor regression, and two had delayed tumor growth. In the 360 μg AG dose, three mice had complete regression and one mouse had delayed tumor growth. In the 360 μg AG9 dose, two mice had complete regression, and the remaining mice had tumor stasis.

Figure 15A:
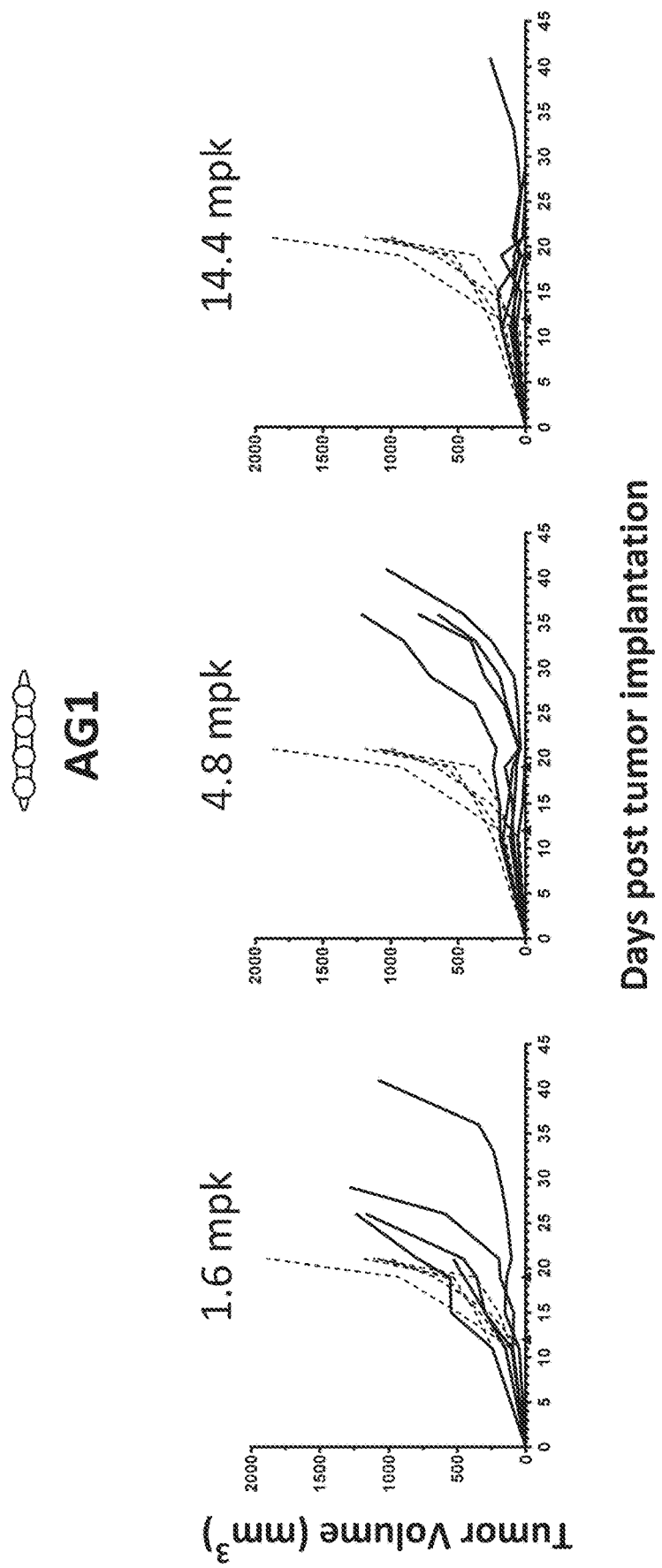
FIGS. 15A-15C show the tumor volume in naïve C57BL/6 mice implanted with MC-38 colon carcinoma cells after being dosed intravenously with increasing amounts of ODN constructs according to embodiments of the present disclosure, in particular.
Figure 15B:
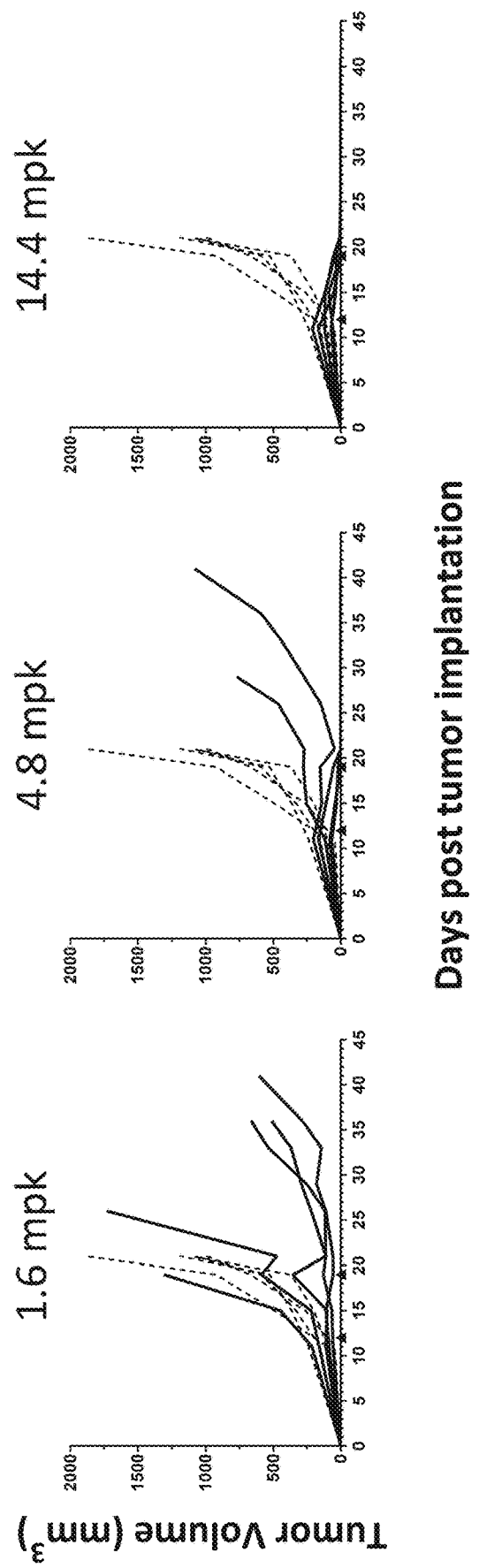
Figure 15C:
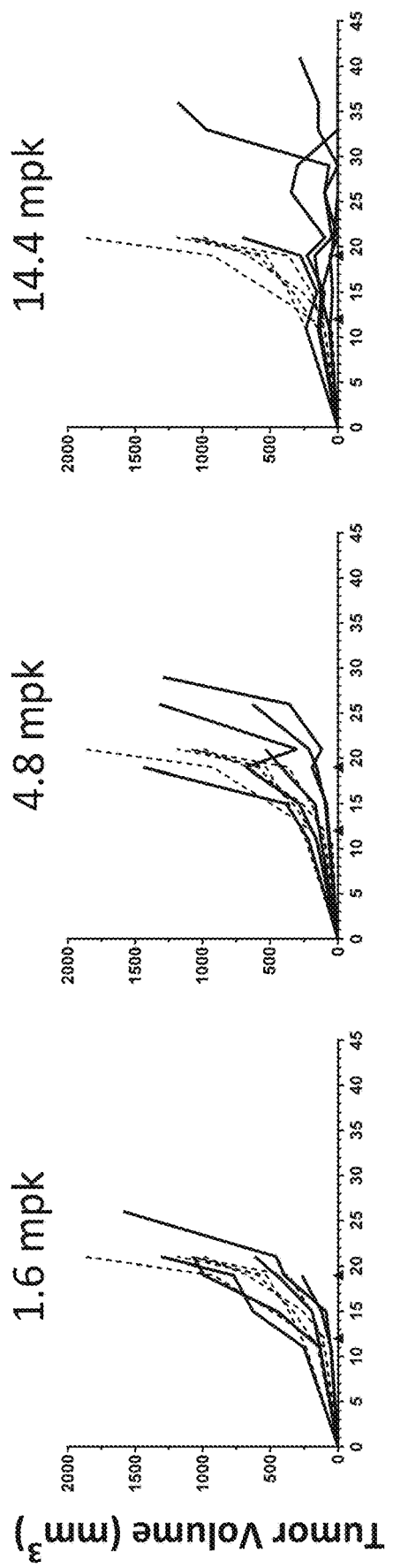

As shown by the results in FIG. 15B, when dosed intravenously, AG9 was more efficacious than AG1 and AG14. At the 40 µg dose of each group, three mice treated with AG9 had delayed tumor growth, whereas two mice treated with AG1 had delayed tumor growth. In the 120 µg dose, three mice treated with AG9 had complete tumor regression and the other two mice had delayed tumor growth. One mouse in the AG-treated group had complete tumor regression, and other four mice had delayed tumor growth. At the highest dose of 360 µg, all mice that received AG9 had complete tumor regression. In mice treated with AG9, no tumor intake or growth was observed even after the mice were re-challenged with MC-38 tumor cells on Day 40 post implantation of the initial tumor. Of the mice receiving AG1, four of the five mice had complete tumor regression and one had delayed tumor growth. These data demonstrate that administering CpG ODNs to activate TLR9 in vivo has therapeutic benefits in treatment of cancer. Furthermore, conjugation of tocopherol by a cleavable linker to the CpG ODN can enhance its therapeutic benefit. In the context MC38, AG9 stimulated the immune response that resulted in tumor clearance and a memory response that prevented tumor regraft. Immunomodulation using AG9 was able to activate an anti-tumor response and allowed formation of a memory response that provided protection against any further recurrence of the tumor.

Example 14

MTD/Efficacy Study with AG9

Figure 16:
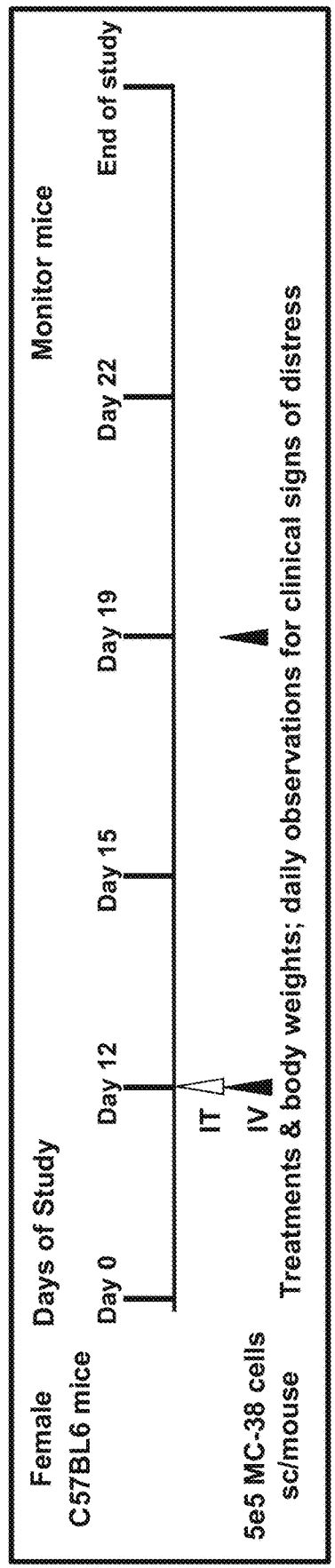
FIG. 16 shows a schematic of a Maximum Tolerated Dose (MTD)/efficacy study with an ODN construct according to an embodiment of the present disclosure in MC-38 tumor bearing mice.

Naïve C57BL/6 mice are implanted with MC-38 colon carcinoma cells, and tumor size was monitored. After the tumor is established, e.g., with mean tumor volume of 100-200 mm$^3$, the mice are dosed intratumorally or intravenously with increasing amounts of the tocopherol conjugate AG9 or the parent AG1 (FIG. 16). The mice are dosed intravenously once per week for two weeks (qwk×2), e.g., on day 12 and day 19, or dosed once intratumorally (qd×1) on day 12.

The primary objective of the study is to determine maximum tolerated dose (MTD) of AG9, dosed qwk×2, in MC-38 tumor bearing mice. The secondary objective of the study is to determine efficacy of AG9, dosed qwk×2, on tumors.

The groups (qwk×2 and qd×1, n=5/group) and dose are as the following:

|  | Group | n | Compound | Dose (mpk) | Group | n | Compound | Dose (mpk) |
|---|---|---|---|---|---|---|---|---|
| Cytokine induction | 1 | 10 | Vehicle |  |  |  |  |  |
|  | 2 | 10 | AG9 | 1.6 | 7 | 5 | CPG7909 | 1.4 |
| MTD/ Efficacy | 3 | 10 | AG9 | 4.8 | 8 | 5 | CPG7909 | 4.1 |
|  | 4 | 10 | AG9 | 14.4 | 9 | 5 | CPG7909 | 12.3 |
|  | 5 | 5 | AG9 | 28.9 | 10 | 5 | CPG7909 | 24.6 |
|  | 6 | 5 | AG9 | 43.3 | 11 | 5 | CPG7909 | 36.9 |
|  | 12 | 3 | Vehicle |  |  |  |  |  |
|  | 13 | 3 | AG9 | 1.6 |  |  |  |  |
|  | 14 | 3 | AG9 | 4.8 |  |  |  |  |
|  | 15 | 3 | AG9 | 14.4 |  |  |  |  |

The mice and the tumor growth are monitored.

Example 15

Other Tumor Models

AG9 was tested in the CT26 tumor mouse model of prostate cancer. BALB/C mice were subcutaneously implanted with 3×10$^5$ CT26 tumor cells in flank and tumor growth is monitored every 3-4 days. When the mean tumor volume reaches 75-125 mm$^3$ (approximately 12 days post implantation), dosing is initiated. The mice were implanted with two doses, Qi W, of 40 nmol of either AG1 or AG9. After 40 days of monitoring, all 8 mice dosed with AG9 were tumor free. In contrast, 7/8 mice receiving AG1 or 8/8 mice receiving PBS had tumors and were euthanized when tumor volumes exceeded 1000 mm$^3$.

AG9 was tested in the A20 tumor mouse model of lymphoma. BALB/C mice were subcutaneously implanted with 1×10$^6$ A20 lymphoma tumor cells in flank and tumor growth is monitored every 3-4 days. When the mean tumor volume reaches 75-125 mm$^3$ (approximately 19 days past implantation), dosing is initiated. The mice were given two doses, Q1W, of 40 nmol of AG9. Mice were monitored for 60 days. At the end of the monitoring period, 50% of the mice were tumor free. In the other 5 subjects, tumor growth was delayed. 2/10 mice experienced tumor burden of approximately 300 mm$^3$ and were euthanized around day 30. One mouse experienced tumor burden of approximately 1000 mm$^3$ around day 40. One mouse experienced tumor burden of approximately 300 mm$^3$ and was euthanized around day 50. One mouse experienced tumor burden of approximately 1000 mm$^3$ and was euthanized around day 50. In contrast, 8/8 PBS treated mice experience tumor burdens exceeding 1500 mm$^3$ before Day 20 and were euthanized.

In summary, these experiments demonstrate the effectiveness of disclosed ODN constructs such as AG9 to treat various cancers such as colorectal carcinoma, prostate cancer and lymphoma.

Example 16

B-Cell Assay

Figure 18:
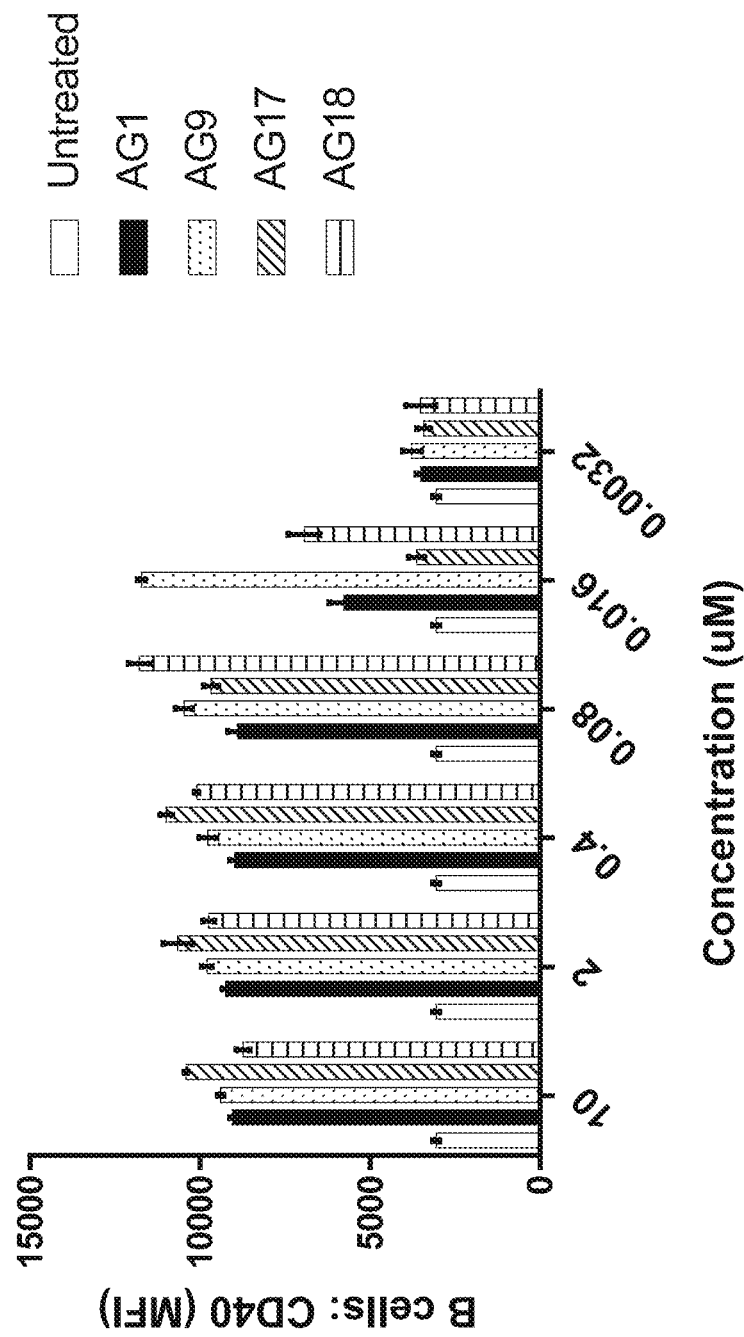
FIG. 18 shows CD40 levels in B cells purified from mouse splenocytes isolated from C57BL/6 mice and stimulated with ODN constructs according to embodiments of the present disclosure.

Mouse splenocytes were isolated from C57BL/6 mice, then B cells were purified using a MACS magnetic bead cell separation column, following manufacturer's protocol. 1×106 B cells were stimulated with the indicated concentration of oligonucleotide at 37° C. for 48 h. Cells were then stained with antibodies specific for activation markers, such as CD40 for 30 min, then washed thrice with FACS Buffer (PBS+3% FBS). Cells were then analyzed by flow cytometry following standard methods. Surface intensity of the markers were quantified by mean fluorescence intensity. Results of this assay are presented in FIG. 18. We compared AG9 and its parent AG1, and AG18, a tocopherol conjugated via indirect linker to AG17, and its parent AG17. Mouse B cells were responsive to all agonists tested, and CD40 upregulation was observed upon stimulation by the agonists in a dose dependent manner. Notably, at 0.016 µM the tocopherol conjugated ODN AG9 and AG18 were more potent than their respective non-conjugated parents, AG1 and AG17. This experiment demonstrated that B cells could be directly stimulated by the tocopherol-conjugated ODNs, and that tocopherol-conjugation potentiated the agonistic activity.

Example 17

Figure 21B:
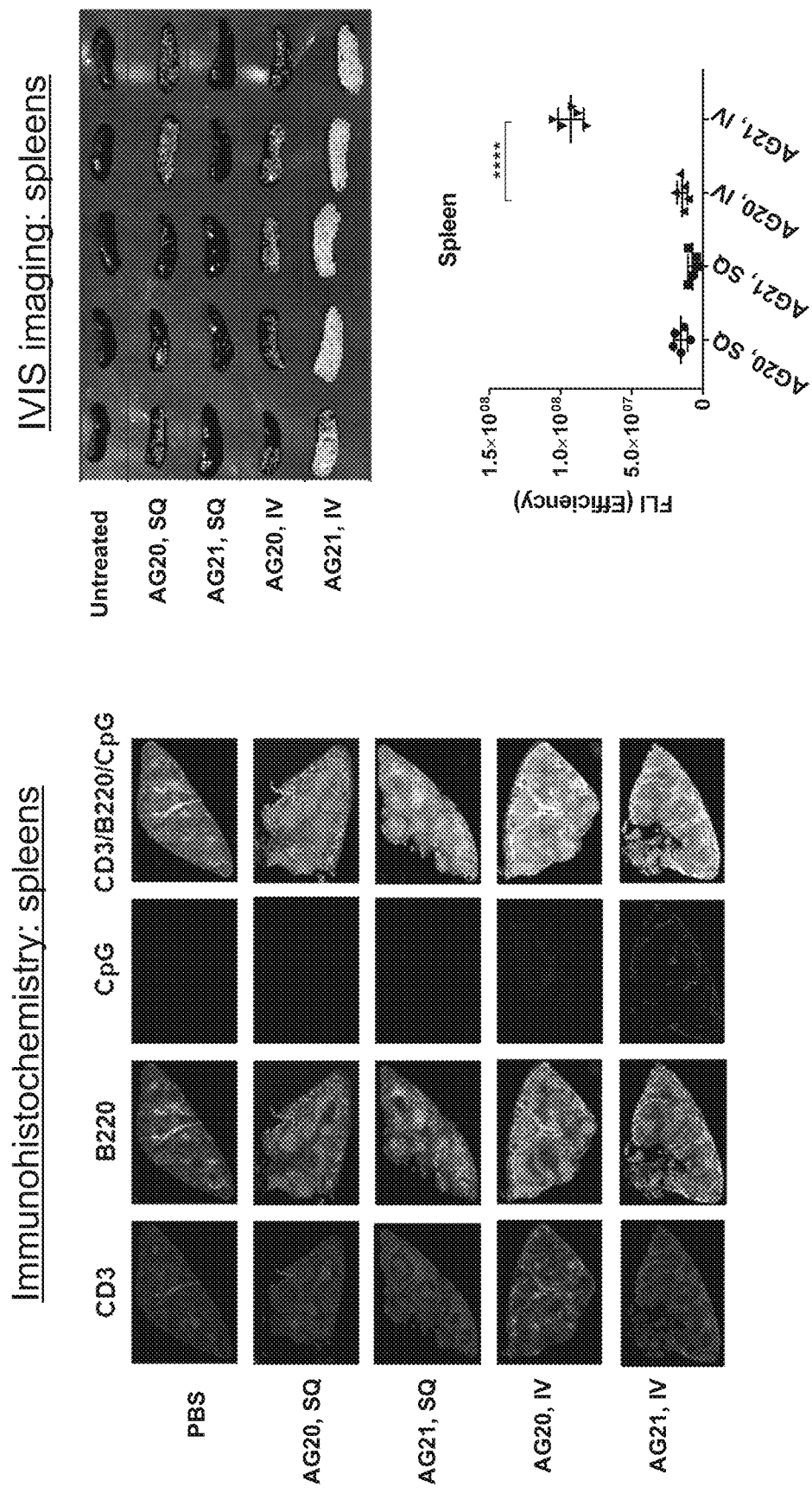
FIG. 21B shows that intravenous (IV) administration of AG21 to mice resulted in oligo accumulation in spleen of the mice as compared to AG20.

Conjugation of TLR Agonists to Tocopherol Via Cleavable Linkers Facilitates In Vivo Biodistribution to Specific Regions within Secondary Lymphoid Organs To determine if tocopherol conjugation would affect the in vivo biodistribution properties of the CpG ODN, mice were injected with AG21 (which is an analog of AG9 conjugated to AlexaFluor-647) or AG20 (which is an analog of AG1 conjugated to AlexaFluor 647) either subcutaneously or intravenously. 24 h post injection spleens, draining lymph nodes, livers, kidneys and lungs were excised and imaged using the IVIS imager. As shown in FIG. 21A, when AG21 was injected subcutaneously, it localized to the draining lymph node as compared to AG20. When quantified, there was more than 2-fold difference between AG21 localization than AG20. In FIG. 21B, spleens were quantified 24 h post IV injection of either compounds. After IV administration, tocopherol affected biodistribution of the compound and using IVIS the majority of AG21 but not AG20 was visualized in the spleen, liver and to a lesser extent, kidney (data not shown). In the spleen, there was nearly a 10-fold increase in the amount of AG21 localization compared to AG20. After either subcutaneous or intravenous administration AG21 localized to secondary lymphoid organs such as the draining lymph nodes or spleen, where it is positioned to activate immune cells. These experiments demonstrate that tocopherol conjugation dramatically affects its biodistribution.

To visualize distribution of AG21 within the secondary lymphoid organs, we repeated the experiment, paraffin embedded the lymph nodes and spleen, sectioned them, and visualized ODN localization by immunofluorescence. The tissues were stain with antibodies directed against T cells or B cells. After subcutaneous injection we observed intense AG21 staining within the B cell follicular region of the lymph node (data not shown). Interestingly after intravenous injection, we observed intense AG21 staining within extrafollicular regions. In AG1 treated mice, we observed weak but detectable ODN staining. These results reaffirm that tocopherol conjugation to the CpG ODN effectively localizes the ODN in the secondary lymphoid organs, and more specifically to isolated regions within the microenvironment.

In order to characterize the cell types that bound to AG21 in the spleen following intravenous injection, we harvested spleens, dissociated them, then stained with fluorescently labeled antibodies directed at specific cell markers in order to differentiate them. Using flow cytometry, we observed that Dendritic Cells and Macrophages, and to lesser extent, B cells were all positive for AG21 (data not shown). T cells were negative for AG21. Thus the cells that were positive for AG21 coincided with cells that express TLR9. This experiment demonstrated that administration of the tocopherol conjugated CpG ODN, the conjugate preferentially directed localization to the secondary lymphoid organs, and within those organs, the conjugate was preferentially taken up by the desired cells, i.e., Dendritic cells, macrophages and B cells.

Example 18

Figure 22A:
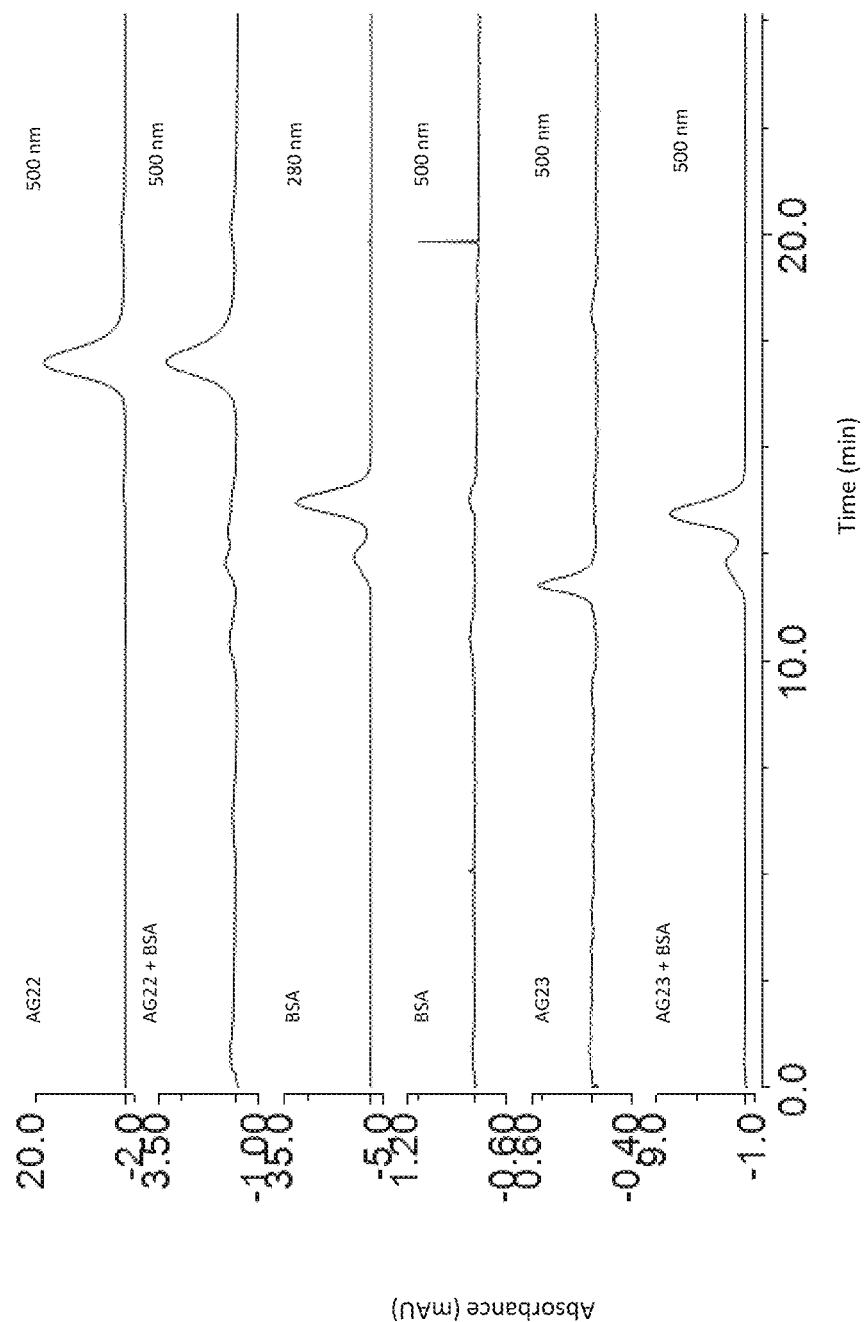
FIG. 22A shows that tocopherol could facilitate binding of the CpG ODN to serum proteins such as bovine serum albumin (BSA)

Conjugation of TLR Agonists to Lipophilic Moieties Via Cleavable Linkers Facilitates Binding to Serum Proteins Such as Albumin It was interesting to observe a skewed distribution pattern of AG21 to some organs such as the liver and spleen, but not to others, such as kidney and lung, both of which are vascularized. We hypothesized that tocopherol could facilitate binding to serum proteins, and based on the distribution of scavenger receptors, that would determine the preferential localization of the tocopherol conjugated CpG ODN. We tested this possibility in vitro. FITC conjugated analogs of AG1 and AG9 were generated. AG22 is an analog of AG1 with FITC conjugated at the 3' end. Similarly, AG23 is an analog of the tocopherol conjugate AG9 with FITC conjugated at the 3' end. The compounds were loaded onto an HPLC, then fluorescence from FITC was monitored (FIG. 22A). The compounds were either alone or premixed with BSA. We observed that the tocopherol conjugated AG23, but not AG22, had a retention time identical with BSA when present. This experiment demonstrated that tocopherol could facilitate binding of the CpG ODN to serum proteins such as BSA. This complex could explain in part the preferential distribution of the tocopherol-conjugated CpG ODN to secondary lymphoid organs and the liver.

Figure 22B:
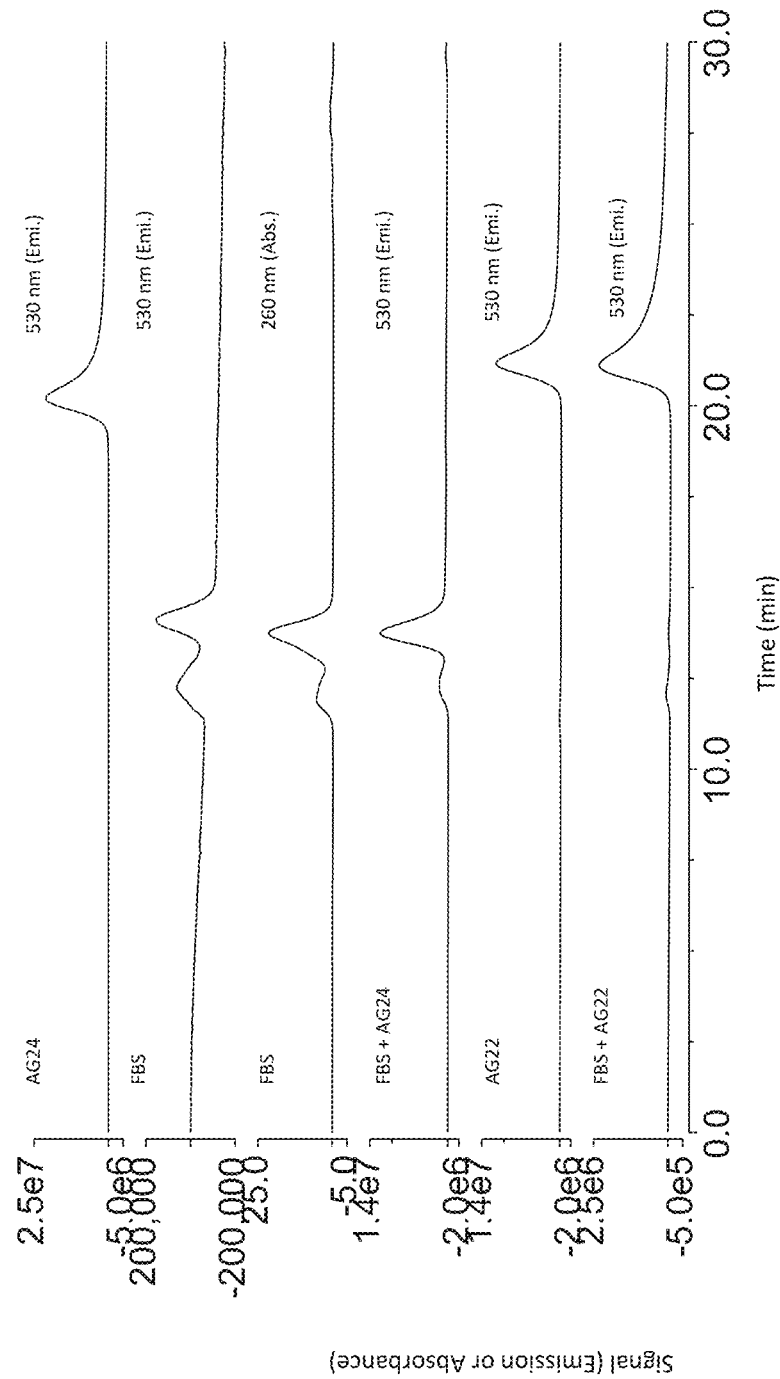
FIG. 22B demonstrates that conjugating the CpG ODN to palmitoyl facilitated the interaction of the ODN to serum proteins within fetal bovine serum (FBS)

We next wondered if the ability to bind to serum proteins was a unique feature of tocopherol conjugation. We synthesized an analog of the palmitoylated compound AG19. AG24 is a CpG ODN that is conjugated to palmitoyl via a cleavable linker on the 5' end, and conjugated to FITC on the 3'end. We repeated the above experiment by mixing AG24 or AG22 to fetal bovine serum (FBS) then analyzing the mixture by HPLC and monitored the retention time of the ODN by its fluorescent signal. As shown in FIG. 22B, the retention time of AG24 but not AG22 was identical to FBS. This demonstrated that conjugating the CpG ODN to palmitoyl facilitated the interaction of the ODN to serum proteins.

Example 19

Figure 23:
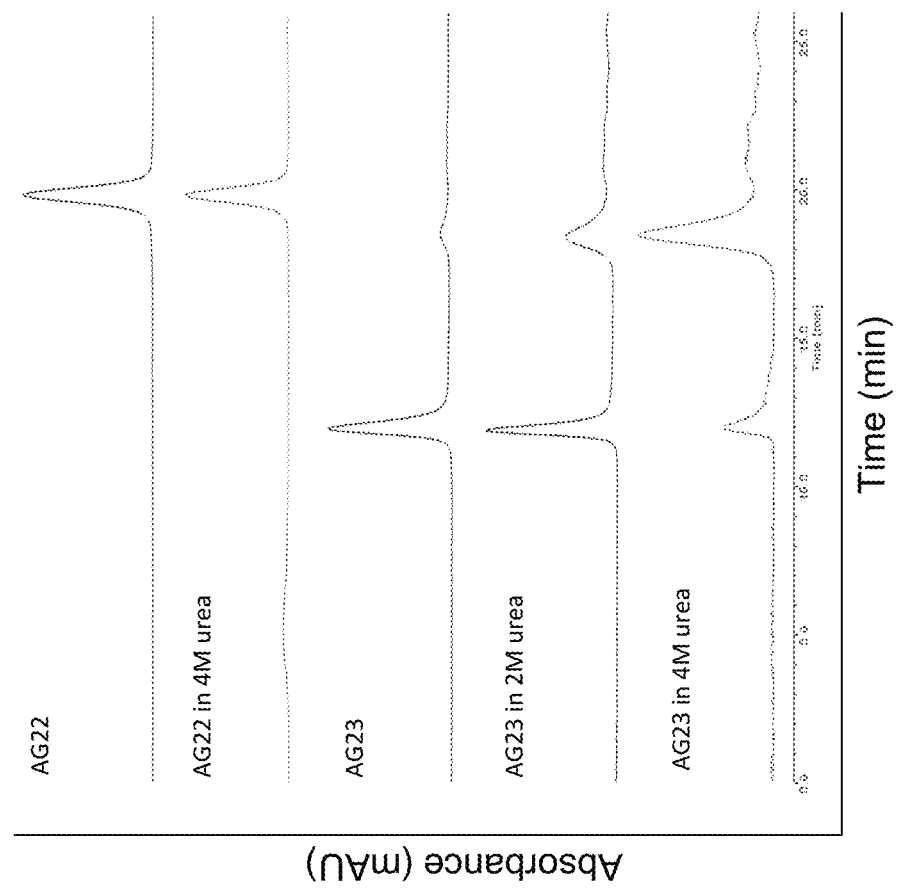
FIG. 23 demonstrates that the tocopherol conjugation of the CpG ODN imparted the property of micelle formation to the ODN.

Conjugation of TLR Agonists to Tocopherol Via Cleavable Linkers Facilitates Self-Formulation into Micelle Structures Because of the lipophilic nature of tocopherol, we also tested the ability of tocopherol conjugation to facilitate micelle formation of the CpG ODN. By monitoring AG23 on the HPLC using the FITC fluorescent signal, we found that in the presence of high concentrations (2 or 4 M) of urea which disrupt micelle formation, the retention time of AG23 altered, whereas the retention time of AG22 was not affected (FIG. 23). These results demonstrated that the tocopherol conjugation of the CpG ODN imparted the property of micelle formation to the ODN.

While the present disclosure has been described in detail, and with reference to specific embodiments thereof, it will be apparent to one of ordinary skill in the art that various changes and modifications can be made therein without departing from the spirit and scope of the present disclosure.

We claim:

1. An ODN construct having the following structure:

5' Toco-po(HEG)po(HEG)po-TpsCpoGpsTpsCpoGpsTpsTpsTpsGpsTpsCpoGpsTpsTpsTpsGpsTpsCpoGpsTpsT 3' (SEQ ID NO: 27);

wherein:

Toco represents tocopherol;

HEG represents $((CH_2)_2O)_6$;

po represents a phosphodiester linkage; and ps represents a phosphorothioate linkage, wherein the tocopherol is covalently linked to the (HEG) directly via the po linkage, or indirectly via a second linker that is linked to (HEG) directly via the po linkage.

2. A pharmaceutical composition comprising the ODN construct of claim 1 and a pharmaceutically acceptable carrier.

* * * * *

SEQUENCE LISTING

<160> NUMBER OF SEQ ID NOS: 56

<210> SEQ ID NO 1
<211> LENGTH: 24
<212> TYPE: DNA

```
<213> ORGANISM: Artificial Sequence
<220> FEATURE:
<223> OTHER INFORMATION: synthetic oligonucleotide

<400> SEQUENCE: 1
tcgtcgtttt gtcgttttgt cgtt                                              24

<210> SEQ ID NO 2
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 2
gggggacgat cgtcggggggg                                                  20

<210> SEQ ID NO 3
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 3
ggggtcaacg ttgagggggg                                                   20

<210> SEQ ID NO 4
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 4
tccatgacgt tcctgacgtt                                                   20

<210> SEQ ID NO 5
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 5
tcgtcgtttt cggcgcgcgc cg                                                22

<210> SEQ ID NO 6
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 6
tcgtcgttac gtaacgacga cgtt                                              24

<210> SEQ ID NO 7
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 7
tcgtcgtttt gtcgttttgt cgt                                               23
```

-continued

<210> SEQ ID NO 8
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 8
tcgtcgtttt gtcgttttgt cgtt                                              24

<210> SEQ ID NO 9
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 9
tcgtcgtttt gtcgttttgt cgtt                                              24

<210> SEQ ID NO 10
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 10
tcgtcgtttt gtcgttttgt cgtt                                              24

<210> SEQ ID NO 11
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 11
tcgtcgtttt gtcgttttgt cgtt                                              24

<210> SEQ ID NO 12
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 12
tcgtcgtttt gtcgttttgt cgtt                                              24

<210> SEQ ID NO 13
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 13
tcgtcgtttt gtcgttttgt cgtt                                              24

<210> SEQ ID NO 14
<211> LENGTH: 24
<212> TYPE: DNA
<213> ORGANISM: Artificial Sequence
<220> FEATURE:

<223> OTHER INFORMATION: synthetic oligonucleotide

<400> SEQUENCE: 14
tcgtcgtttt gtcgttttgt cgtt                                    24

<210> SEQ ID NO 15
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 15
tcgtcgttac gtaacgacga cgtt                                    24

<210> SEQ ID NO 16
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 16
tcgtcgttac gtaacgacga cgtt                                    24

<210> SEQ ID NO 17
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 17
tcgtcgttac gtaacgacga cgtt                                    24

<210> SEQ ID NO 18
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 18
tcgtcgttac gtaacgacga cgtt                                    24

<210> SEQ ID NO 19
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 19
tcgtcgttac gtaacgacga cgtt                                    24

<210> SEQ ID NO 20
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 20
gggggacgat cgtcggggggg                                        20

```
<210> SEQ ID NO 21
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 21
ggggtcaacg ttgagggggg                                                   20

<210> SEQ ID NO 22
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 22
tccatgacgt tcctgacgtt                                                   20

<210> SEQ ID NO 23
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 23
tcgtcgtttt cggcgcgcgc cg                                                22

<210> SEQ ID NO 24
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 24
tcgtcgtttt gtcgttttgt cgt                                               23

<210> SEQ ID NO 25
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 25
tcgtcgtttt gtcgttttgt cgt                                               23

<210> SEQ ID NO 26
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 26
tcgtcgtttt gtcgttttgt cgt                                               23

<210> SEQ ID NO 27
<211> LENGTH: 24
<212> TYPE: DNA
<213> ORGANISM: Artificial Sequence
<220> FEATURE:
<223> OTHER INFORMATION: synthetic oligonucleotide
```

```
<400> SEQUENCE: 27
tcgtcgtttt gtcgttttgt cgtt                                          24

<210> SEQ ID NO 28
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 28
tcgtcgtttt gtcgttttgt cgtt                                          24

<210> SEQ ID NO 29
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 29
tcgtcgtttt gtcgttttgt cgtt                                          24

<210> SEQ ID NO 30
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 30
tcgtcgtttt gtcgttttgt cgtt                                          24

<210> SEQ ID NO 31
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 31
tcgtcgtttt gtcgttttgt cgtt                                          24

<210> SEQ ID NO 32
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 32
tcgtcgtttt gtcgttttgt cgtt                                          24

<210> SEQ ID NO 33
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 33
tcgtcgtttt gtcgttttgt cgtt                                          24

<210> SEQ ID NO 34
<211> LENGTH: 24
```

```
<212> TYPE: DNA
<213> ORGANISM: Artificial Sequence
<220> FEATURE:
<223> OTHER INFORMATION: synthetic oligonucleotide

<400> SEQUENCE: 34
tcgtcgtttt gtcgttttgt cgtt                                              24

<210> SEQ ID NO 35
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 35
tcgtcgtttt gtcgttttgt cgtt                                              24

<210> SEQ ID NO 36
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 36
tcgtcgtttt gtcgttttgt cgtt                                              24

<210> SEQ ID NO 37
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 37
tcgtcgtttt gtcgttttgt cgtt                                              24

<210> SEQ ID NO 38
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 38
tcgtcgtttt gtcgttttgt cgtt                                              24

<210> SEQ ID NO 39
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 39
tcgtcgtttt gtcgttttgt cgtt                                              24

<210> SEQ ID NO 40
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 40
```
tcgtcgtttt gtcgttttgt cgtt 24

<210> SEQ ID NO 41
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 41
tcgtcgtttt gtcgttttgt cgtt 24

<210> SEQ ID NO 42
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 42
tcgtcgtttt gtcgttttgt cgtt 24

<210> SEQ ID NO 43
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 43
tcgtcgtttt gtcgttttgt cgtt 24

<210> SEQ ID NO 44
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 44
tcgtcgtttt gtcgttttgt cgtt 24

<210> SEQ ID NO 45
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 45
tcgtcgtttt gtcgttttgt cgtt 24

<210> SEQ ID NO 46
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 46
tcgtcgtttt gtcgttttgt cgtt 24

<210> SEQ ID NO 47
<211> LENGTH: 24
<212> TYPE: DNA
<213> ORGANISM: Artificial Sequence

```
<220> FEATURE:
<223> OTHER INFORMATION: synthetic oligonucleotide

<400> SEQUENCE: 47
tcgtcgtttt gtcgttttgt cgtt                                              24

<210> SEQ ID NO 48
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 48
tcgtcgtttt gtcgttttgt cgtt                                              24

<210> SEQ ID NO 49
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 49
tcgtcgtttt gtcgttttgt cgtt                                              24

<210> SEQ ID NO 50
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 50
tcgtcgtttt gtcgttttgt cgtt                                              24

<210> SEQ ID NO 51
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 51
tcgtcgtttt gtcgttttgt cgtt                                              24

<210> SEQ ID NO 52
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 52
tcgtcgtttt gtcgttttgt cgtt                                              24

<210> SEQ ID NO 53
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 53
ggggtcaacg ttgagggggg                                                   20
```

```
<210> SEQ ID NO 54
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 54
tccatgacgt tcctgacgtt                                               20

<210> SEQ ID NO 55
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 55
tccatgacgt tcctgacgtt                                               20

<210> SEQ ID NO 56
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 56
tcgtcgtttt gtcgttttgt cgtt                                          24
```